US012765829B2

(12) United States Patent
Shachar et al.

(10) Patent No.: US 12,765,829 B2
(45) Date of Patent: Oct. 20, 2026

(54) ROBOTICALLY CONTROLLED ELECTROPHYSIOLOGY CATHETER WITH CLOSED LOOP CONTROL

(71) Applicant: Neuro-Kinesis Corporation, Inglewood, CA (US)

(72) Inventors: Josh Shachar, Santa Monica, CA (US); Marc Rocklinger, Los Angeles, CA (US); Eli Gang, Los Angeles, CA (US); Peter Yin, Culver City, CA (US); Dylan Bourdages, Redlands, CA (US)

(73) Assignee: Neuro-Kinesis Corporation, Inglewood, CA (US)

(*) Notice: Subject to any disclaimer, the term of this patent is extended or adjusted under 35 U.S.C. 154(b) by 134 days.

(21) Appl. No.: 18/608,388

(22) PCT Filed: May 20, 2022

(86) PCT No.: PCT/US2022/030399

§ 371 (c)(1),
(2) Date: Mar. 18, 2024

(87) PCT Pub. No.: WO2023/038682

PCT Pub. Date: Mar. 16, 2023

(65) Prior Publication Data

US 2025/0228486 A1 Jul. 17, 2025

Related U.S. Application Data

(63) Continuation-in-part of application No. 17/468,460, filed on Sep. 7, 2021, now Pat. No. 12,279,876.

(51) Int. Cl.

| | |
|---|---|
| ***A61B 5/287*** | (2021.01) |
| ***A61B 5/00*** | (2006.01) |

(Continued)

(52) U.S. Cl.

CPC ............ *A61B 5/367* (2021.01); *A61B 5/0006* (2013.01); *A61B 5/0017* (2013.01); *A61B 5/201* (2013.01);

(Continued)

(58) Field of Classification Search

CPC ....... A61B 5/282; A61B 5/287; A61B 5/6852; A61B 18/1492; A61B 2018/00839

See application file for complete search history.

(56) References Cited

U.S. PATENT DOCUMENTS

| | | | | | |
|---|---|---|---|---|---|
| 2003/0204220 | A1* | 10/2003 | Forsberg | A61N 1/0551 | 607/48 |
| 2012/0323237 | A1* | 12/2012 | Paul | A61B 18/1206 | 606/41 |

(Continued)

FOREIGN PATENT DOCUMENTS

| | | | | |
|---|---|---|---|---|
| WO | WO-2008045938 A2 * | 4/2008 | A61B 5/283 |
| WO | 2021084476 | 5/2021 | |
| WO | 2021165882 | 8/2021 | |

OTHER PUBLICATIONS

Josh Shachar, Inventor Scientist Enterpreneur, obtained from https://joshshachar.com/wp-content/uploads/2021/10/jshachar-cv.pdf on Dec. 19, 2025.

*Primary Examiner* — Eun Hwa Kim
(74) *Attorney, Agent, or Firm* — Kirton McConkie; Brian Tucker

(57) ABSTRACT

The embodiments include an apparatus used in combination with a computer for sensing biopotentials and electrode contact impedance. The apparatus includes a catheter in which there is a plurality of sensing electrodes, a corresponding plurality of local amplifiers, each coupled to one of the plurality of sensing electrodes, a data, control and power circuit coupled to the plurality of local amplifiers, and a photonic device bi-directionally communicating an electri- (Continued)

cal signal with the data, control and power circuit. An optical fiber optically communicated with the photonic device. The photonic device bi-directionally communicates an optical signal with the optical fiber. An optical interface device provides optical power to the optical fiber and thence to the photonic device and receives optical signals through the optical fiber from the photonic device. The optical interface device bi-directionally communicates electrical data, control, and power signal to the computer.

20 Claims, 53 Drawing Sheets

(51) Int. Cl.

| | |
|---|---|
| ***A61B 5/20*** | (2006.01) |
| ***A61B 5/283*** | (2021.01) |
| ***A61B 5/294*** | (2021.01) |
| ***A61B 5/308*** | (2021.01) |
| ***A61B 5/35*** | (2021.01) |
| ***A61B 5/367*** | (2021.01) |
| ***A61B 5/388*** | (2021.01) |
| ***G16H 40/63*** | (2018.01) |

(52) U.S. Cl.

CPC .............. *A61B 5/287* (2021.01); *A61B 5/294* (2021.01); *A61B 5/308* (2021.01); *A61B 5/35* (2021.01); *A61B 5/388* (2021.01); *A61B 5/4836* (2013.01); *A61B 5/6852* (2013.01); *A61B 5/686* (2013.01); *A61B 5/7203* (2013.01); *A61B 5/7271* (2013.01); *A61B 5/742* (2013.01); *G16H 40/63* (2018.01); *A61B 2560/0468* (2013.01); *A61B 2562/0209* (2013.01); *A61B 2562/146* (2013.01); *A61B 2562/166* (2013.01)

(56) References Cited

U.S. PATENT DOCUMENTS

| | | | | |
|---|---|---|---|---|
| 2014/0018792 | A1* | 1/2014 | Gang | A61B 18/1492 606/41 |
| 2014/0371576 | A1* | 12/2014 | Hauck | A61B 5/7425 600/424 |
| 2015/0313501 | A1 | 11/2015 | Shachar | |
| 2018/0078300 | A1 | 3/2018 | Jude | |
| 2019/0388148 | A1* | 12/2019 | Wu | A61B 5/062 |
| 2020/0375541 | A1 | 12/2020 | Shachar | |

* cited by examiner

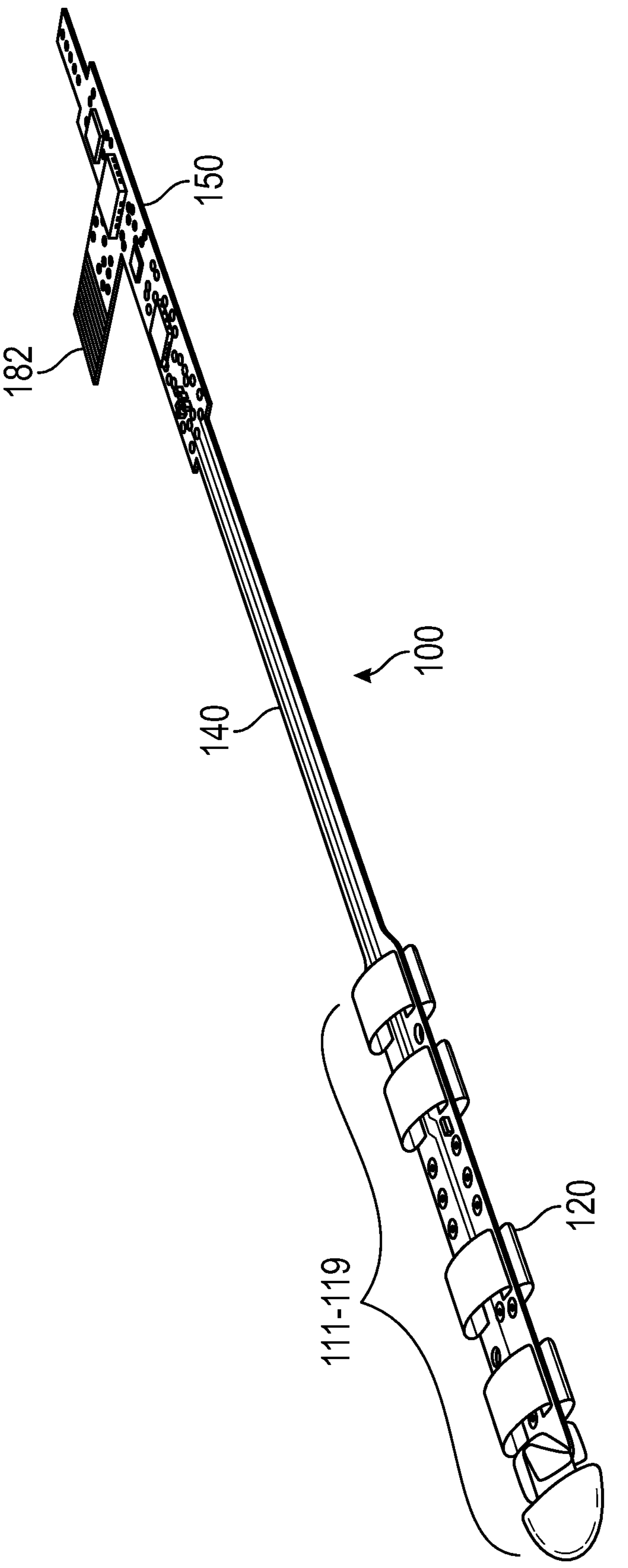
FIG. 1.1

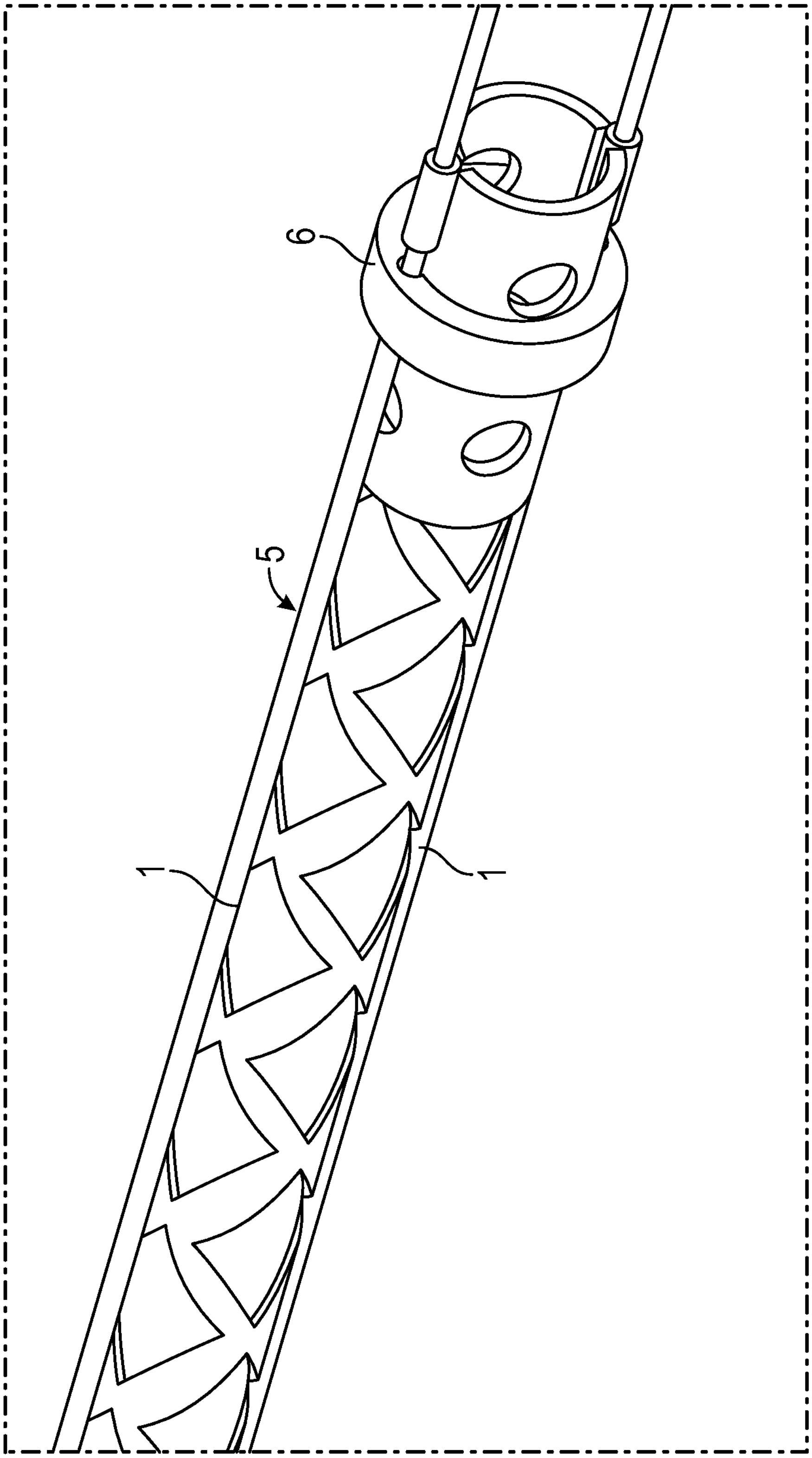
FIG. 1.2

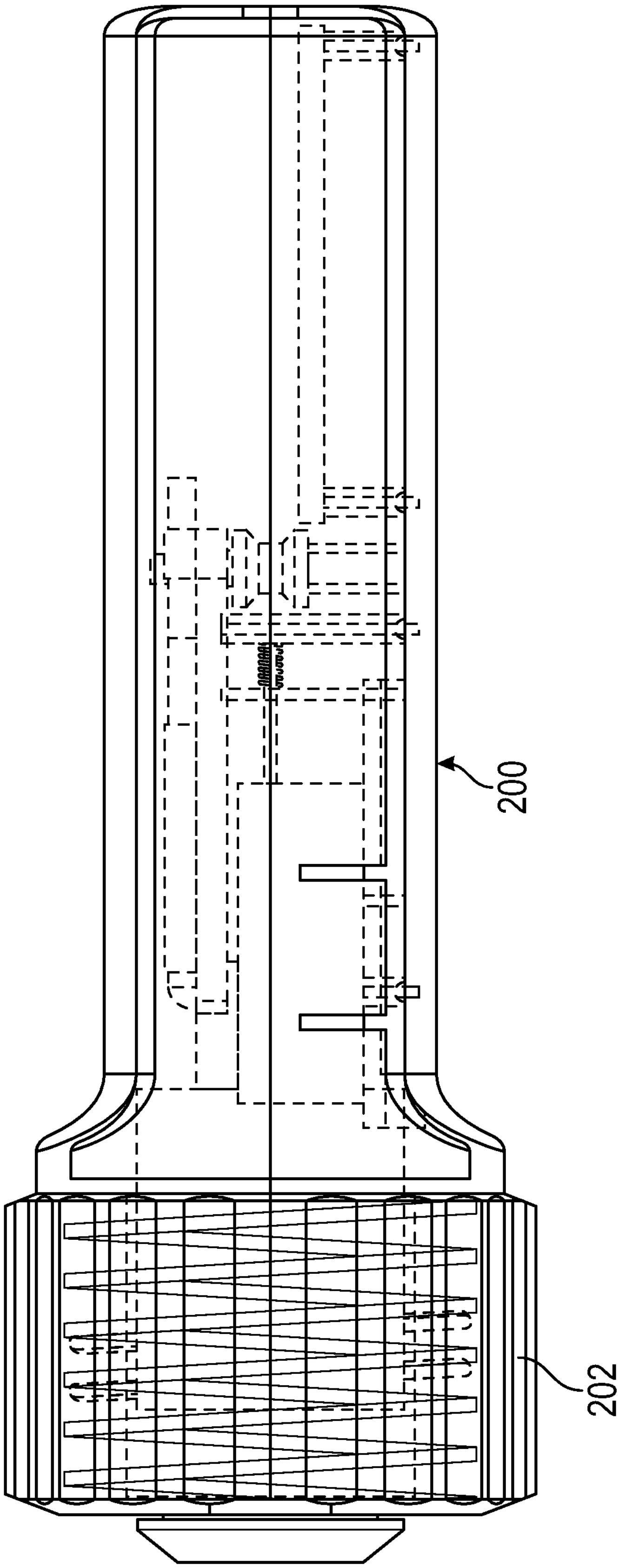
FIG. 1.3

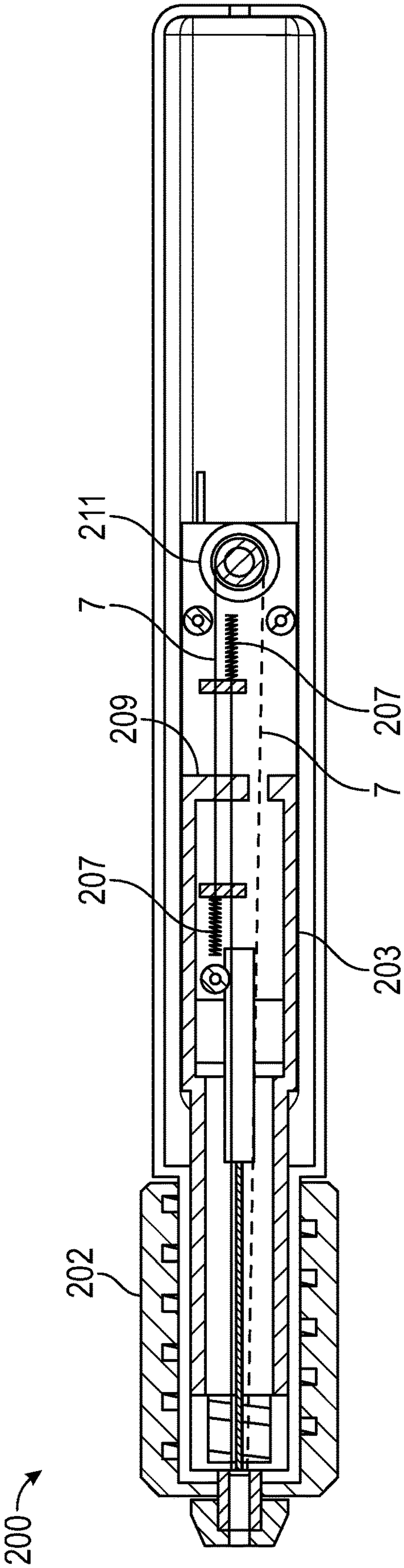
FIG. 1.4

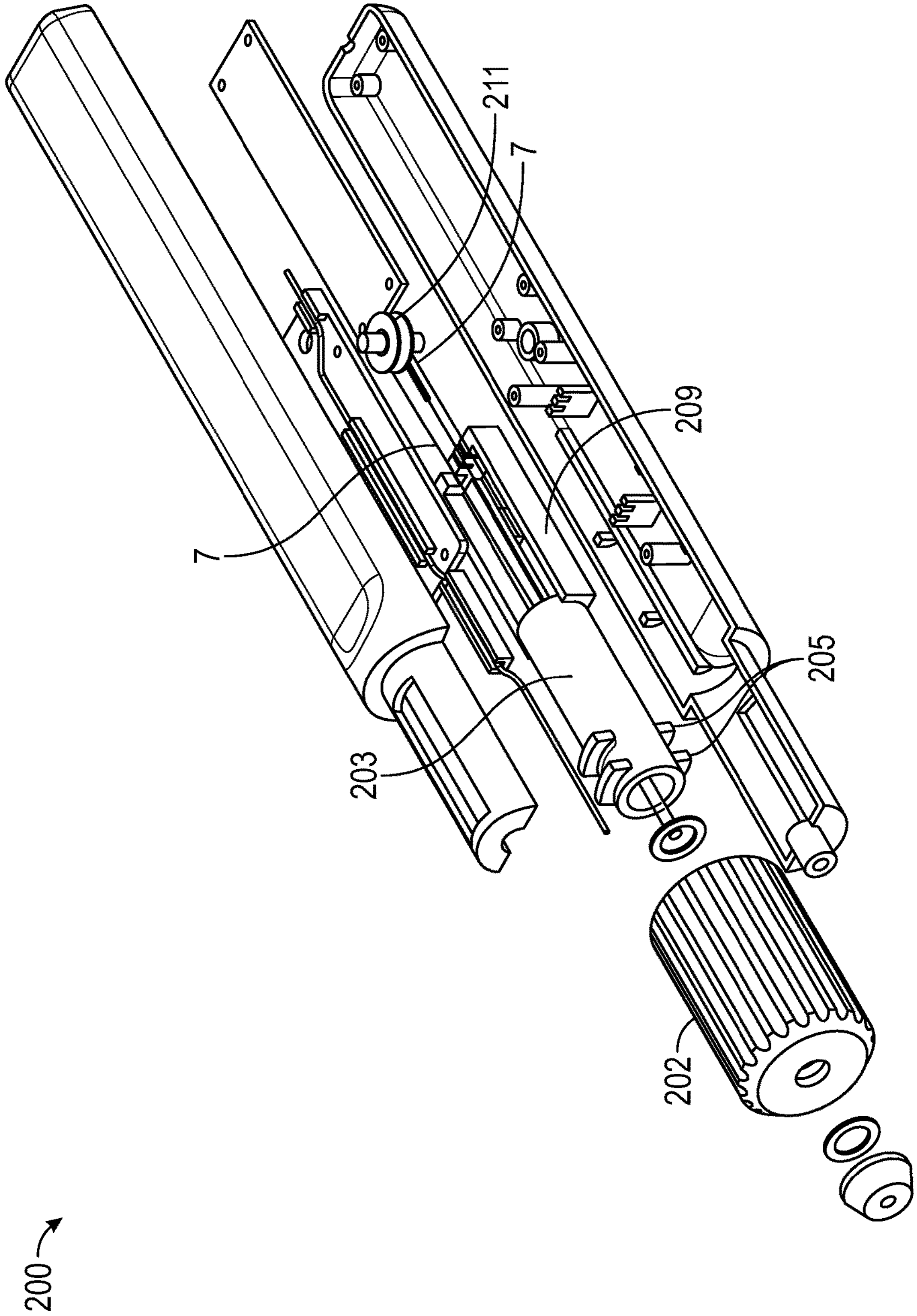
FIG. 1.5

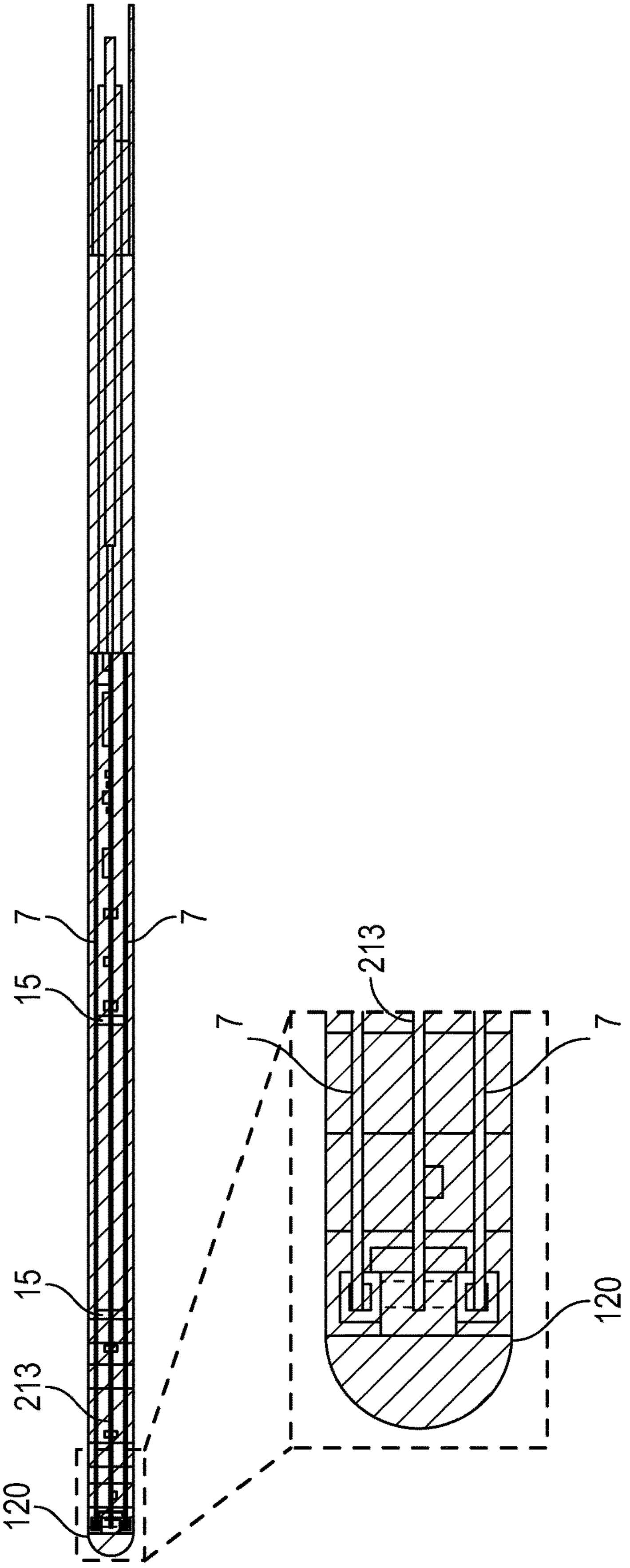
FIG. 1.6

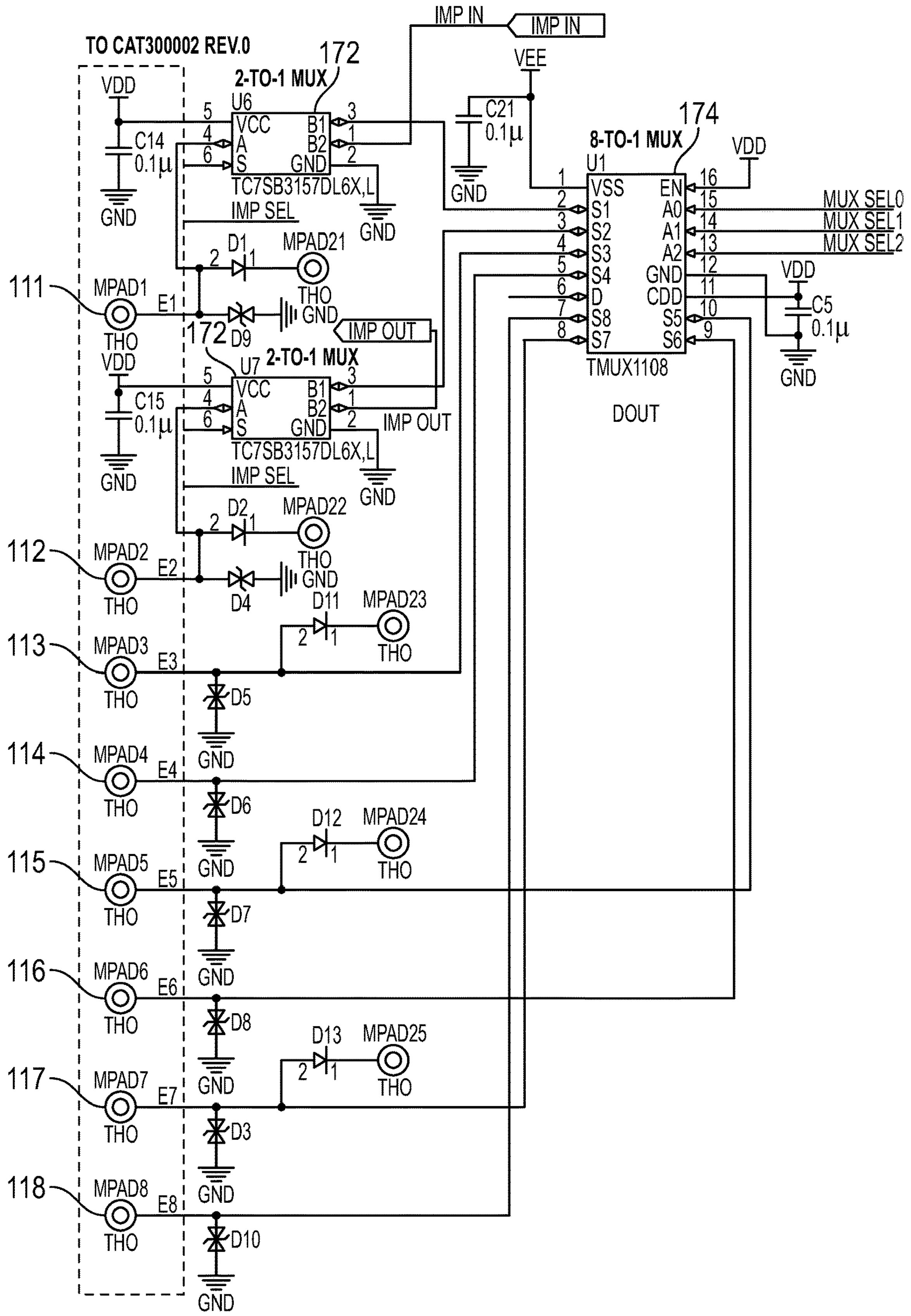
FIG. 7.1

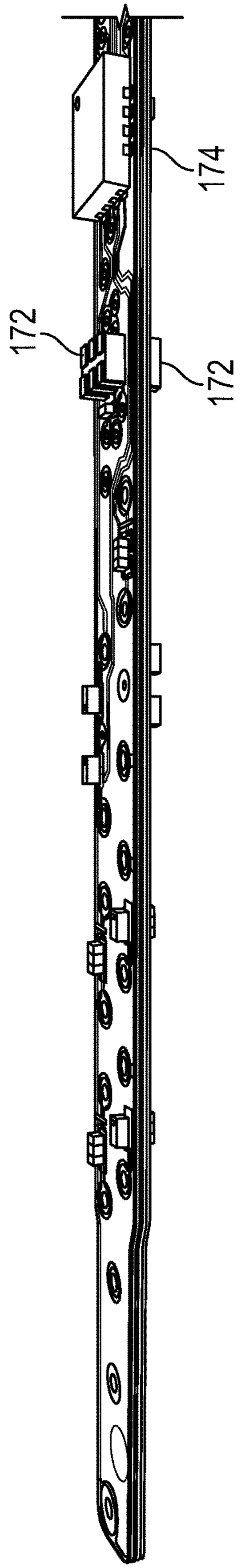
FIG. 7.2

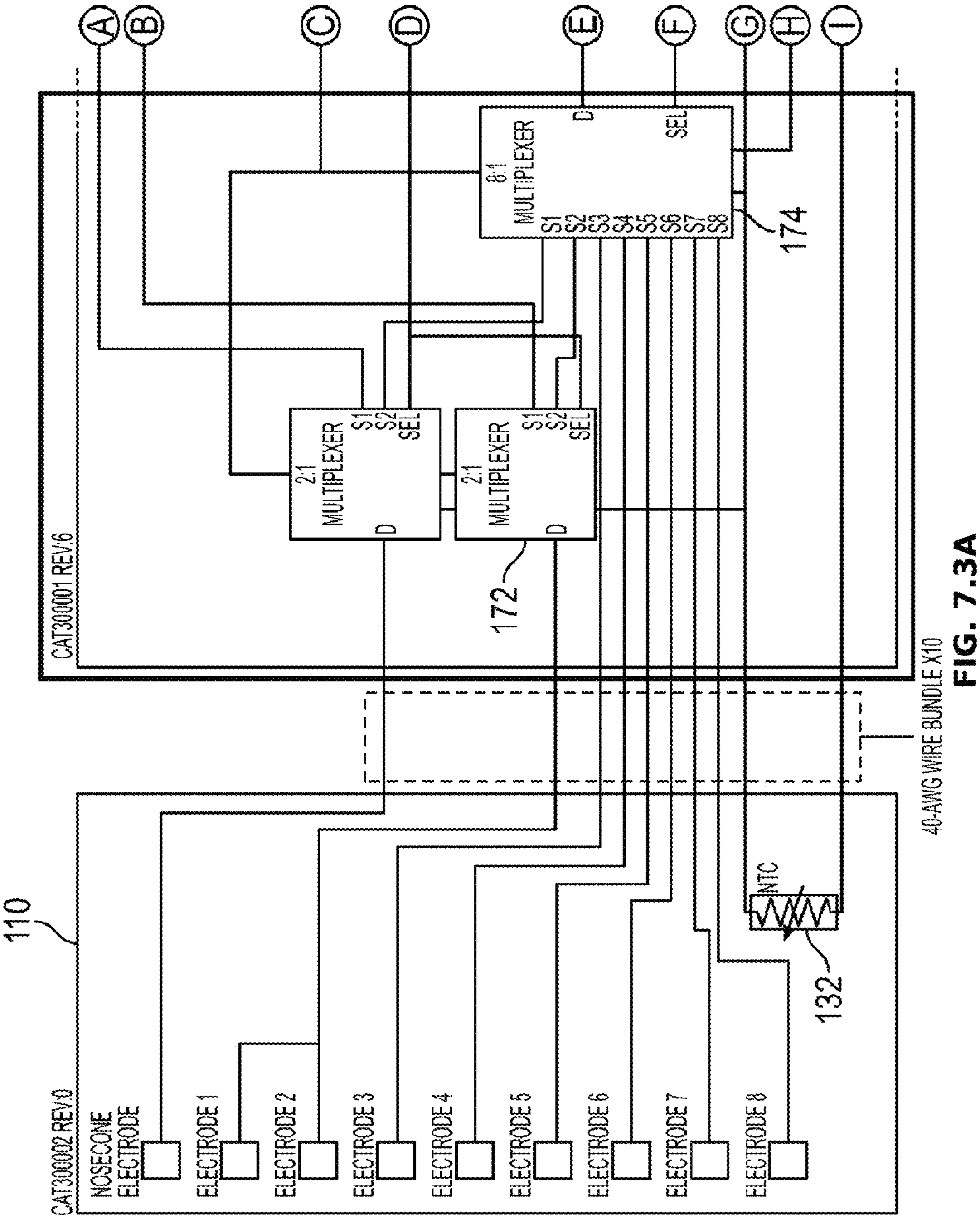
FIG. 7.3A

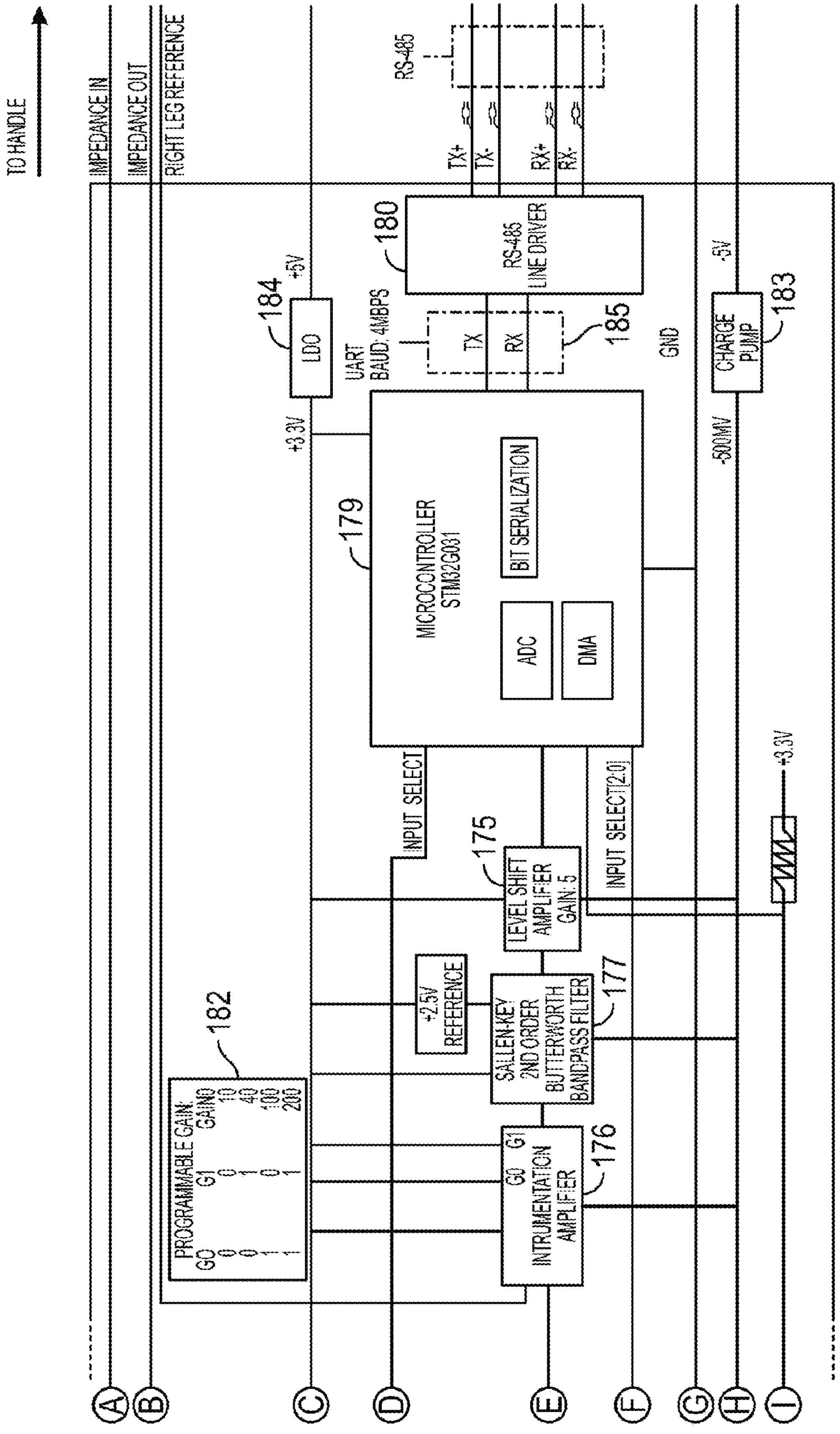
FIG. 7.3B

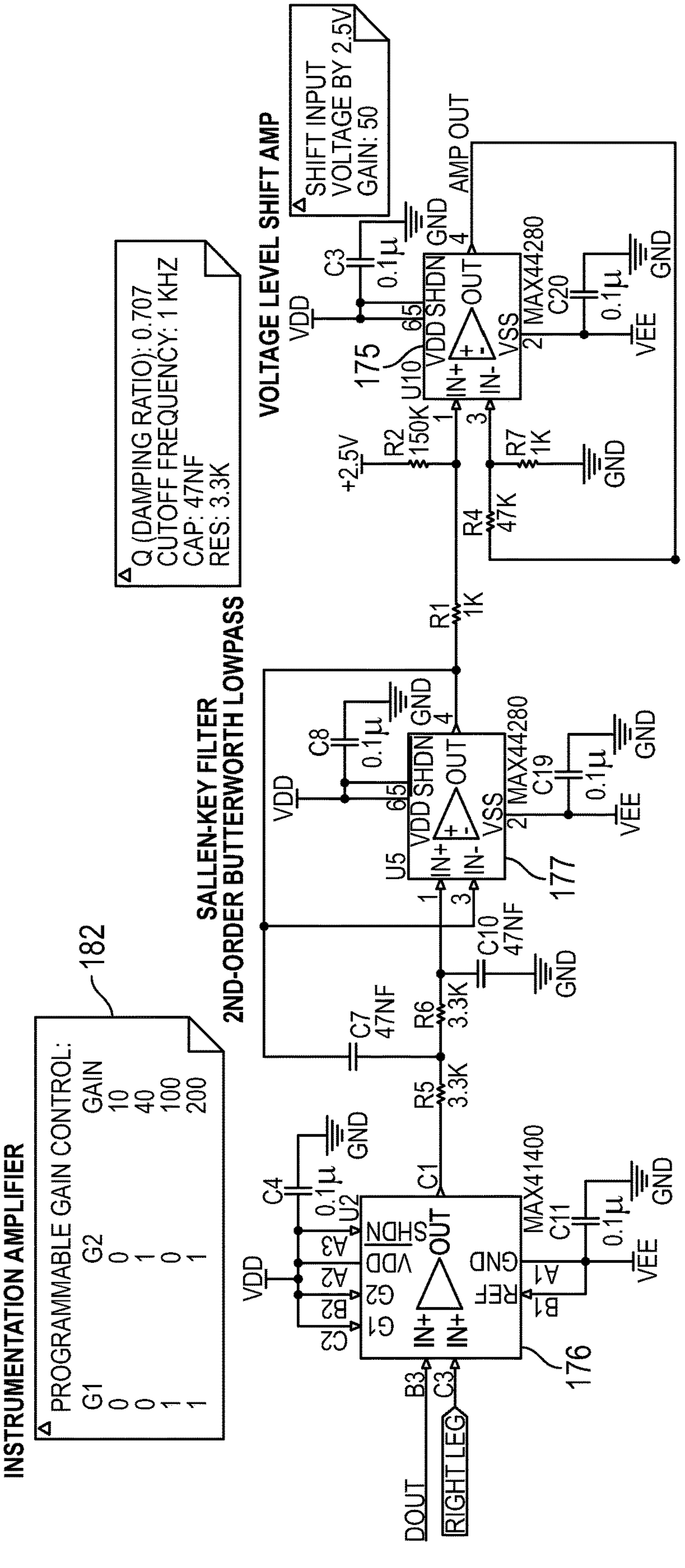
FIG. 8.1

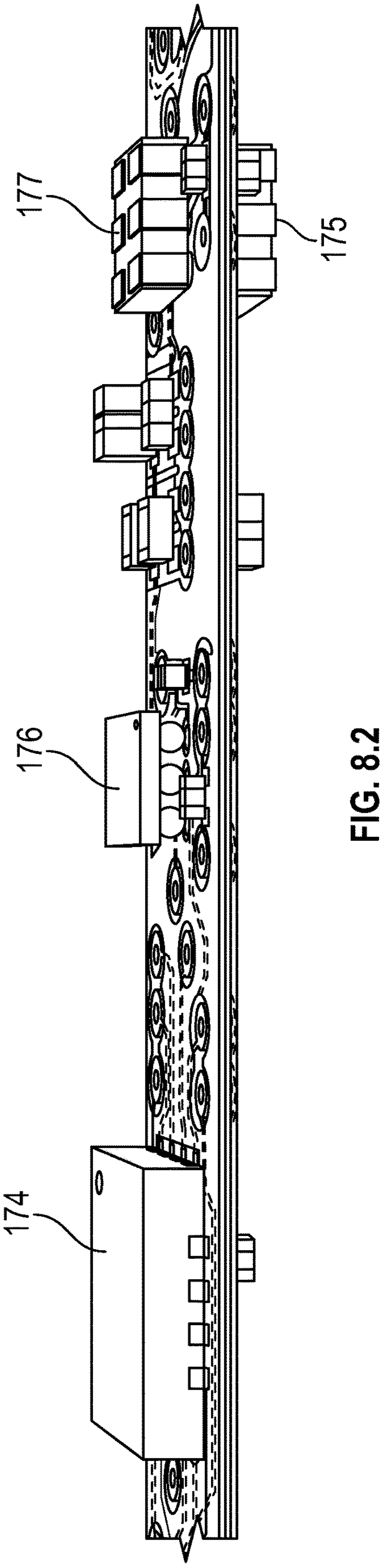
FIG. 8.2

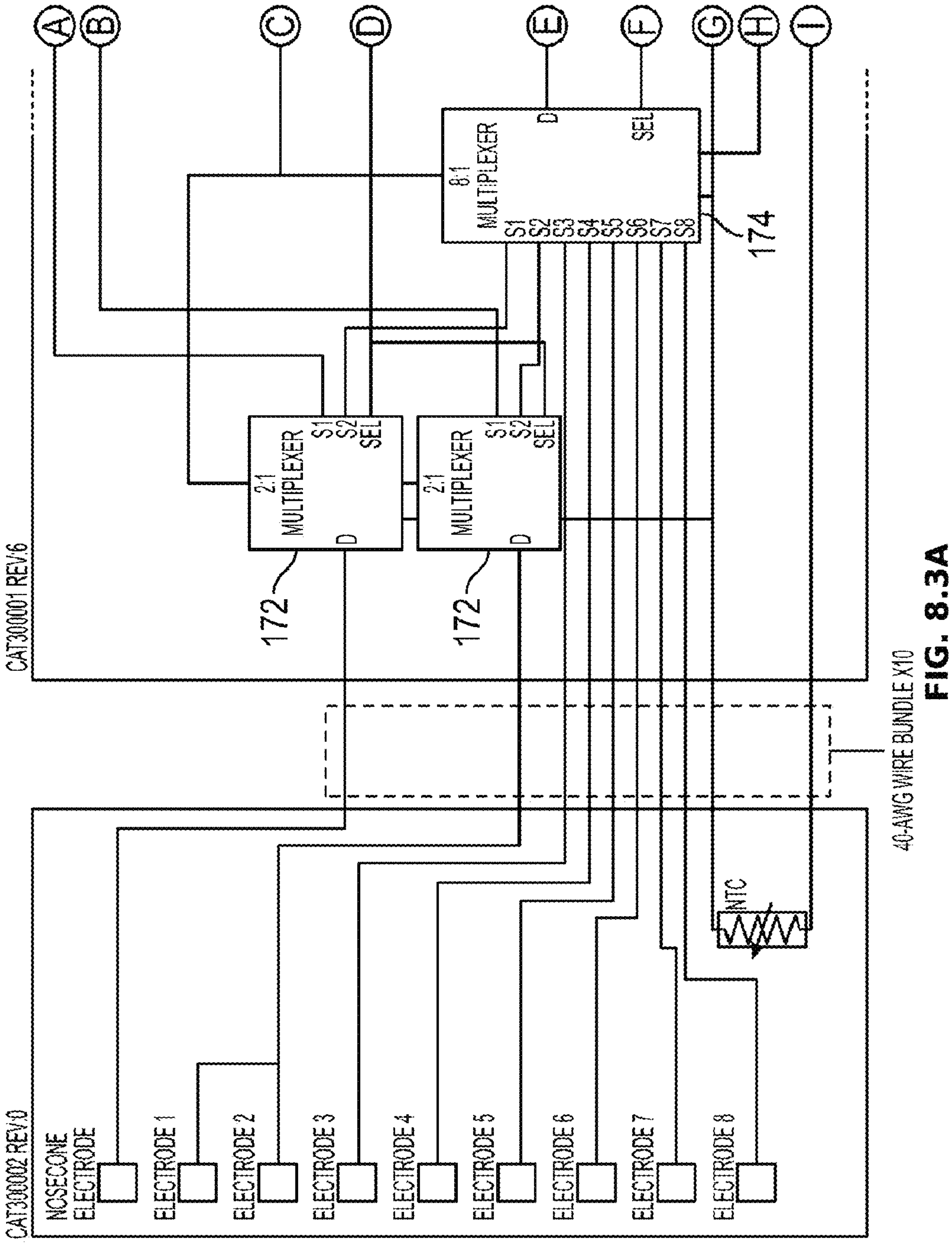
FIG. 8.3A

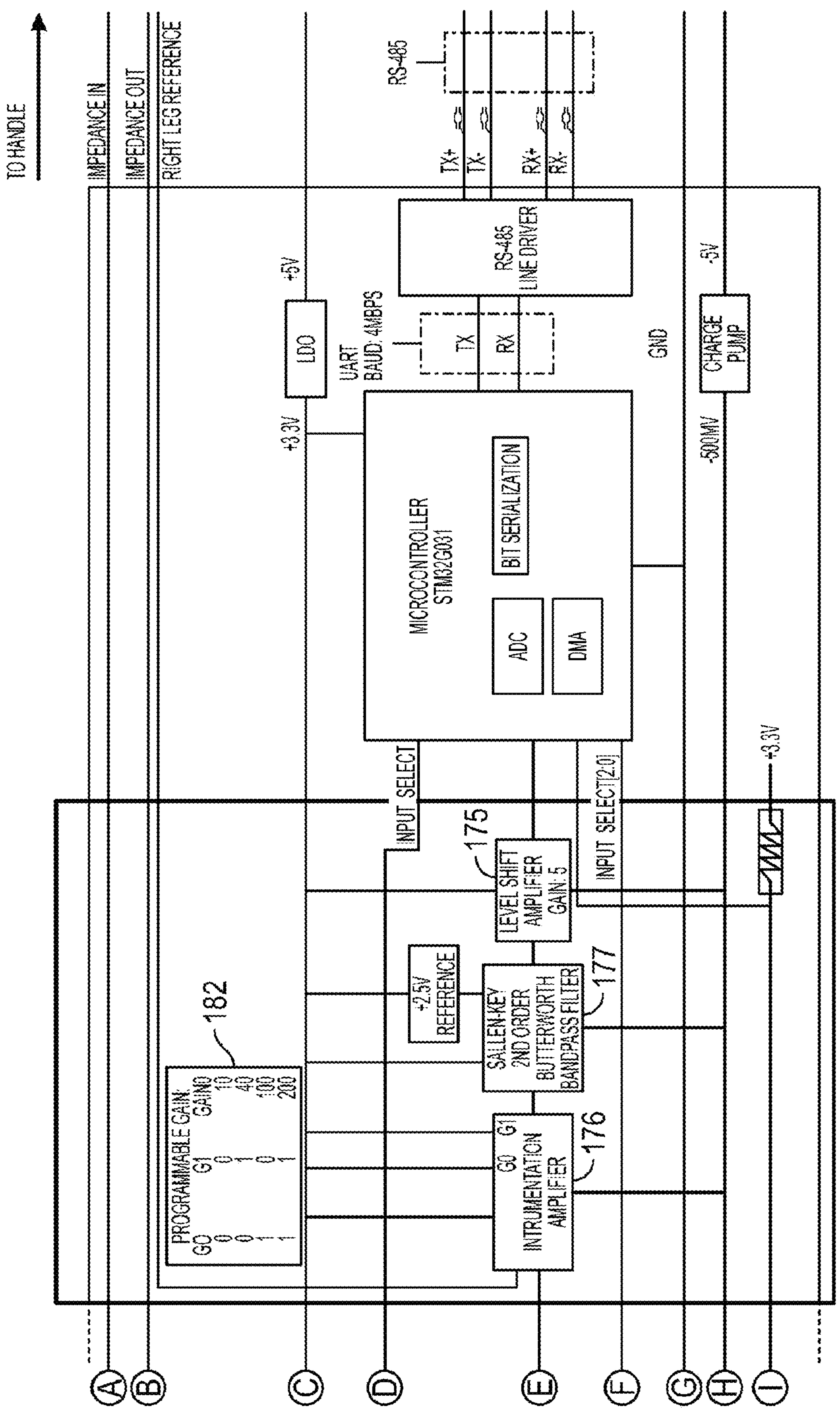
FIG. 8.3B

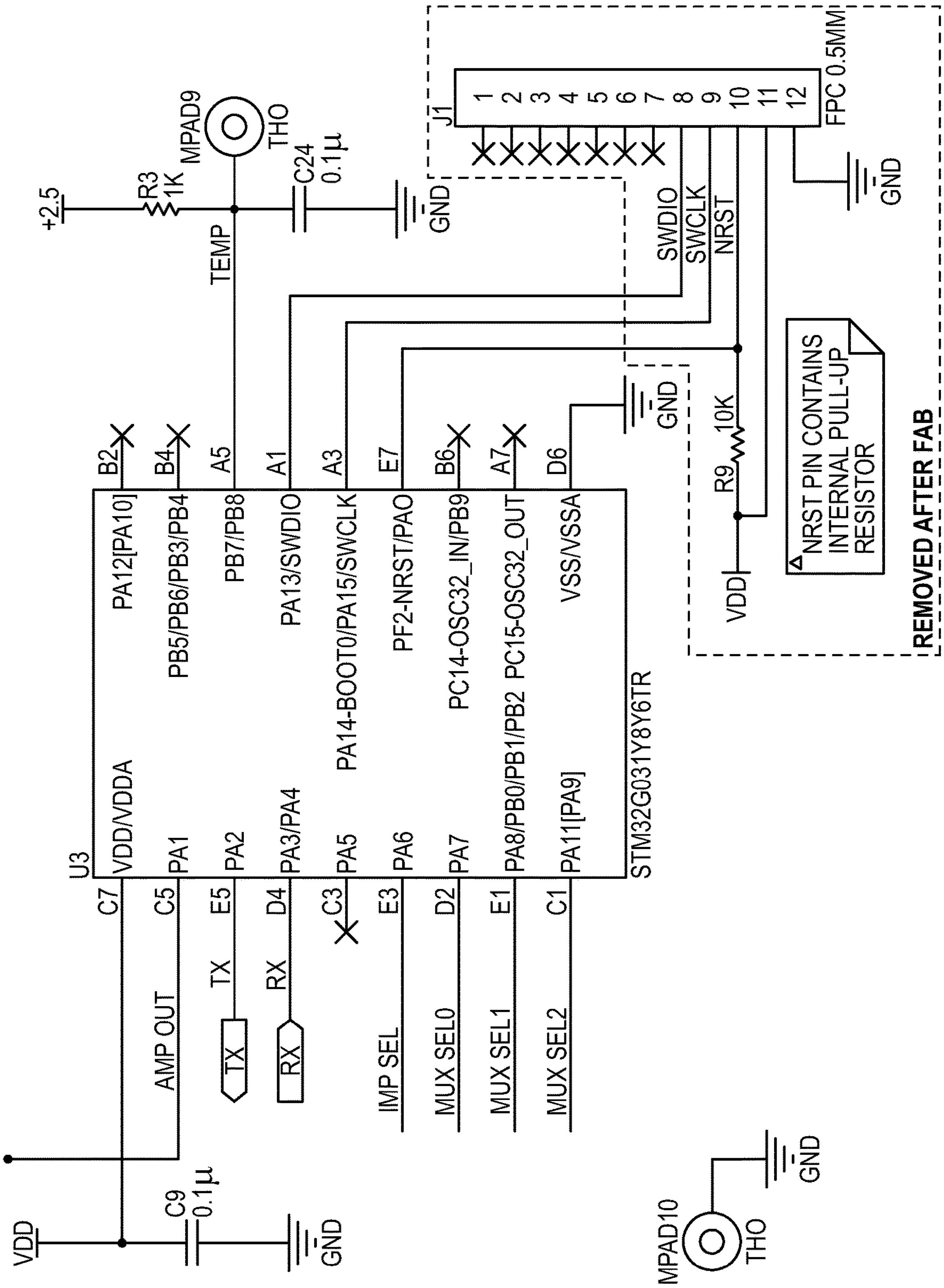
FIG. 9.1

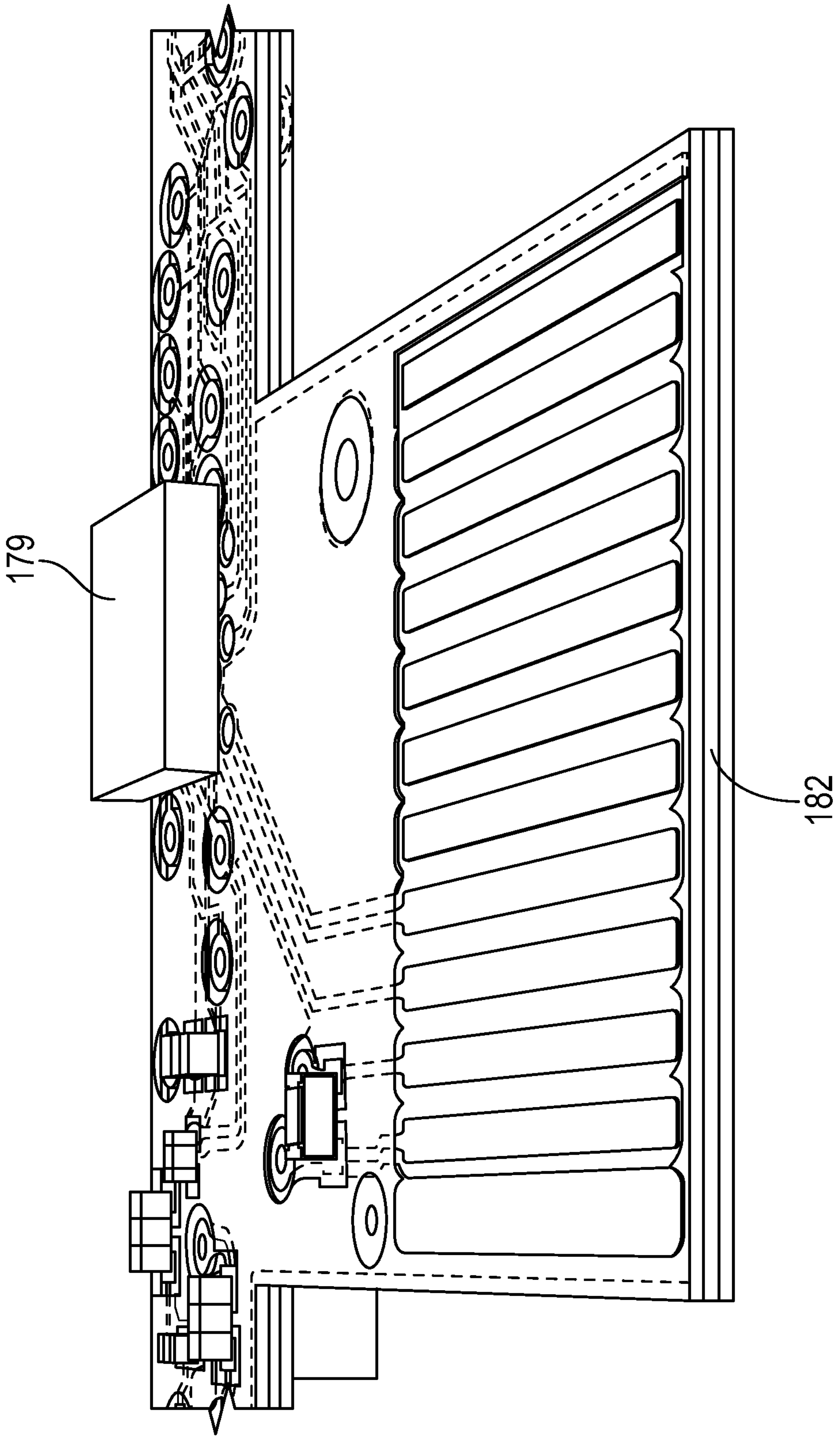
FIG. 9.2

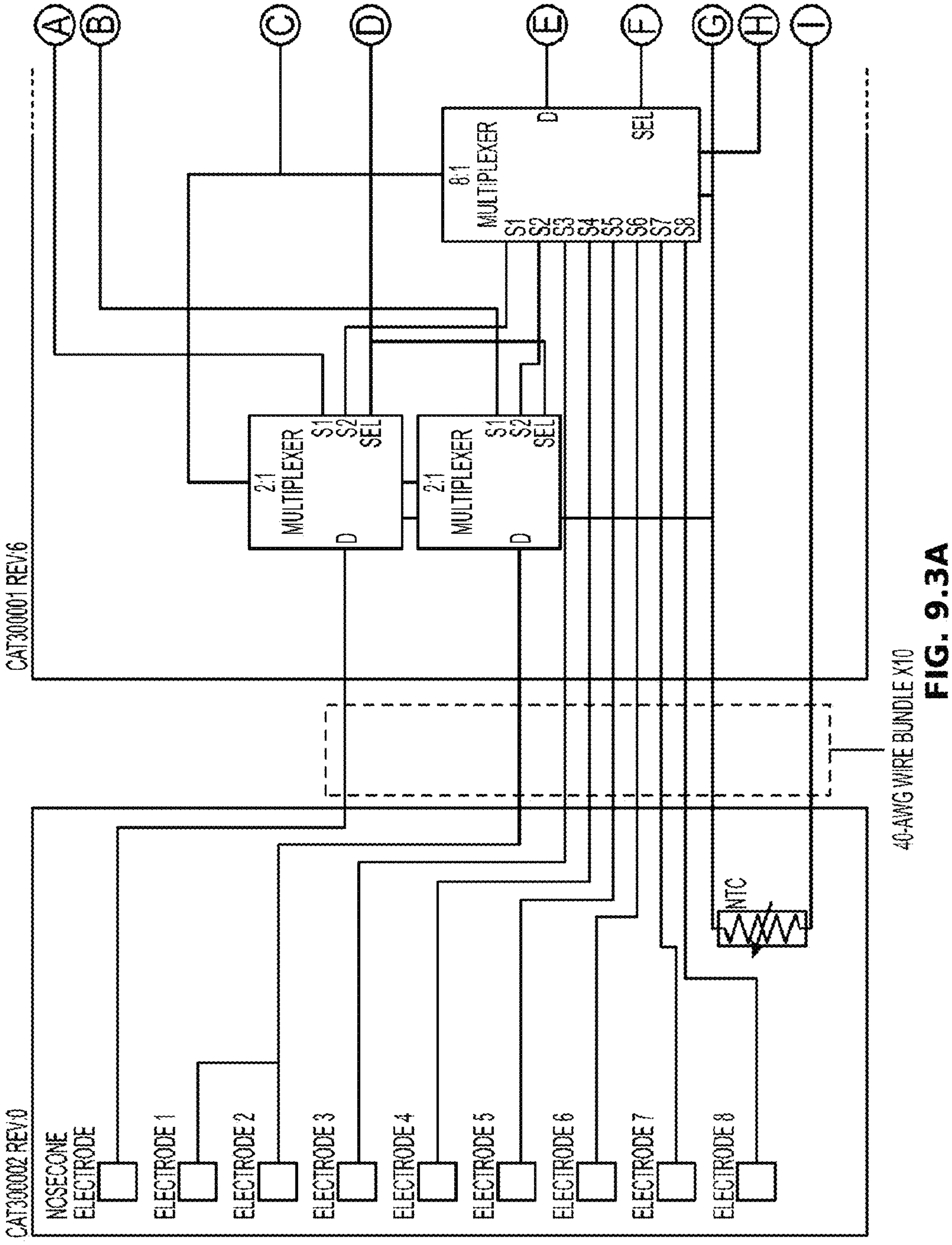
FIG. 9.3A

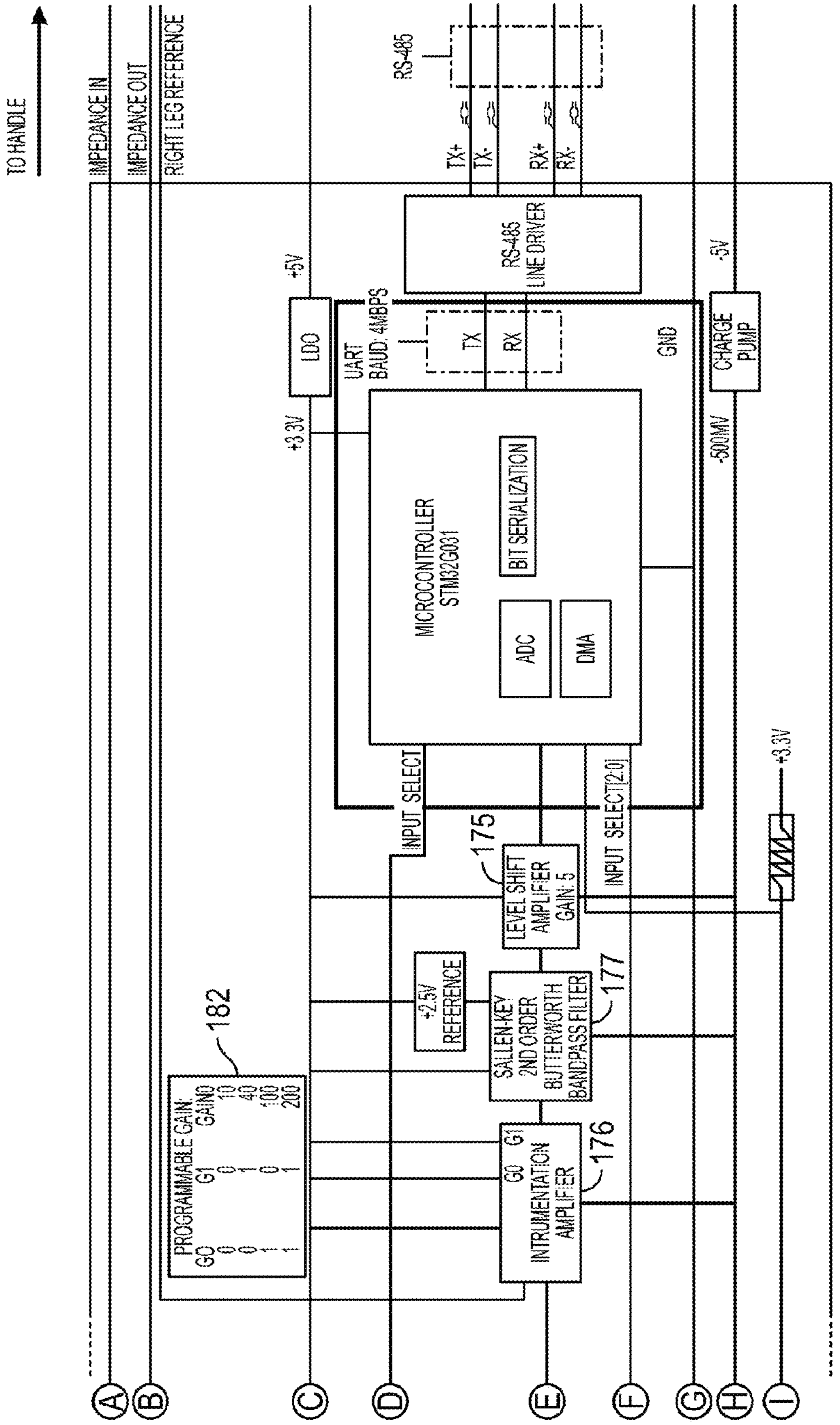
FIG. 9.3B

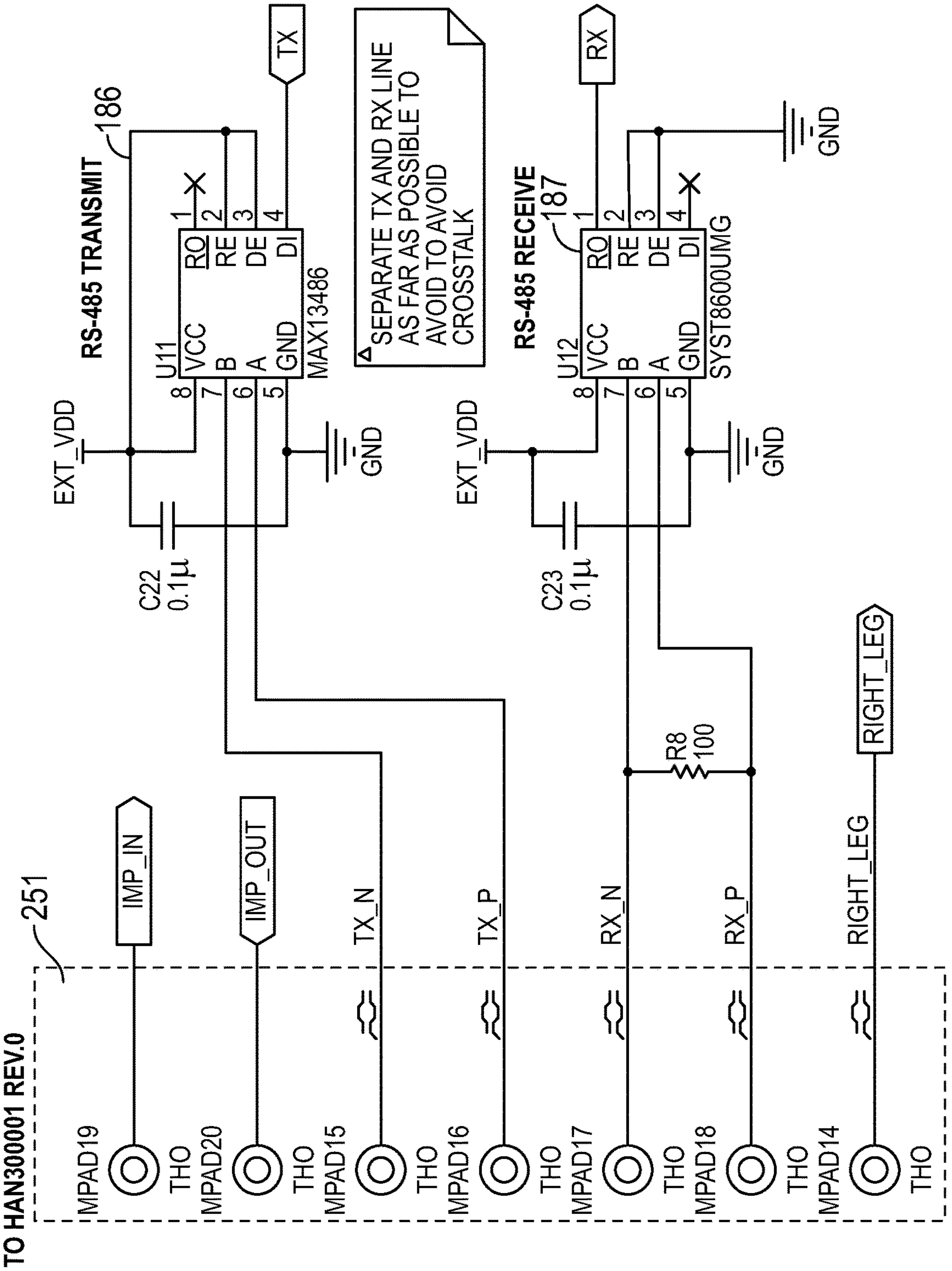
FIG. 10.1

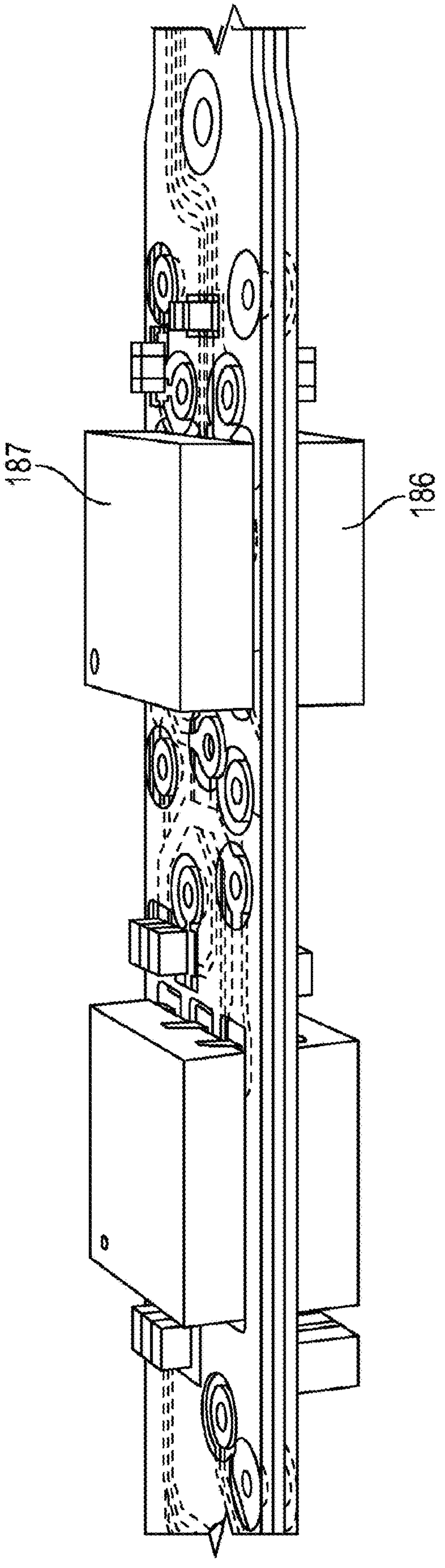
FIG. 10.2

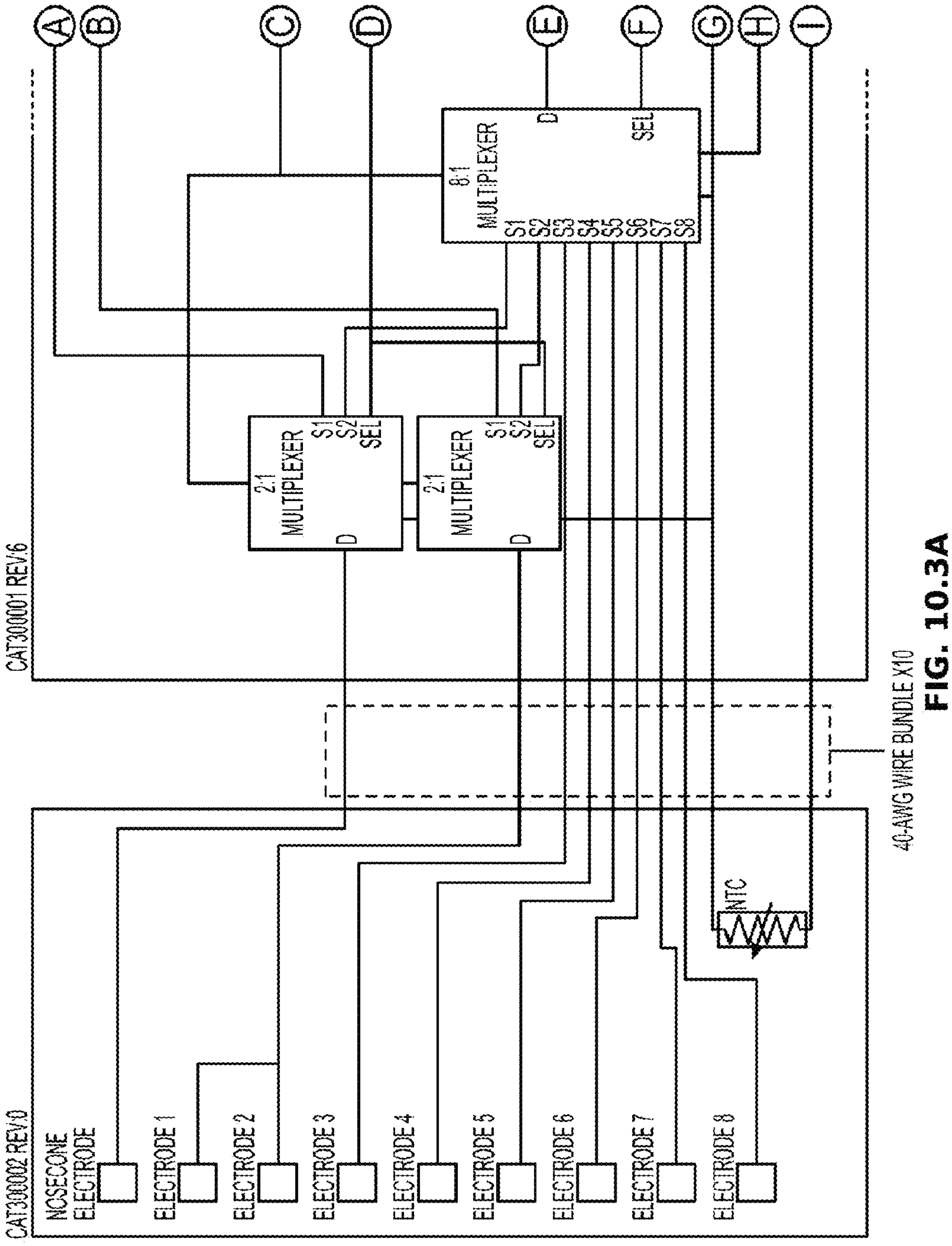
FIG. 10.3A

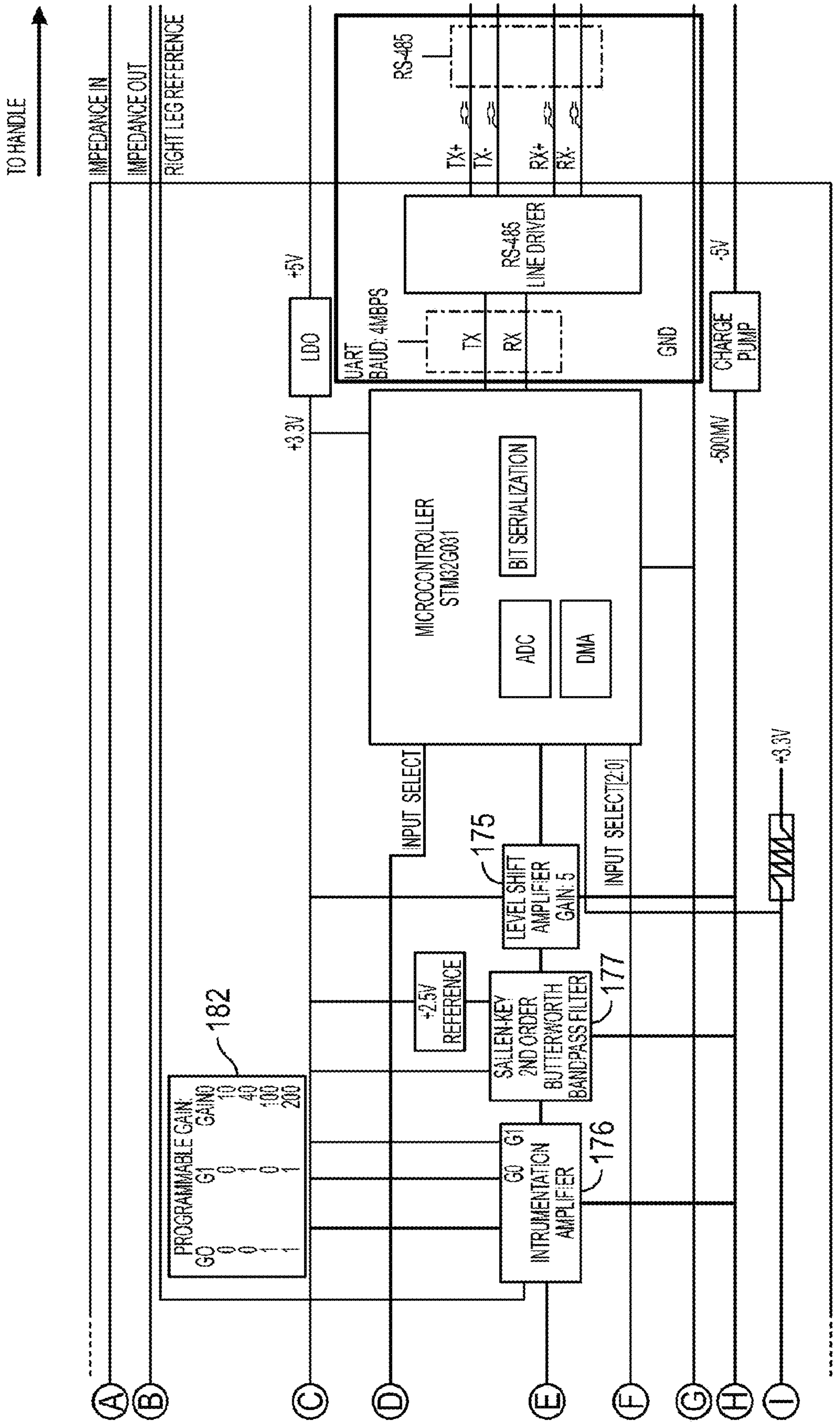
FIG. 10.3B

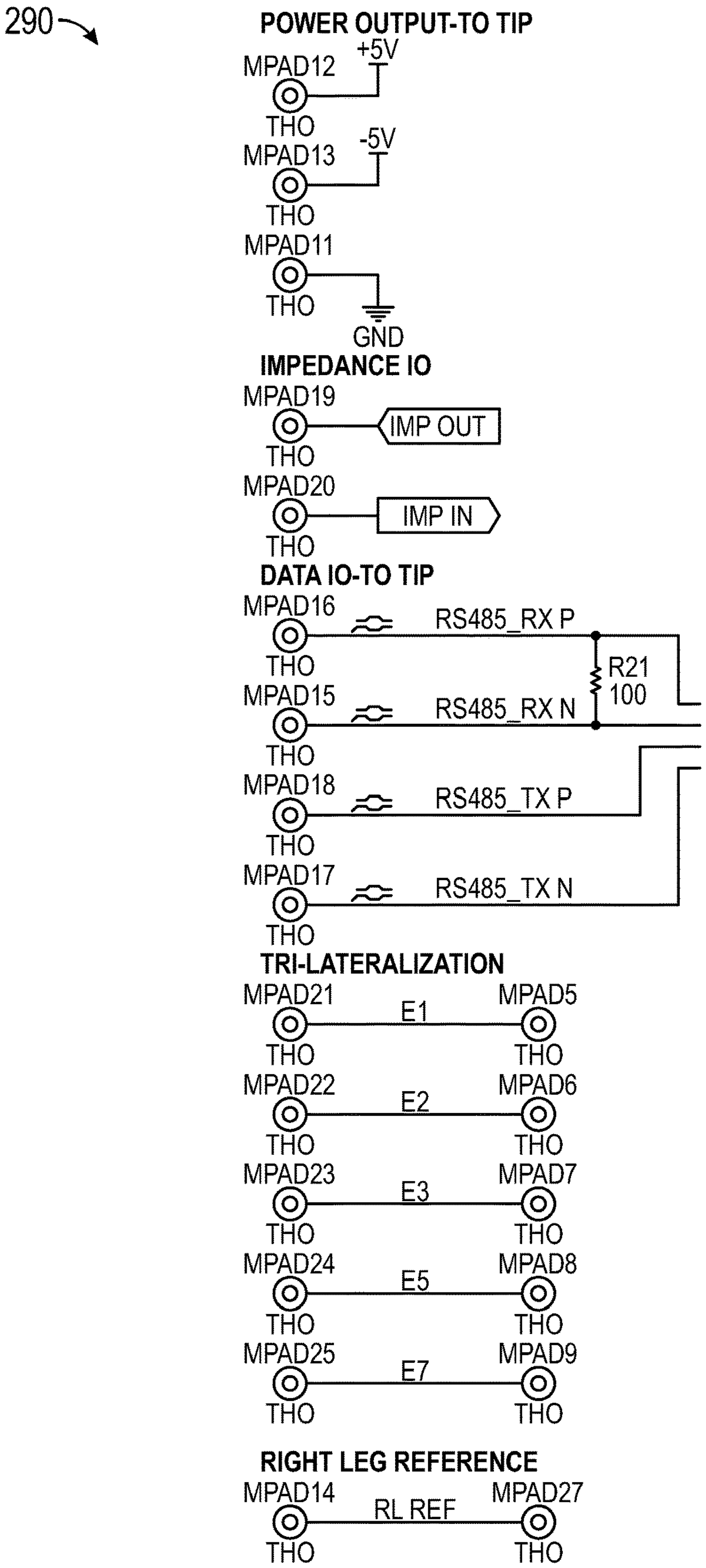
FIG. 11.1

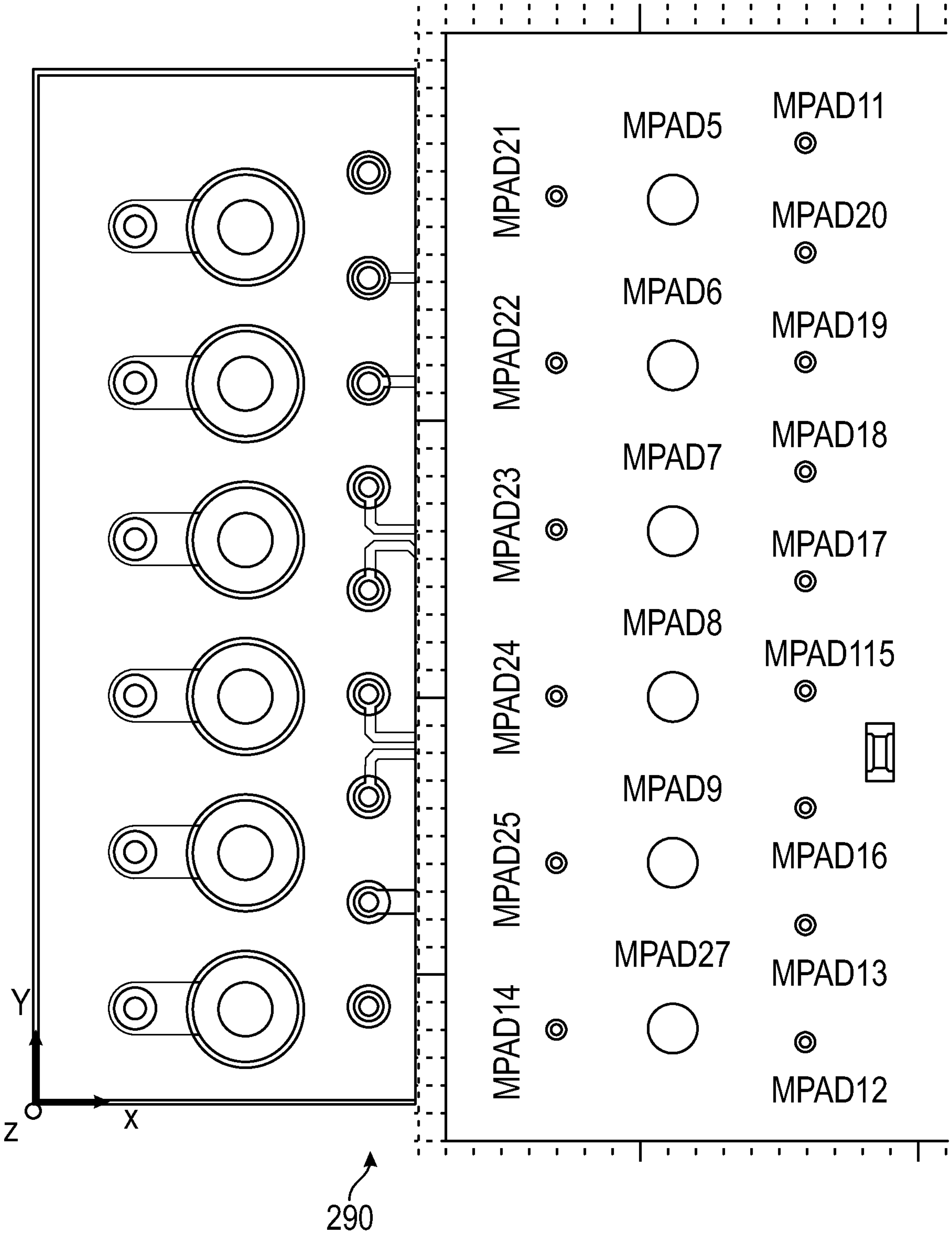
FIG. 11.2

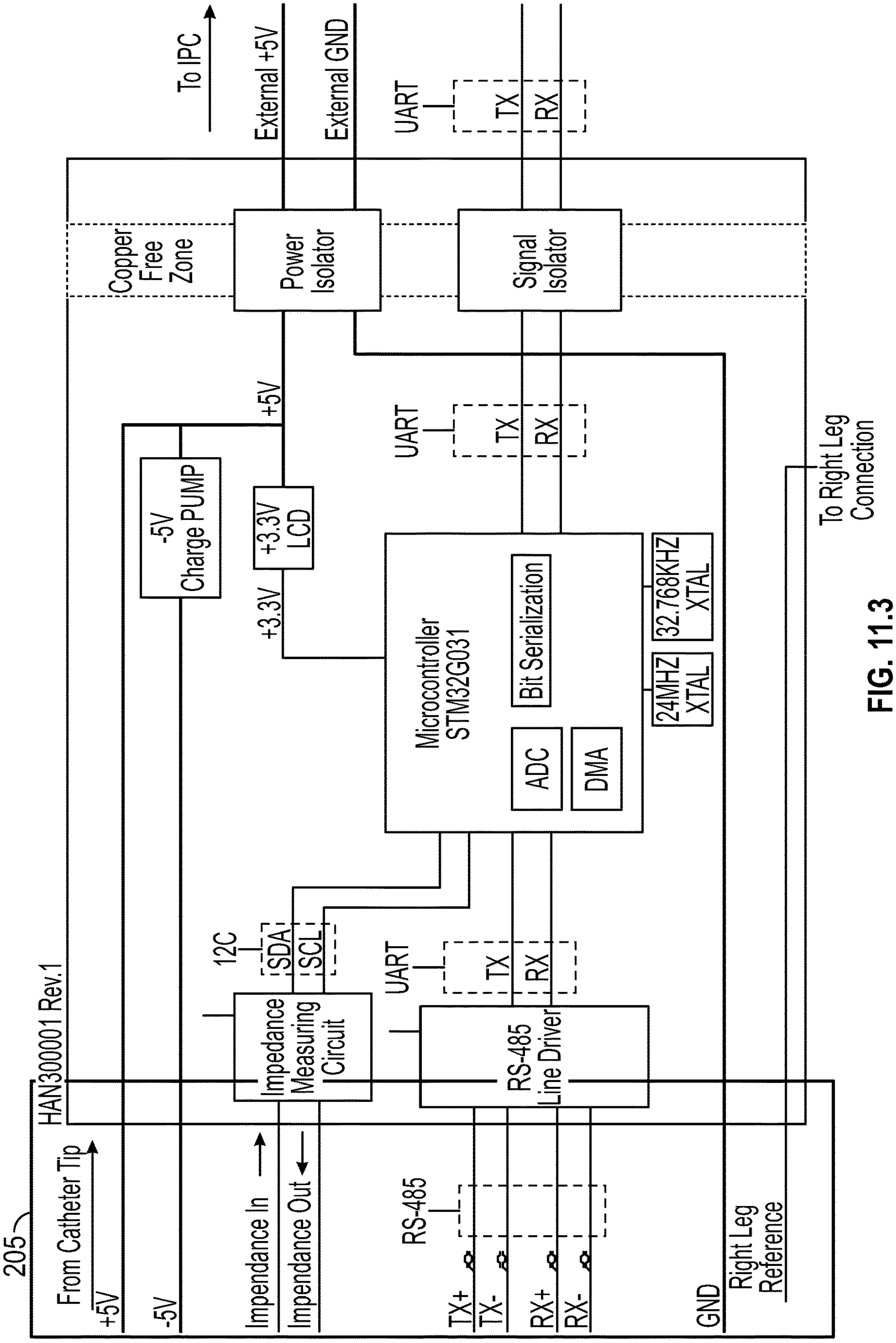
FIG. 11.3

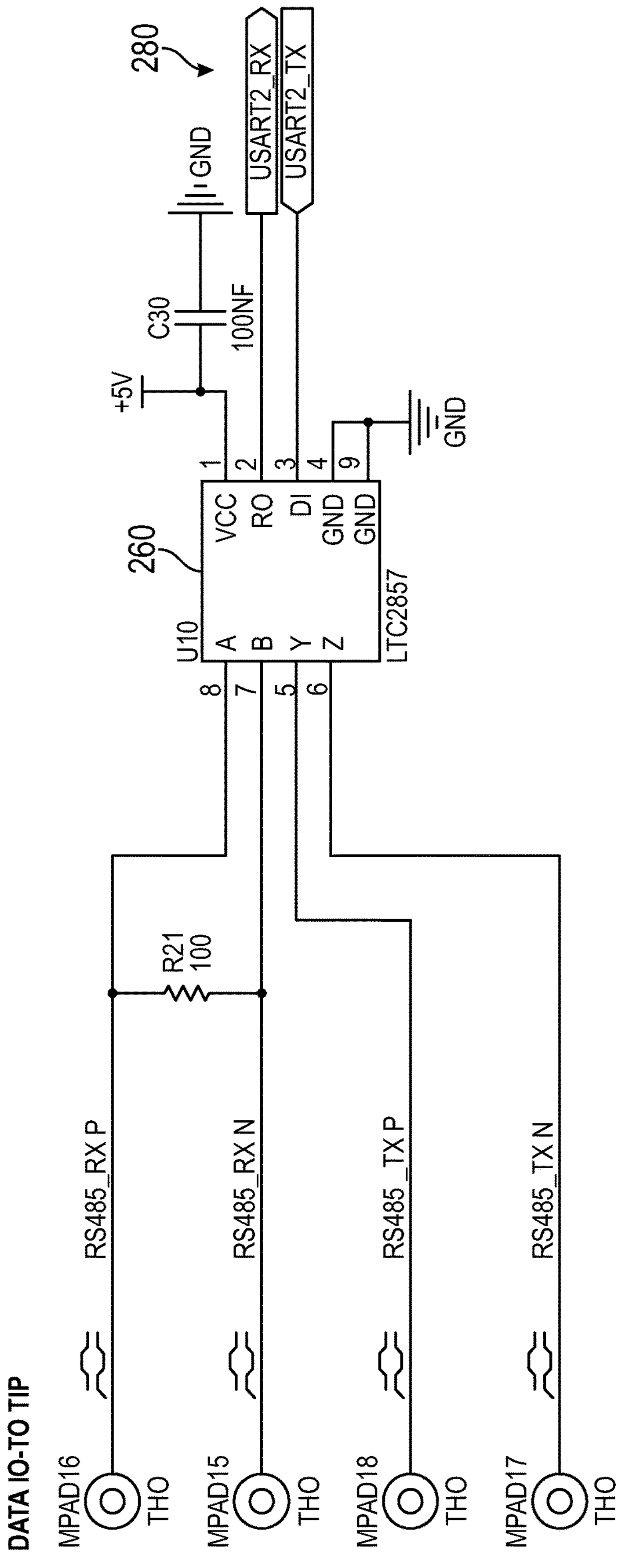
FIG. 12.1

FIG. 12.2
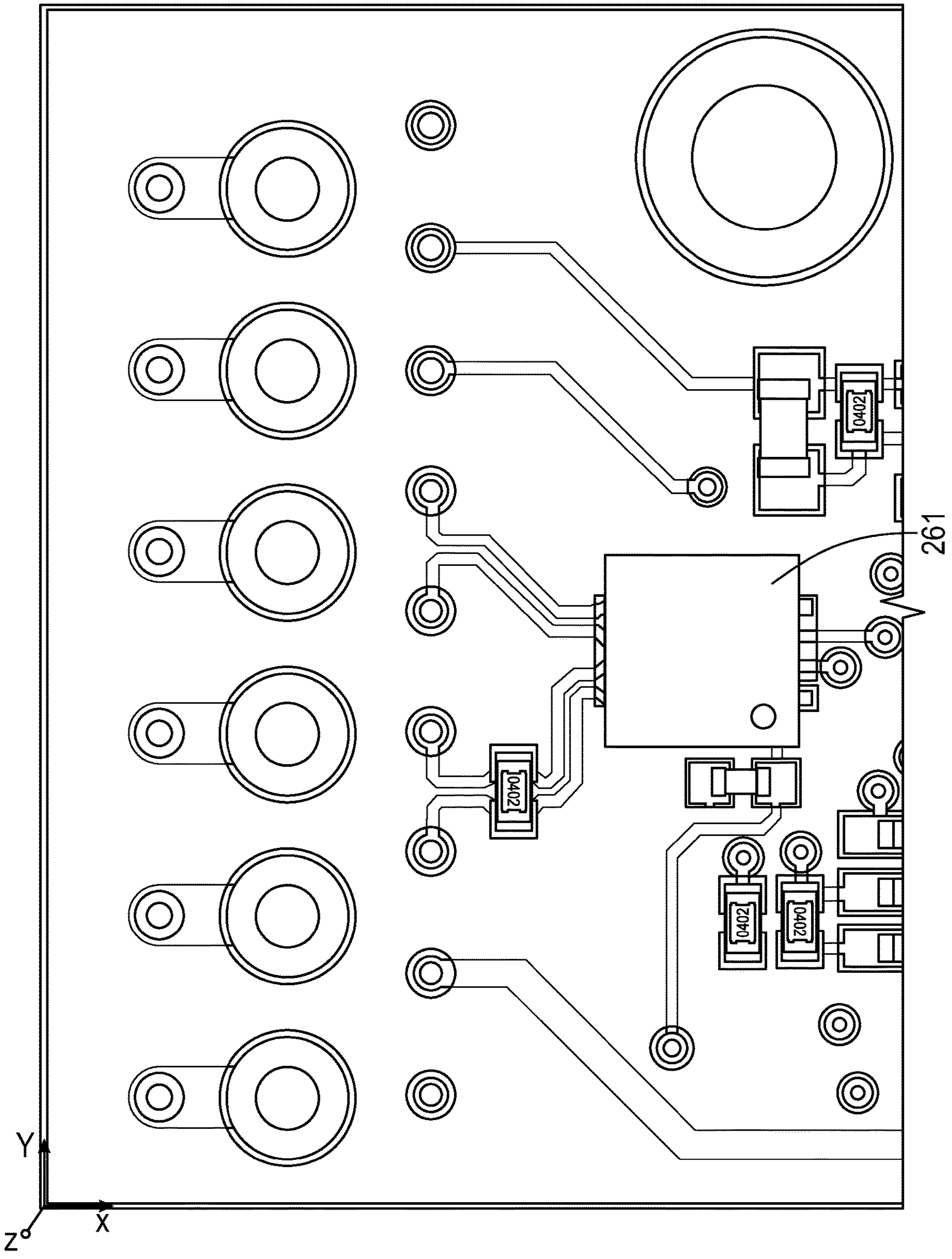

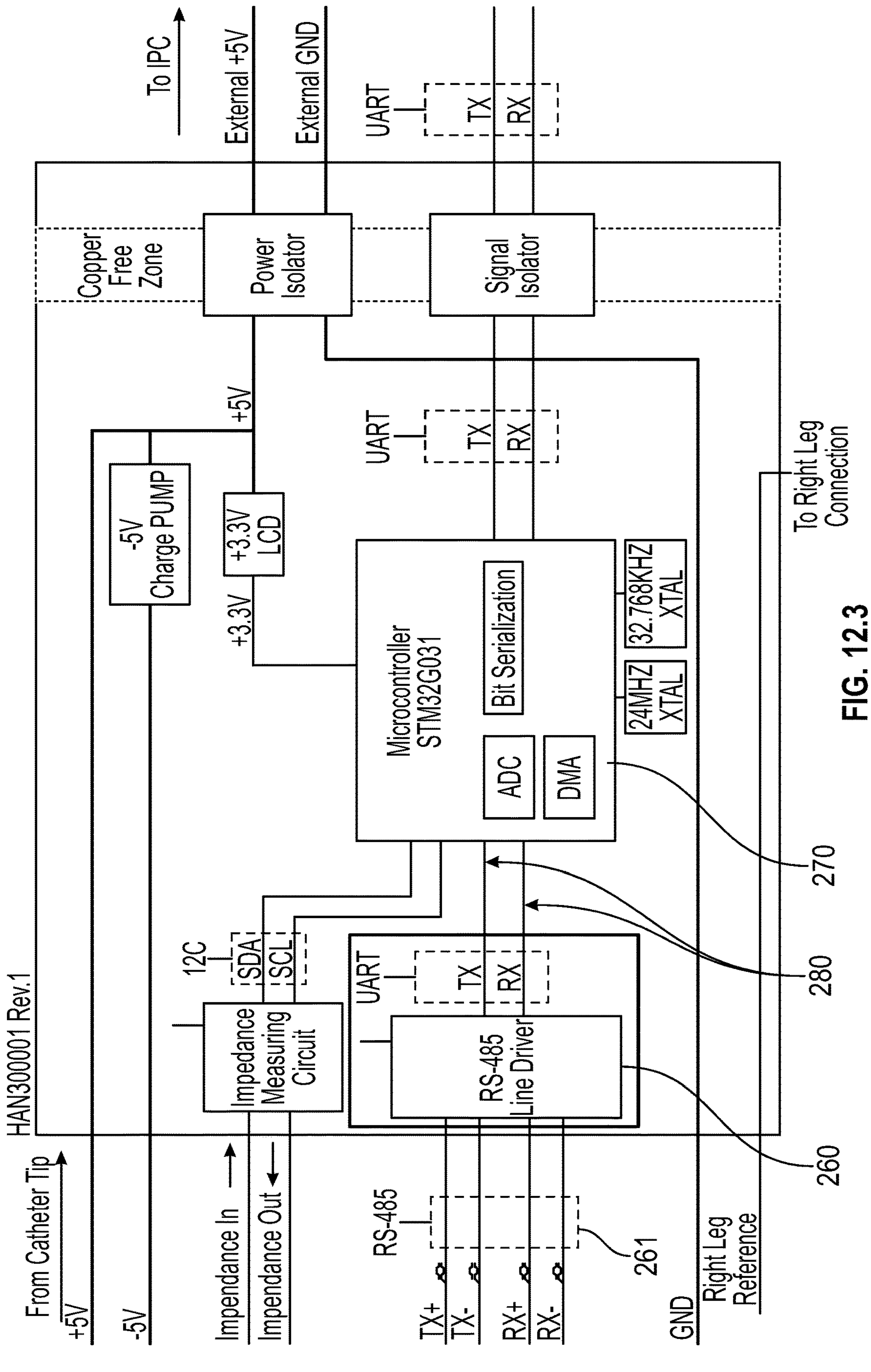
FIG. 12.3

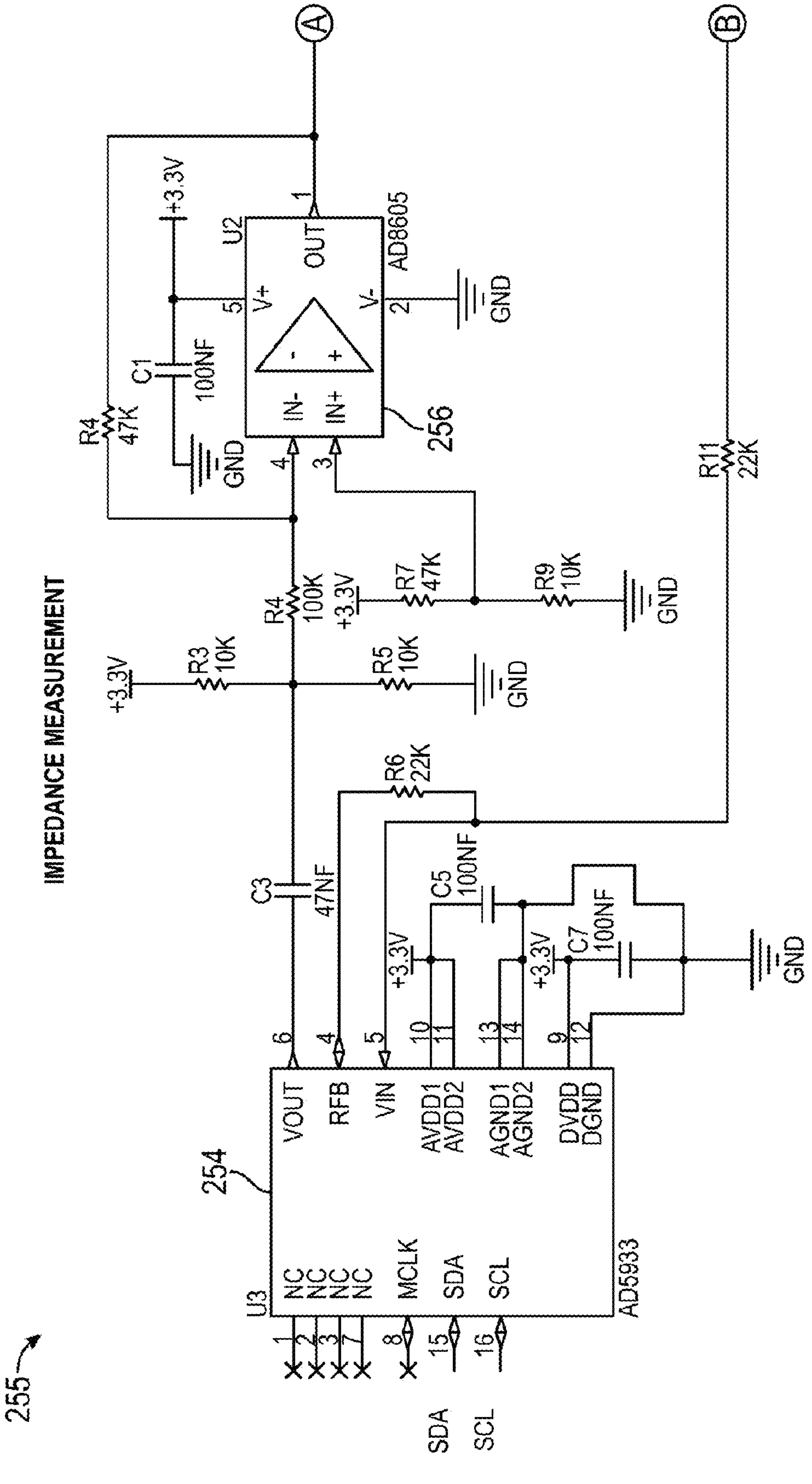
FIG. 13.1A

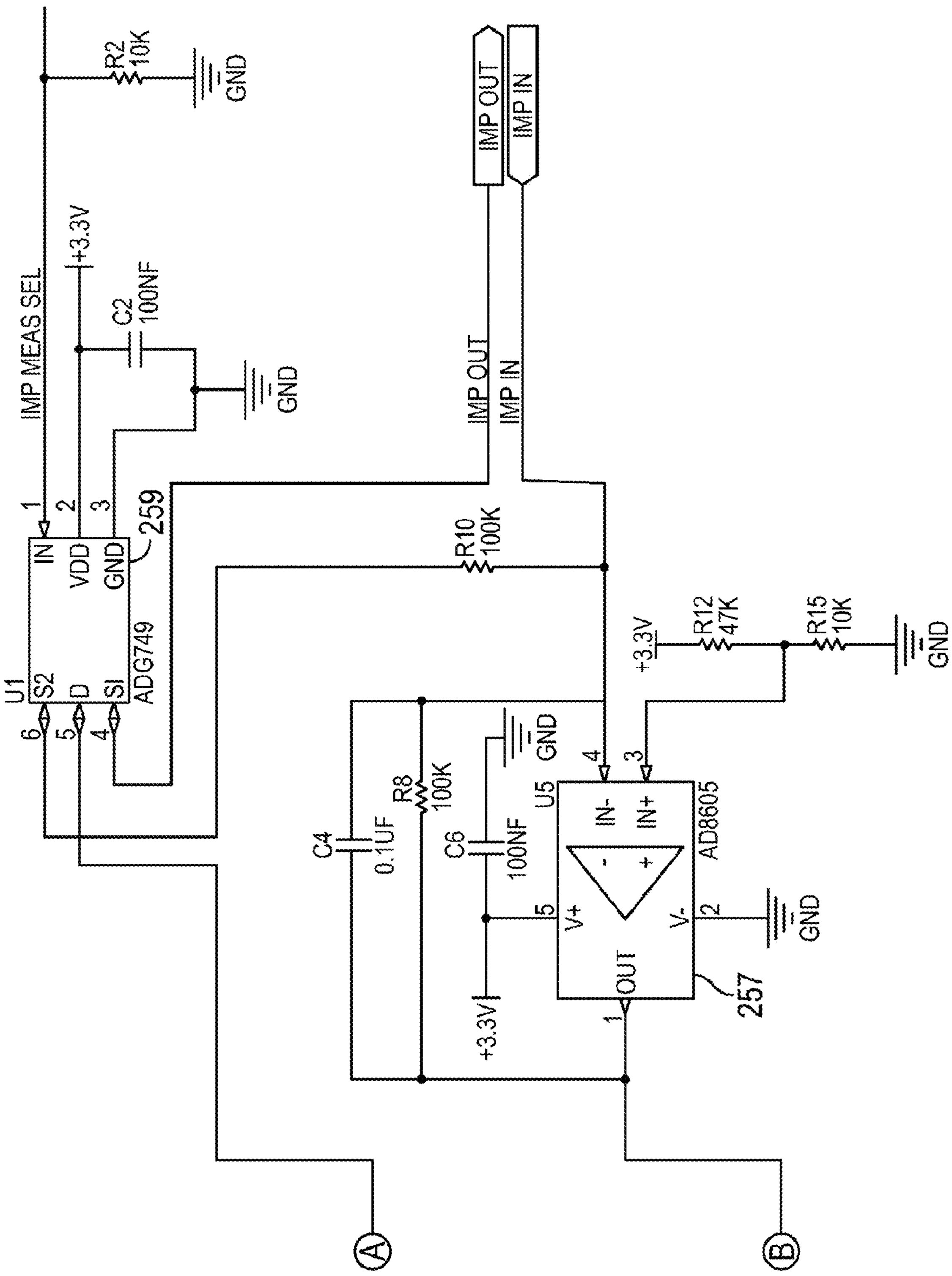
FIG. 13.1B

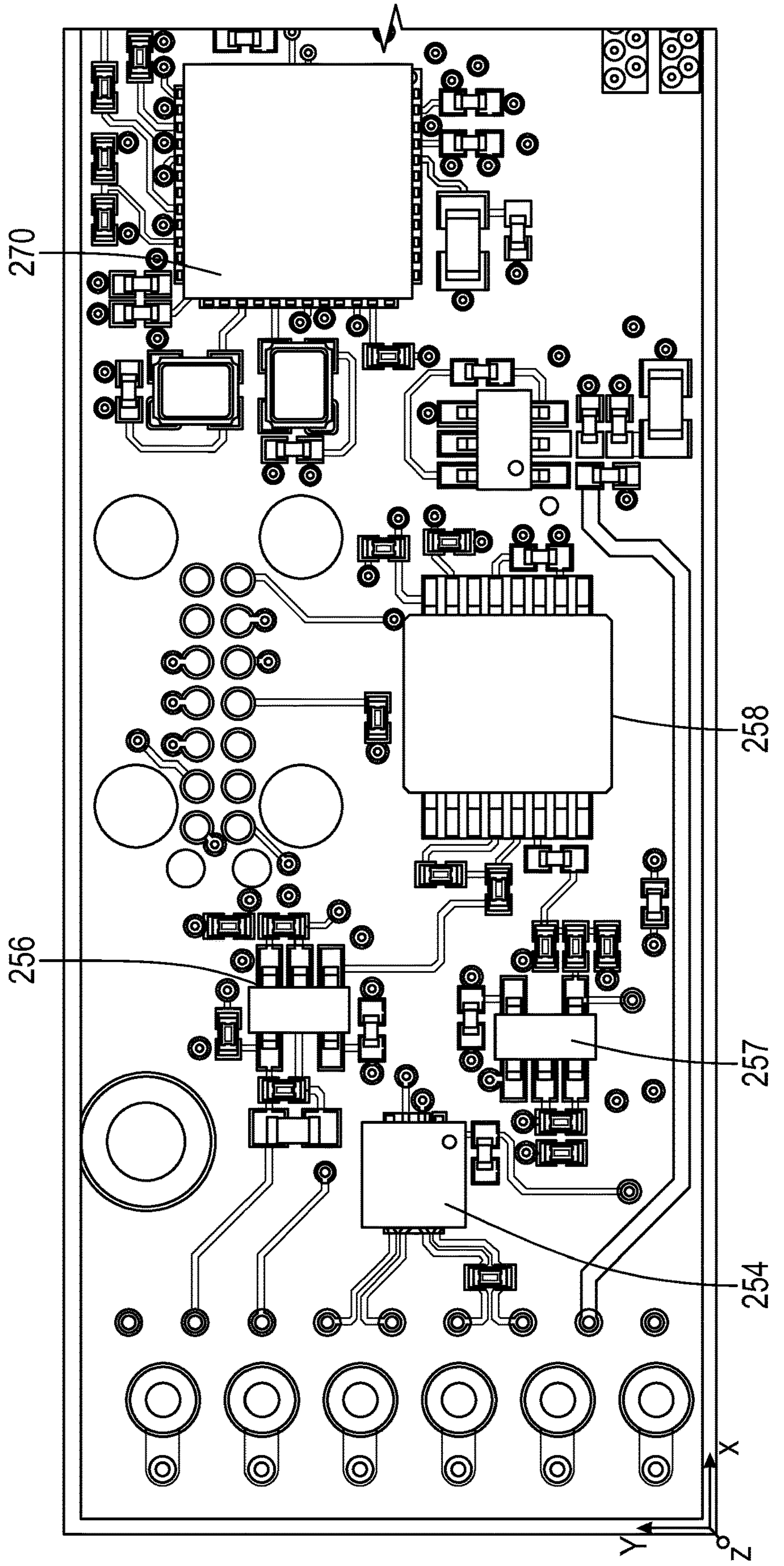
FIG. 13.2

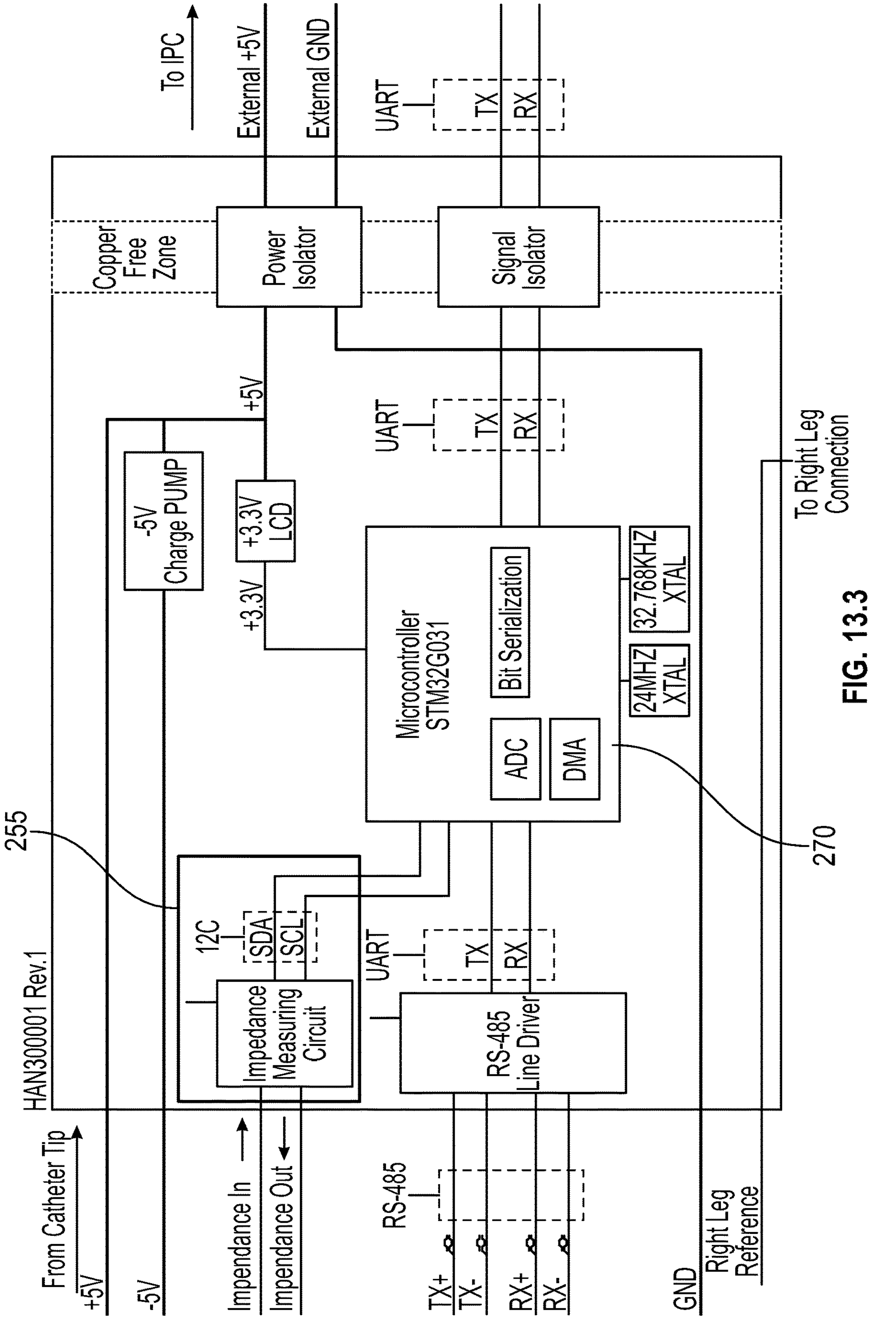
FIG. 13.3

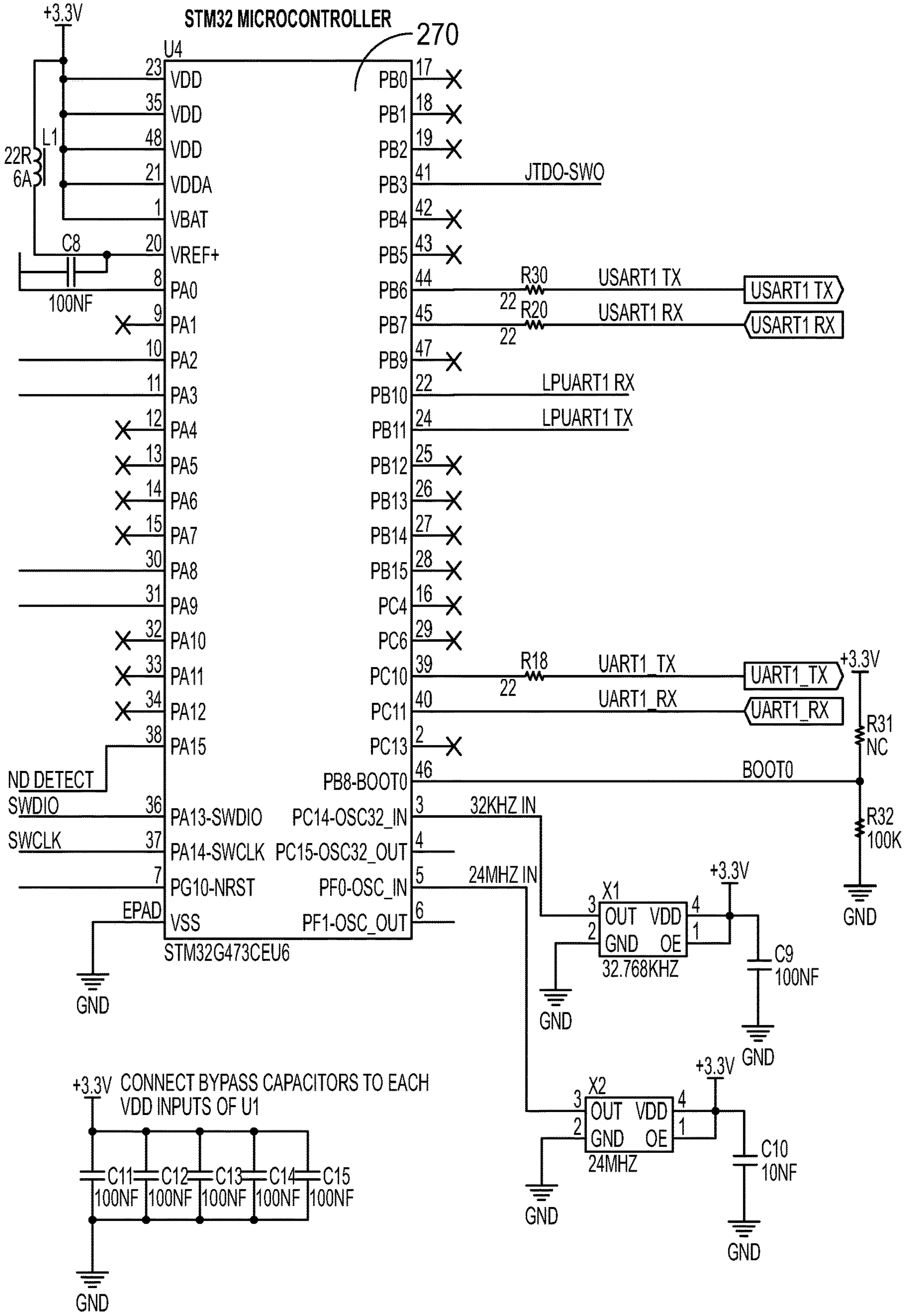
FIG. 14.1

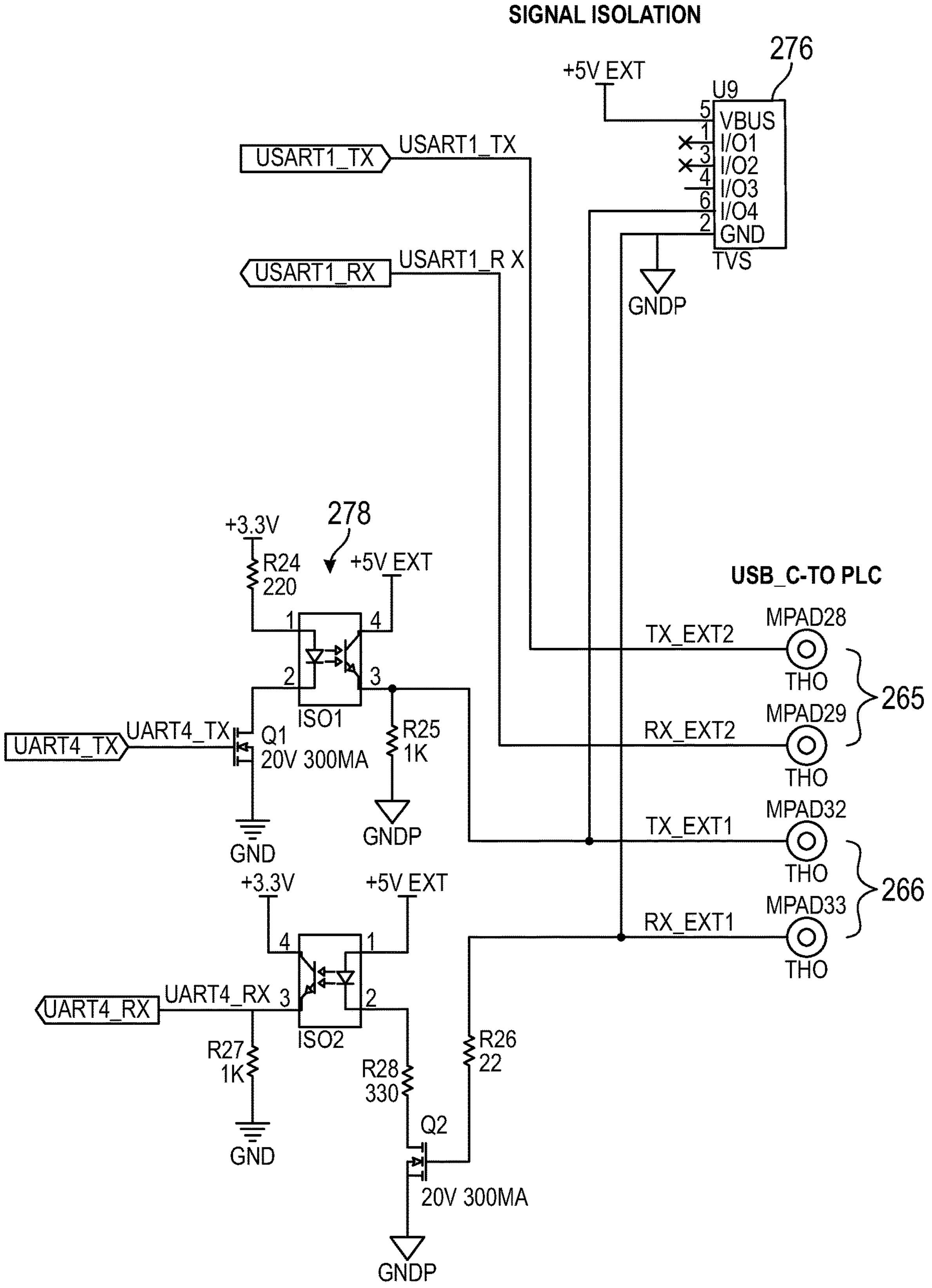
FIG. 14.2

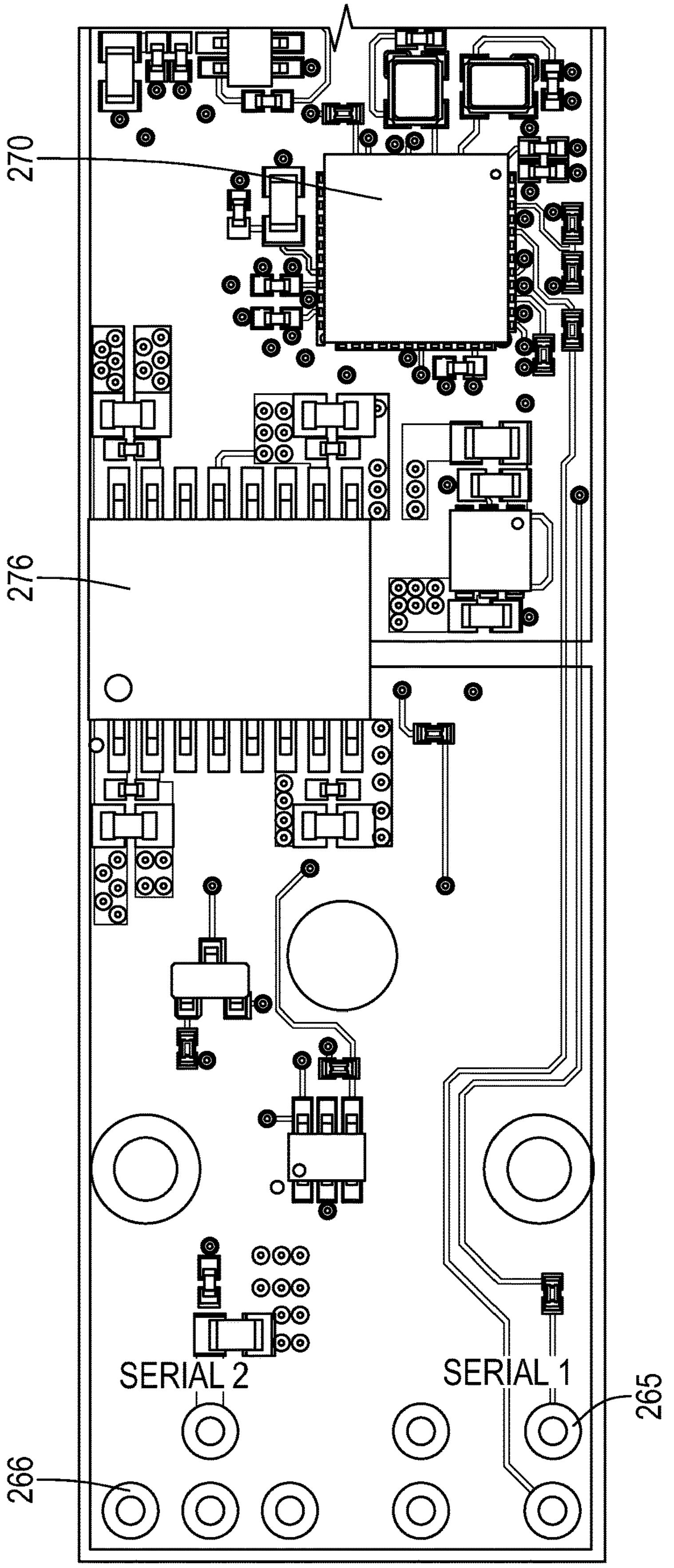
FIG. 14.3

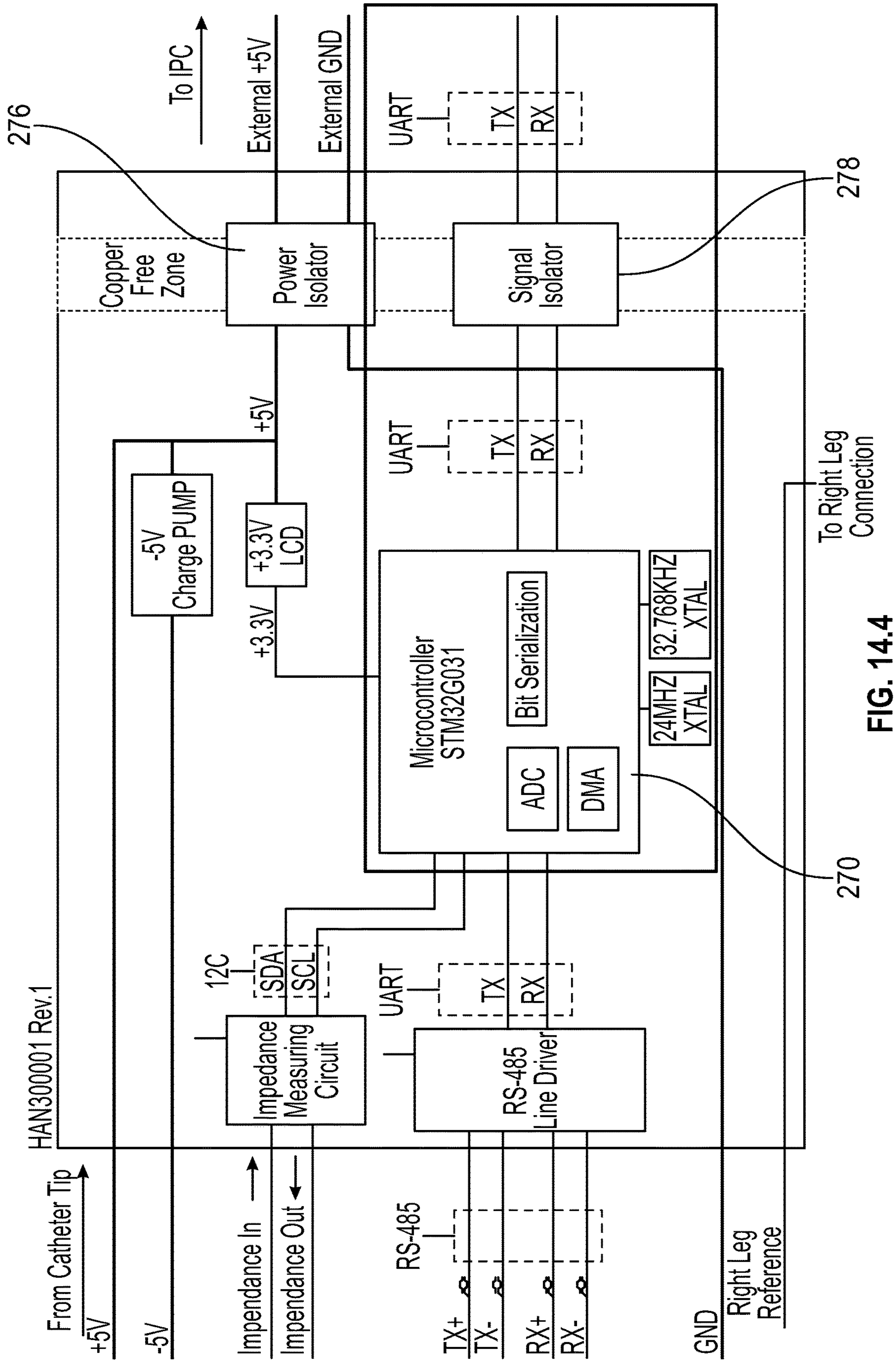
FIG. 14.4

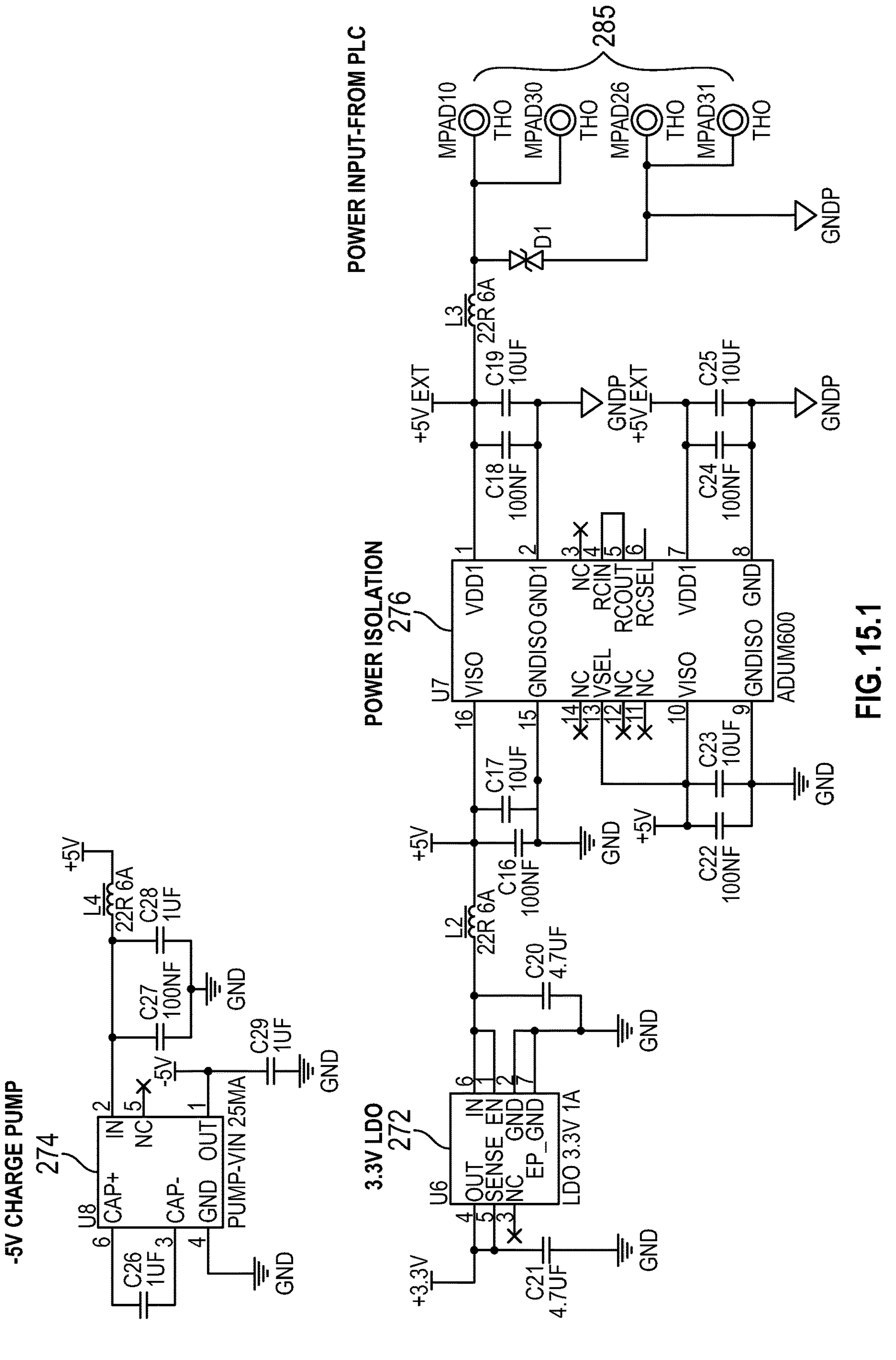
FIG. 15.1

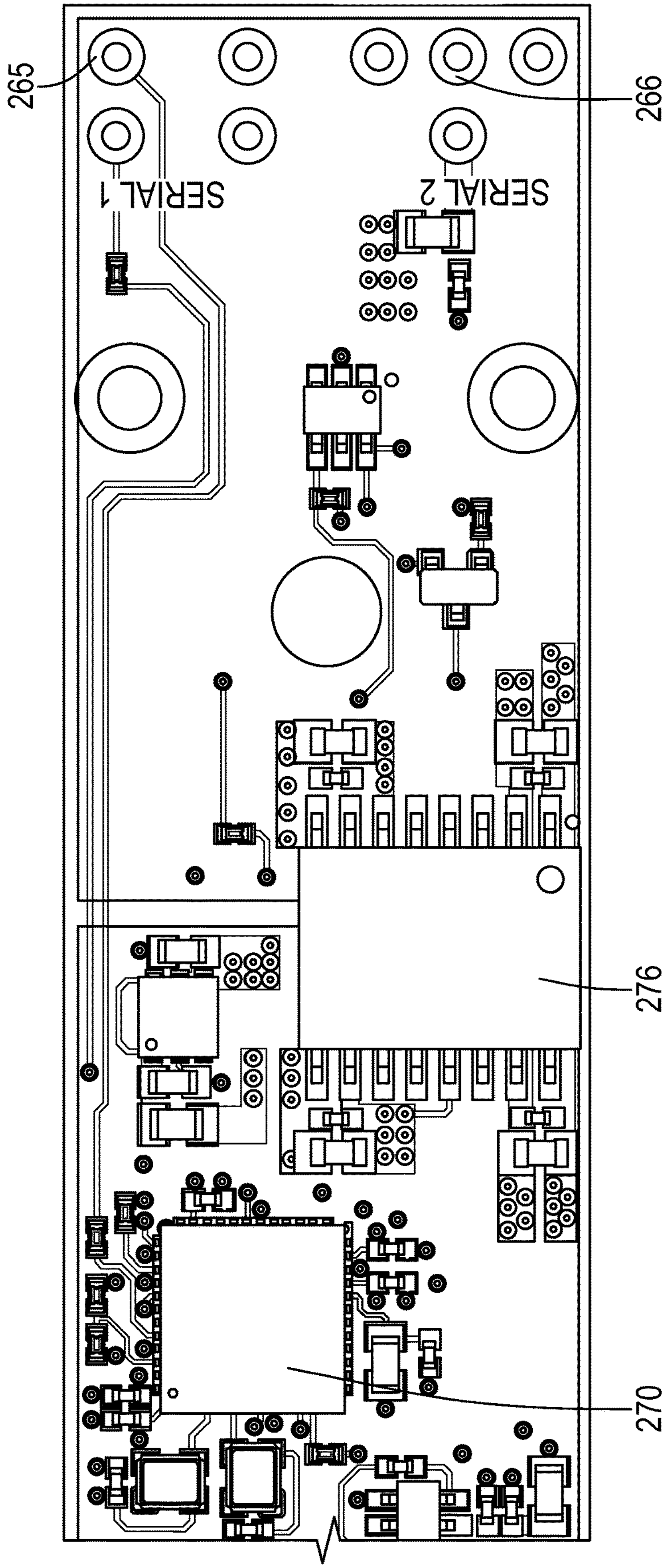
FIG. 15.2

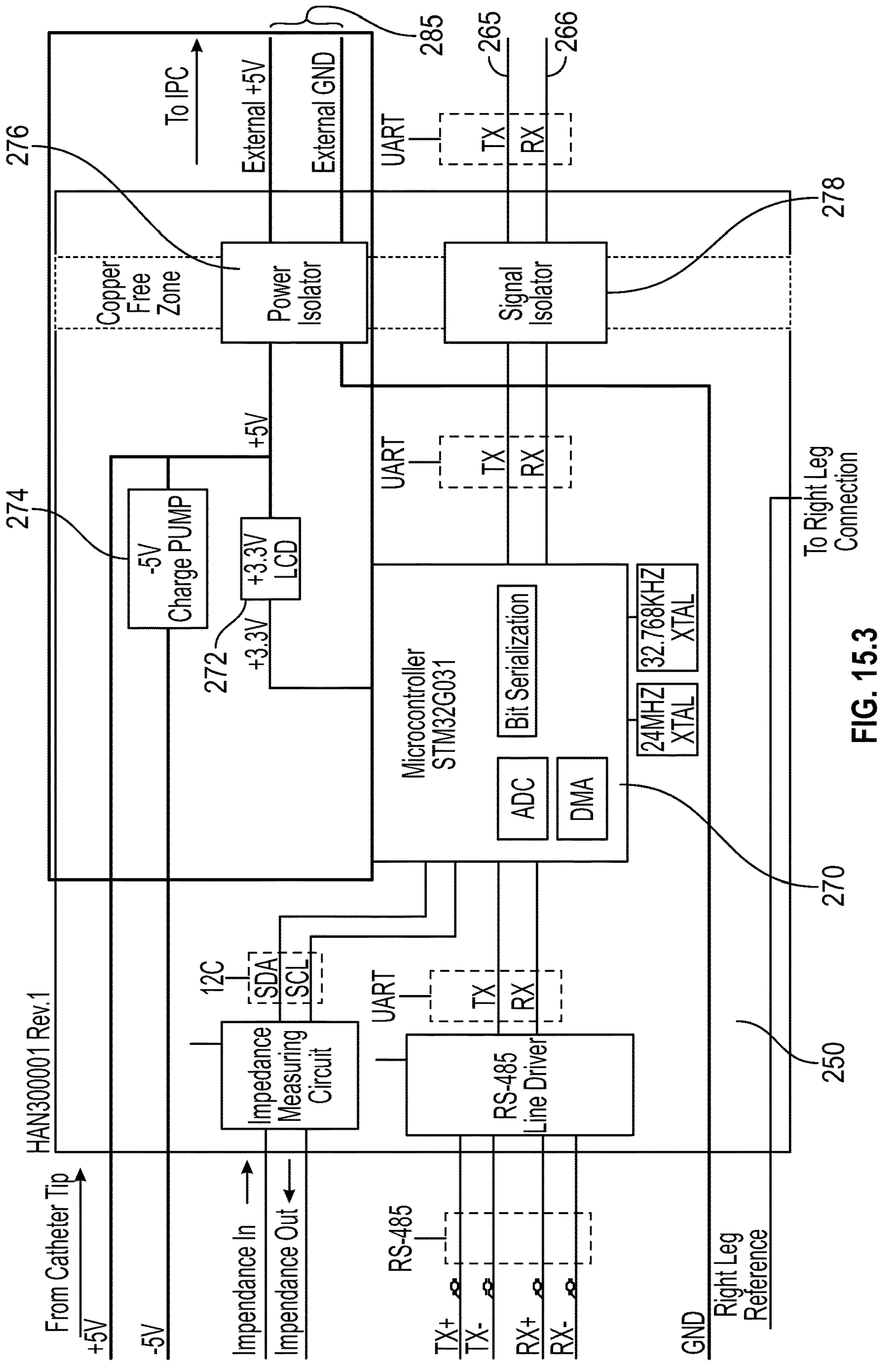
FIG. 15.3

ROBOTICALLY CONTROLLED ELECTROPHYSIOLOGY CATHETER WITH CLOSED LOOP CONTROL

RELATED APPLICATIONS

The present application is a continuation in part application pursuant to 35 USC 120 of OPTICALLY COUPLED CATHETER AND METHOD OF USING THE SAME, U.S. patent application Ser. No. 16/424,202, filed May 28, 2019, and A CATHETER FOR CARDIAC AND RENAL NERVE SENSING AND MEDIATION, U.S. patent application Ser. No. 17/468,460, filed Sep. 7, 2021.

The following patents, applications and patent publications, currently abandoned or issued, are related to the present application, all and each of which are incorporated herein by reference: US Pat. Pub. 2008/0249395 A1—METHOD AND APPARATUS FOR CONTROLLING CATHETER POSITIONING AND ORIENTATION; U.S. Pat. No. 8,986,214 B2—SYSTEM AND METHOD FOR USING TISSUE CONTACT INFORMATION IN AN AUTOMATED MAPPING OF CARDIAC CHAMBERS EMPLOYING MAGNETICALLY SHAPED FIELDS; U.S. patent application Ser. No. 12/475,370, entitled "Method and Apparatus for Magnetic Waveguide Forming a Shaped Field Employing a Magnetic Aperture for Guiding and Controlling a Medical Device," filed on May 29, 2009; US Pat. Pub. 2012/0316431 A1—METHOD FOR ACQUIRING HIGH DENSITY MAPPING DATA WITH A CATHETER GUIDANCE SYSTEM, which is a continuation of U.S. patent application Ser. No. 12/582,588, filed Oct. 20, 2009; US Pat. Appl. 2006/0116634 A1—SYSTEM AND METHOD FOR CONTROLLING MOVEMENT OF A SURGICAL TOOL, which is a divisional of U.S. patent application Ser. No. 10/621,196 titled APPARATUS AND METHOD FOR A CATHETER GUIDANCE CONTROLAND IMAGING, which was filed Jul. 15, 2003 which claims priority from U.S. Provisional Pat. Appl. No. 60/396,302, filed Jul. 16, 2002, titled "CATHETER GUIDANCE CONTROL AND IMAGING APPARATUS AND METHOD"; US Pat. Pub. 2012/0288838 A1—METHOD FOR SIMULATING A CATHETER GUIDANCE SYSTEM FOR CONTROL, DEVELOPMENT AND TRAINING APPLICATIONS, which is a continuation of U.S. patent application Ser. No. 12/582,621, filed Oct. 20, 2009; U.S. Pat. No. 9,655,539 B2—SYSTEM AND METHOD FOR TARGETING CATHETER ELECTRODES, which is a continuation of U.S. patent application Ser. No. 12/615,176, filed Nov. 9, 2009; U.S. Pat. No. 8,457,714 B2—SYSTEM AND METHOD FOR A CATHETER IMPEDANCE SEEKING DEVICE; US Pat. Pub. 2009/0275828 A1—METHOD AND APPARATUS FOR CREATING A HIGH RESOLUTION MAP OF THE ELECTRICAL AND MECHANICAL PROPERTIES OF THE HEART; and US Pat. Pub. 2009/0253985 A1—APPARATUS AND METHOD FOR LORENTZ-ACTIVE SHEATH DISPLAY AND CONTROL OF SURGICAL TOOLS.

BACKGROUND

Field of the Invention

The invention relates to systems and methods for guiding, steering, and advancing an invasive medical device in a patient while using a sensor and fiducial markers to determine the location and orientation of the catheter.

The invention further relates to the field of medical mapping systems, namely systems and methods for guiding, steering and advancing an invasive medical device in a patient for the purpose of defining the physical boundaries and surface properties of a chamber or orifice.

The invention further relates to the systems and methods for guiding an invasive medical device within a patient for the purpose of mapping anatomical cavities.

The invention further relates to systems and techniques for guiding, steering, and advancing invasive medical devices such as catheters and catheter-type devices.

The invention further relates to the systems and methods for guiding, steering and advancing an invasive medical device in a patient.

The invention further relates to the placement of catheters in contact with specific anatomical locations while optimizing the direction and orientation of tissue contact.

The invention further relates to the field of acquiring high-resolution clinical models of various properties of the heart using an invasive medical device and systems and methods for locating and tracking the invasive device.

DESCRIPTION OF THE PRIOR ART

Catheterization is typically performed by inserting an invasive device into an incision or body orifice. This procedure relies on manually advancing the tip of the invasive device by pushing, rotating, or otherwise manipulating the proximal end which remains outside of the body.

The prior art approach to solving the fiducial relationship between the moving catheter tip and the heart catheter relies on manually advancing the catheter tip by pushing the proximal end of the catheter, while grossly neglecting the respiratory outputs (ribcage displacement), heart contraction, QRS synchronization, patient operating bed location, and image capture (x-ray or other imaging modalities) to approximately move the catheter from the current Actual Position (AP) to the Desired Position (DP).

Review of the prior art and its limitations indicate the inability of the prior art solutions to account for the global orientation of the catheter tip relative to frame distortion associated with the operating table, QRS synchronization timing point, or image acquisition, where the data points (e.g., the vector space) are normalized to the patient local coordinate system.

The limitations of the prior art are characterized by the fact that the operator requires the system to define an accurate position for moving the catheter tip from actual position to its desired position in an "autopilot" regimen. The prior art cited cannot perform the task because the position and orientation of the catheter tip is influenced by more than the local coordinate system and it is dependent on many variables such as, heart dynamics, fiducial external sensor, and patient's body relative to the operating table, etc.

Therefore, there is a substantial and unsatisfied need for an apparatus and method for detecting the position and orientation of a medical tool such as a catheter or catheter-like devices for guiding, steering, advancing the position of an invasive device, for accurately controlling their position, for providing three-dimensional imaging, and for minimizing the use of x-ray or other ionizing radiation.

BRIEF SUMMARY

The preferred embodiments of the invention and its scope are best understood by first appreciating the problems, which needed to be solved in order to realize the goals or objects of the invention.

Standard diagnostic methods of identifying pacing disturbances in the electrical activity in the heart are well known. The cardiac waveform has a certain characteristic time-domain pattern and an amplitude that are considered normal and healthy. Although there are variations from on a normal distribution in the length and amplitude of electrical activity among patients of different genders and age, in general the electrical patterns are the essentially the same in shape and the time-domain characteristics, namely approximately 60 beats per minute (1 Hz), and sometimes when there is exercise or pressure, up to 1.5 Hz or 90 bpm. For example, an older, slower heart is typically as low as 45 bpm, a normal heart 60-70, and an young athlete of 25 years is 65 bpm. Rates are typically slower in people with difference sizes, maladies, weights, and preexisting conditions.

There are two broad categorizations of cardiac disease derived from identification of the disease based on the waveform, its geometric and time-domain characteristics. The disease models are described by the geometric and time-domain aspects of the waveform. For example, patients with a slow heart (bradycardia), and patients with a fast heart (tachycardia). These categorizations arise from disturbances in the pacing. It starts with the QRS waveform, for example, with an ectopic signal coming from sino-atrial node, which comes from the autonomic nervous system, which triggers the performance of the heart responding to a heart wave from the sino-atrial node to the HIS bundle, to the Purkinje fibers to the mitral valve and to the pulmonary vein.

There are classes of disease models such as atrial fibrillation, (AFib) such as persistent AFib, and paroxysmal AFib. There are accessory pathways in different locations, and there is VT/tachycardia, all varieties of disease models relating to abnormal pacing. An electrophysiology catheter must be able to uncover abnormal cardiac behavior from the cardiac waveform.

Unfortunately, the underlying waveforms, namely the electrical activity of the cardiac DC potential in a time-domain, are subject to additional parameters that affect the measurement, such as the nature of the contact surface, which is often critical in obtaining an accurate measurement of the cardiac signal. The signal is not emanating just from the surface of the endocardial area, like the outer layers of the inner surface of the heart, but also from the substrate, the entire thickness of the cardiac muscles. Because the cardiac signal is transmitted from its origin site, the nature of the deep cardiac tissue also affects cardiac measurement. The proximity of signal-emitting tissue varies from 2 mm on the pulmonary vein to 50 mm on the ventricle.

A catheter with multiple electrodes, measuring either in unipolar or bipolar configuration, picks up electrical activity on the surface of the heart, and in doing so requires an electrical contact with the heart that is substantially constant in order to accurately detect a cardiac event in a time domain that realistically represents the vectorial waveform magnitude and direction. The electrophysiologists needs to know where the cardiac wave moves to, in what space does cardiac wave move (its trajectory), and what is its amplitude. In addition, some of the clinical signals of interest range between 5-25 μV in amplitude.

These signals are subject to error and noise, because the environment outside the patient, including the patient himself, can have a myriad of electrical signals that are substantially larger than the potential of interest. An example is the electrical output from the lights and hospital equipment in the operating room which is around 60 Hz (50 Hz in Europe). They radiate an enormous amounts of power relative to the cardiac signal at 5 μV. Many of the noise characteristics are detectable because of their repeatability, and they we can be removed with a high-pass filter, low-pass filter, or other forms of analytical discrimination between signal and noise. Many of the signals of interest (5-25 μV) ride on a very large signal, so noise is the leading vector in size, magnitude, and direction, compared to the signal of interest. It is like trying to scoop a specific drop of water from a full bucket.

Using conventional filters as is used with analog electrodes, the filters are like a lawnmower, namely when you "cut the grass" you also "cut the daisies", eliminating low-performing signals of CFAE (complex fractionated atrial electrogram) which are indications of areas where scar tissues are located. Current flows around the scar tissue island, either clockwise or counter-clockwise.

The aim of our technology is how to fish the little "drop of water" that is of interest without fishing out the whole bucket of water. We must fish with a hook that is very specific. As disclosed below we can only do that if we pick the native signal, amplify it locally, digitize it so as a "digital word", it is immune to any outer analog interference, and then transmit it to the station for processing to produce a map.

Another goal is to pick up the signal in a time domain to allow us to see the entire cineography of the heart wave, like a video, so instead of having 50 Hz update as the current system operates. As disclosed below we operate at 1 KHz, where we are an order of magnitude higher resolution in the time domain than conventional cardiac monitors. The dynamic range has a better representation of what is happening in each fraction of a second where the events take place. Signals with a low power can be picked up, and they are captured locally in a digital word that is no longer trapped along a 1-meter-long catheter shaft, which behaves as an antenna, going to a 5-meter-long cable into a workstation which processes it. Heart performance is not measured with a fiducial representation, but is actually captured at its naturally occurring rate.

Now it can be appreciated what is required to uncover the electrical activity of the substrate tissue of the heart (which is a circuit starting from the SA node to the HIS bundle, to the Purkinje fibers and to the mitral valve. Cardiac electrical activation is more like a battery structure where there is an avalanche between ionic structure of cellular matrices that are cascading into each other on a time domain. Sometimes there is a scar tissue which creates islands which diverts the signal from its native linear propagation as defined for a normal patient. What we do by exploring the endocardial surface of the heart, especially in AFib (or the left atrium), is where there is an aberration, where the geometry and time domain variations are occurring, and then we later apply a therapeutic approach to correct it, to rewire or remodel the heart's electrical system from a spurious junction to a new rewiring by ablating and creating a path that allows the waveform to travel in a more linear fashion to achieve the time domain of a sinus rhythm, which is the ultimate goal of a therapeutic approach.

What we find out is, that in the exploration of the diagnostic phase and therapeutic phase, both are subject to a macro that is common for a common disease (such as AFib). For example, the approach created by Haïssaguerre (1982), in his seminal paper about the relationship between pulmonary vein isolation and correction of arrhythmia, and the continuation of a therapeutic for more complex cases. For example, one correction includes where there is a roofline ablation and an isthmus line complementary ablation, which separates the pulmonary vein, the roofline and the isthmus all the way to mitral valve which creates a line of isolation that recovers a persistent AFib. There are other cases such as accessory pathways, and the strategy for each one is known. It means that there are sets of cardiac macros that physicians apply in the diagnostic and therapeutic modes. In both diagnostic and therapeutic cases, it lends itself to a specific macro.

The concept of Huygens catheter disclosed below is to solve two big issues: on the one hand, increase the resolution of the impedance microscopy to measure the potential at as low as 5 μV to uncover CFAE events, and on the other hand, change the dynamic range by going from a small frequency domain of 50 Hz to 1 KHz (digitally). By these two steps we are able to scan and create maps that demonstrate the dynamic of the waveform magnitude and direction.

The map created subsequently represents more realistically, through cardio processing systems such as Carto, Ensite and others, two things: the combination of the location of the catheter position and orientation, and measurement of the DC potential over the surface of the heart in the time domain, while measuring the contact surface to verify consistent pressure. As disclosed below taking the ordered tuple data set of DC cardiac potential Z, position P, orientation O, contact impedance Q and time t, <Z, P(xyz), O(xyz), Ω, t>, all relative to a standard QRS event, there is an adiabatic timer that is inherent to the patient tied to an identifiable cardiac event in the human heart and specifically to that patient.

The aberrations of geometrical displacements in the time-domain are measured against a known standard internal reference which is the heart of the patient. As we map, we record the places where we have seen an aberration, not approximately on the screen and then estimating how to return to that location as was the conventional, but by recording position and orientation, we set markers and use of the Proteus robot to reliably move the catheter specifically to these coordinate sets with a +/−1 mm margin of error, depending on the system. This lends itself to a macro-operation, where two very complex subjective sets of in the time domain are reduced to a machine language that is capable of capturing the mapped terrain with the electro-anatomical activity and its definition on a three-dimensional grid, which is recognized by a robotic system that uses the loop to lock in and place the catheter in that location of interest to the physician.

A better diagnostic microscopy of the position, orientation, and DC potential of the disease is performed, and then the catheter or another surgical tool is translated and rotated back to that location with the robotic system for a therapeutic response. The physician's diagnostic approach is reduced and recorded into a machine language, and the dexterity of the physician is turned it into a set of machine commands. In both cases, macros are interrelated into a complex loop, and that loop is then stored and reported directly into the "Cloud", which then enables the physician to maintain an understanding of future cases or progression of the disease if it reoccurs and repeats itself.

The system described herein solves these and other problems by locating the catheter tip in a robotic chamber and within the patient's body. In one embodiment, the catheter is located in the heart in the presence of dynamic motion under the QRS regiments (e.g., while undergoing the systole/diastole cycle).

The position and orientation of the catheter is tracked in the presence of dynamical variables, such as, movement of the catheter from its actual position (AP) to its desired position (DP), the dynamics of the patient's heart during its mechanical contraction and repolarization of the heart muscle, the location of the catheter tip relative to the organ's specific anatomy, the operating table, and all the above variables relative to the orientation of the imaging modality used in viewing the organ, (e.g., ultrasonics, radar, x-ray, x-ray with different angulation AP caudal 20° etc.).

Many of the variables are relatively independent of each other such that there is no useful functional relationship between each one of the elements which define the position of the catheter so as to predicate the other variables. The operating table position, the respiratory chest positions, the movement of catheter tip from AP to DP, the heart cycle, the QRS signal, and the x-ray image orientation are relatively independent variables. One embodiment provides a correlation of these variables.

In a catherization system, the robotic guidance & control system must be capable of identifying the position and orientation of the catheter tip in order to be able to operate in closed-loop servo mode. In one embodiment, the system is used in connection with a cardiology procedure, such as, for example, an electrophysiological (EP) procedure of mapping and ablation by using the robotic guidance & control system to control, guide, and image the catheter's position and orientation.

One embodiment includes a servo closed-loop robotic guidance & control system controller where:

a. The patient's rotation relative to the catheter's tip (the tip) is independent of the transformation for finding the accurate position and orientation of the catheter's tip.
b. The location and movement of the organ (e.g., heart) relative to the operating table is independent of the transformation for finding the accurate catheter's position and orientation.
c. The patient's position and heart orientation relative to the operating table as well as the orientation of the auxiliary imaging equipment are independent variables and can be accounted for. Without loss of generality, the system can provide an accurate catheter position and orientation under conditions noted above.
d. The system is able to provide servo closed loop control while accounting for translation and rotation of the catheter tip relative to a set of independent variables, such as the patient's orientation relative to the operating table, image acquisition orientation (e.g., AP, RAO, caudal, etc.), respiration mode, and the QRS heart dynamic (muscle contraction and repolarization).
e. The system, including the catheter position detection unit and its three dimensional vectors, the QRS synchronization unit, the fiducial alignment system, the operation console (includes the display, haptic controller, and mouse) the mapping unit, the position recording unit, the fiducial sensor, the operating table, configuration file holding the three dimensional models, a three dimensional heart model, a three dimensional torso model, a three dimensional atrial parts model) determine the position and orientation of the catheter tip under dynamic conditions as indicated in i thru iv above. The patient's organ and its specific anatomical site are synchronized to form a normalized vector field (orthogonal to the global coordinate system) further facilitating the operation of the servo closed loop.

One embodiment includes a robotic guidance & control system apparatus for determining the position and orientation of the catheter's tip under an translation or rotation of variables, relative to patient specific anatomical features such as the heart, right atrium, inferior vena cava, superior vena cava, right atrium lateral wall, His Bundle, interatrial trans-septum, heart left atrium, heart right ventricle, heart left ventricle, heart tricuspid valve, heart mitral valve, electro-cardiac signal, QRS synchronization timing point, and respiration signal, etc.

The catheter tip is detected and displayed relative to the fiducial sensor position and orientation with its orthogonal vector set: the fiducial x-axis, FX; fiducial y-axis, FY; fiducial z-axis, FZ; and fiducial position, FP.

In one embodiment, the actual catheter tip and virtual catheter tip are normalized under the global orientation transformation matrix, GO, and global position transform matrix, GP.

In one embodiment, the detection unit provides data for defining the location of the catheter tip, forming a map and synchronizing the location to the patient's, his or her heart and specific anatomical features e.g. His Bundle, its electro-cardiac signal, and/or its QRS synchronization timing point. The catheter position and orientation is further corrected relative to respiration signal (pulmonary chest displacement).

The closed loop control system uses the ability of the imaging and synchronization module to locate, identify, and report the position and orientation of the catheter tip in three-dimensional space under dynamic conditions (e.g., heart muscle contraction and repolarization) while considering respiration distortion of the ribcage, the patient's position relative to the operating table and the specific image capture relative to the patient's organs.

The system provides an accurate position and orientation of the catheter's tip the presence of relatively independent dynamic variables. The movement of the catheter tip from its actual position AP (catheter axis, global coordinates, and catheter position, global coordinate) to its desired position DP, the movement of the catheter tip, the patient, heart and its specific anatomical features (e.g. heart left atrium) are relatively independent variables.

In one embodiment, the system is used in connection with a procedure for finding the tricuspid valve in a rotated patient.

In one embodiment, the system is used in connection with a procedure for finding the pulmonary vein in a rotated patient.

In one embodiment, the system is configured to determine the position and orientation of the catheter tip and or surgical tools while accounting for mechanical contraction of the heart muscle, its electrical excitation propagation in three dimensional space (one embodiment of a technique for computing the Laplacian cardiac electrogram and the wave equation characteristics used by the robotic guidance & control system apparatus is further described by U.S. patent application Ser. No. 11/362,542, hereby incorporated by reference).

In one embodiment, the multiple dynamic and independent variables such as QRS complex, catheter position and orientation, and the outside fiducial markers are normalized in real time to facilitate the servo closed loop modality for controlling the movement of the catheter from AP to a DP. The actual position (AP) is mapped onto the virtual models and patient anatomy by using the global position and orientation matrices generated to account for the shifts of position and orientation of the fiducial alignment sensor caused by patient motion and ribcage displacement due to respiration. Using these matrices, the operator commands, the patient and the patient data are synchronized, and the desired position and orientation (DP), is generated as a conformal map relative to the actual catheter tip position (AP) and patient anatomy, further forming a servo close loop modality for control, guidance and imaging of catheter tip in a human heart or other internal anatomical site of interest.

In one embodiment, a fiducial map is used to relate dimensional, anatomical and electrical elements in real time.

One embodiment includes a robotic catheter guidance and control apparatus that requires less training and less skill than prior art systems.

In one embodiment, an RF trilateralization system is used to determine the location of the tip of the catheter inside the body, thus minimizing or eliminating the use of ionizing radiation such as X-rays. Alternatively, the catheter guidance system can be used in combination with an X-ray system (or other imaging system) to provide additional imagery to the operator. Moreover, the robotic system used in the robotic catheter guidance system can also be used to locate the catheter tip to provide location feedback to the operator and the control system.

One embodiment includes a catheter and a guidance and control apparatus that can accurately, and with relative ease, allow the surgeon/operator to position the catheter tip inside a patient's body. The catheter guidance and control apparatus can maintain the catheter tip in the correct position.

One embodiment includes a catheter and a guidance and control apparatus that can steer the tip of the catheter through arteries and forcefully advance it through plaque or other obstructions.

One embodiment includes a catheter guidance and control apparatus that displays the catheter tip location with significantly reduced X-ray exposure to the patient and staff.

One embodiment includes a catheter guidance and control apparatus that is more intuitive and simpler to use, that displays the catheter tip location in three dimensions, that applies force at the catheter tip to pull, push, turn, or hold the tip as desired, and that is capable of producing a vibratory or pulsating motion of the tip with adjustable frequency and amplitude to aid in advancing the tip through plaque or other obstructions.

One embodiment provides tactile feedback at the operator control to indicate an obstruction encountered by the tip.

In one embodiment, the catheter guidance control and imaging (robotic guidance & control system) system allows a surgeon to advance, accurately position a catheter, and to view the catheter's position in three dimensions by using a detection system to locate the tip of the catheter.

In one embodiment, the detector data can be combined with X-ray imagery to produce a composite display.

In one embodiment, the detector is a system which includes an RF trilateralization system.

In one embodiment, the apparatus includes a user input device called a "virtual tip" that, in addition to being a representation of the actual or physical catheter tip advancing within the patient's body, possesses a positional relationship to the catheter tip. The virtual tip includes a haptic joystick that can be manipulated by the surgeon/operator and is also designed to deliver tactile feedback to the surgeon in the appropriate axis or axes if the actual tip encounters an obstacle. In other words, the virtual tip includes a joystick type device that allows the surgeon to guide the actual catheter tip though the patient's body. When the actual catheter tip encounters an obstacle, the virtual tip provides tactile force feedback to the surgeon to indicate the presence of the obstacle.

In one embodiment, the robotic guidance & control system apparatus uses a technique of image synchronization by using a sensor having six degrees of freedom (6-DOF), thereby allowing the formation of a stereotaxic frame of reference.

In one embodiment, the robotic guidance & control system apparatus uses numerical transformations to compute currents to be provided to various servo motors to control the catheter guidewires used to push, pull and rotate the catheter tip in an efficient manner.

In one embodiment, the robotic guidance & control system apparatus includes an RF trilateralization system and a 6-DOF sensor configured to detecting the catheter tip and moving body organs, and synchronize their motions.

In one embodiment, the robotic guidance & control system apparatus is used to perform an implantation of a pacemaker leads during an electrophysiological (EP) procedure.

In one embodiment, the robotic guidance & control system apparatus uses a detector or other sensors to measure, report and identify the location of a moving organ within the body (e.g., the heart, lungs, etc), with respect to the catheter tip and one or more fiducial markers, so as to provide guidance control and imaging to compensate for movement of the organ, thereby simplifying the surgeon's task of manipulating the catheter through the body.

In one embodiment, the operator control provides the position and orientation command inputs to a servo system that controls the catheter tip position by regulating the mechanical force applied inside the patient's body. A measurement of the actual tip position and orientation is made via sensory apparatus that includes a radar system, and the 6-DOF sensor. This measurement is used to provide feedback to the servo system and the operator interface.

In one embodiment, the servo system has a correction input that compensates for the dynamic position of a body part, or organ, such as the heart, thereby offsetting the response such that the actual tip moves substantially in unison with the beating heart.

In one embodiment, operation of the catheter guidance system is as follows: i) the operator adjusts the physical position of the virtual tip; ii) a change in the virtual tip position is encoded and provided along with data from the detector system and a 6-DOF sensor to a control system; iii) the control system generates servo-system commands that are sent to a servo system control apparatus; iv) the servo system control apparatus operates the servo mechanisms to adjust the tension force applied to the guidewire assembly to form the necessary geometry calculated by the resident computer; v) the position of the actual robotic catheter tip within the patient's body is changed; vi) the new position of the actual catheter tip is then sensed by the detector and the position of a plurality of fiducial markers are sensed by the 6-DOF sensor, thereby allowing synchronization and superimposing of the catheter position on an image produced by fluoroscopy and/or other imaging modality; and vii) feedback is provided to the servo system control apparatus and to the operator interface; and viii) the displayed image of the actual catheter tip position in relation to the patient's internal body structures is updated.

The operator can make further adjustments to the virtual catheter tip position and the sequence of steps ii through viii are repeated. In one embodiment, feedback from the servo system control apparatus creates command logic when the actual catheter tip encounters an obstacle or resistance in its path. The command logic is used to control stepper motors which are physically coupled to the virtual catheter tip. The stepper motors are engaged as to create resistance in the appropriate directions that can be felt by the operator, and tactile feedback is thus provided to the user.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 1.1, included in an inset in FIG. 1A, is perspective view of the printed circuit board layout of the catheter tip. FIG. 1.2, included in an inset in FIG. 1A, is an enlarged perspective view of the distal end of the catheter sheath. FIG. 1.3, included in an inset in FIG. 1A, is an enlarged side transparent or internal view of the manual handle connected to the proximal end of the catheter. FIG. 1.4 is a side cross-sectional view of handle, and FIG. 1.5 is an exploded perspective view of handle. FIG. 1.6 is side transparent view of catheter tip and the opposing pair of pull wires along with a safety wire fixed to tip to insure its retention on the catheter.

FIG. 7.1 is a block diagram of the multiplexing circuit located proximal to the flexible printed circuit board (FPC)

and FIG. 7.2 is a perspective view showing the physical placement of the multiplexing circuit on the FPC, FIGS. 7.3A and 7.3B, collectively referred to herein as FIG. 7.3, identify the multiplexing circuit in the circuit block diagram of FIG. 2.

FIG. 8.1 is a schematic circuit diagram depicting the amplification elements of the Huygens catheter, FIG. 8.2 is a perspective view showing the physical location of the amplification elements on the FPC, FIGS. 8.3A and 8.3B, collectively referred to herein as FIG. 8.3. identify the corresponding portion of the circuitry in the circuit block diagram of FIG. 2.

FIG. 9.1 is a schematic circuit diagram of the A/D processing circuit for the DC voltage potential, FIG. 9.2 is a perspective view showing the physical location of the A/D processing circuit on the FPC, FIGS. 9.3A and 9.3B, collectively referred to herein as FIG. 9.3, identify the corresponding portions of the circuitry in the circuit block diagram of FIG. 2.

FIG. 10.1 is a schematic circuit diagram of the data transmission elements, FIG. 10.2 is a perspective view showing the physical location of the data transmission elements on the FPC. FIGS. 10.3A and 10.3B, collectively referred to herein as FIG. 10.3, identify the corresponding circuitry in the circuit block diagram of FIG. 2.

FIG. 11.1 is a block circuit diagram of the cardiac signal flow elements. FIG. 11.2 shows the physical layout of the cardiac signal flow elements on the FPC with the wiring labels. FIG. 11.3 identifies the corresponding circuitry in the circuit block diagram of FIG. 2.

FIG. 12.1 is a circuit block diagram of communication elements used between the electrodes and the electronic circuit. FIG. 12.2 shows the physical layout of the communication elements on the FPC, FIG. 12.3 identifies the corresponding circuitry in the circuit block diagram of FIG. 2.

FIG. 13.1A and 13.1B, collectively referred to herein as FIG. 13.1, form a schematic circuit diagram of the impedance measuring circuit. FIG. 13.2 shows the physical layout of the impedance measuring circuit on the FPC, FIG. 13.3 identifies the corresponding circuitry in the circuit block diagram of FIG. 2.

FIGS. 14.1 and 14.2 are schematic circuit diagrams of the universal asynchronous receiver- transmitter (UART) circuitry for the communication protocol and the signal integration of the cardiac signal output. FIG. 14.3 shows the physical layout of the UART communication and cardiac signal integration circuitry on the FPC. FIG. 14.4 identifies the corresponding circuitry in the circuit block diagram of FIG. 2.

FIG. 15.1 is a schematic diagram of the power circuitry and isolation technique of the Huygens catheter. FIG. 15.2 shows the physical layout of the power and isolation circuitry on the FPC, FIG. 15.3 identifies the corresponding circuitry in the circuit block diagram of FIG. 2.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
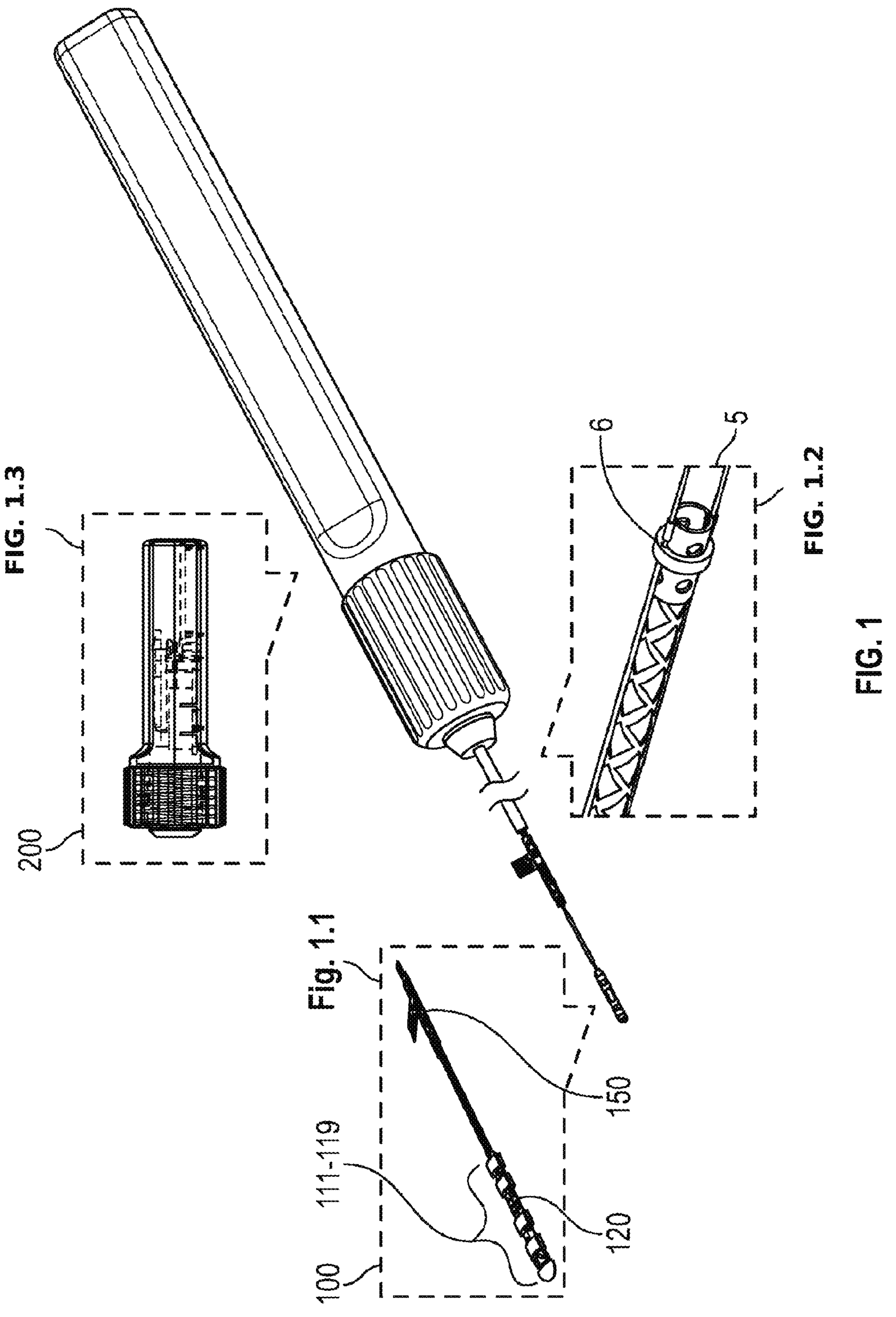
FIG. 1 is a perspective view of the catheter tip, sheath and manually operated handle includes three views of the smart catheter electronic components and its scaffold, starting with an external side view at the top, an internal side view in the middle and an internal top view of the circuit-carrying components at the bottom.

FIG. 1 is a perspective representation of a catheter 100 employed in the Huygens Catheter as described below, with its three main subassemblies: 1) the distal end of the catheter FPC 120, 2) the overlay sheath 5, and 3) the catheter handle 200 having a kinematic mechanism therein as partially seen in FIG. 1.3 for differentially tensioning the pulley wires to deflect the catheter tip 120. The kinematic mechanism is described in more detail in incorporated application Ser. Nos. 16/424,202 and 17/468,460, and is shown in greater detail in FIGS. 1.4-1.6. FIG. 1.4 is a side cross-sectional view of handle 200 and FIG. 1.5 is an exploded perspective view of handle 200. Knob 202 has internal threading and threadably engages a piston 203 by means of opposing pairs of tabs 205 riding in the threading of knob 202 in order to move piston 203 longitudinally within handle 200 as knob 202 is rotated. Pull wire 7 has one end fixed within handle 200 and is coupled by a stop or other means to the proximal end of piston 203, led around pulley wheel 211, then led distally out of handle 200 to and fixed to catheter tip 120. The opposing pull wire 7 is also fixed to catheter tip 120 and is led proximally back to handle 200 where it is led through end 209 of piston 203 and fixed to handle 200. Both ends of pull wires 7 fixed to handle 200 are spring loaded to allow resilient tension to be maintained on pull wires 7. Differential tension or extension applied by piston 203 by means of knob 202 causes catheter tip 120 to be deflected or allows it to straighten. FIG. 1.6 is side transparent view of catheter tip 120 and the opposing pair of pull wires 7 along with a safety wire 213 fixed to tip 120 to insure its retention on the catheter.

The size of the sheath 5 is typically 6 or 7 French for use in the cardiovascular system and all circuitry and chips must be dimensioned to fit within the inner diameter of a catheter of that size, while still maintaining the required flexibility. Hence, the sizing and placement of rigid integrated circuit chips and their associate wiring must be carefully thought out and the following figures shown an embodiment in which such placements or layouts can be realized. The catheter assembly includes a handle 200, a distal end flex circuit 120 carrying the sensing electrodes 111-119, a protective overlay sheath 5, enclosing the entire assembly, including a sleeve ring 6 to which a safety wire 135, shown in FIG. 1A, and a pair of pulley wires 7 are affixed. Pulley wires 7 are disposed in PTFE liners to insure lubrication and sheath 5 is coated with an inner PTFE layer and reinforced with a flexible braid. Handle 200 includes a rotatable knob 202, which selectively tensions each of the pair of opposing pulley wires 7 to deflect catheter tip 120. The proximal flex section 150 of the assembly in FIG. 1.1 includes the electronic processing unit is electrically connected via a wire bundle 140 to FPC 120. The structural as well as functional elements of the novel catheter and its intended use are detailed below.

Figure 1A:
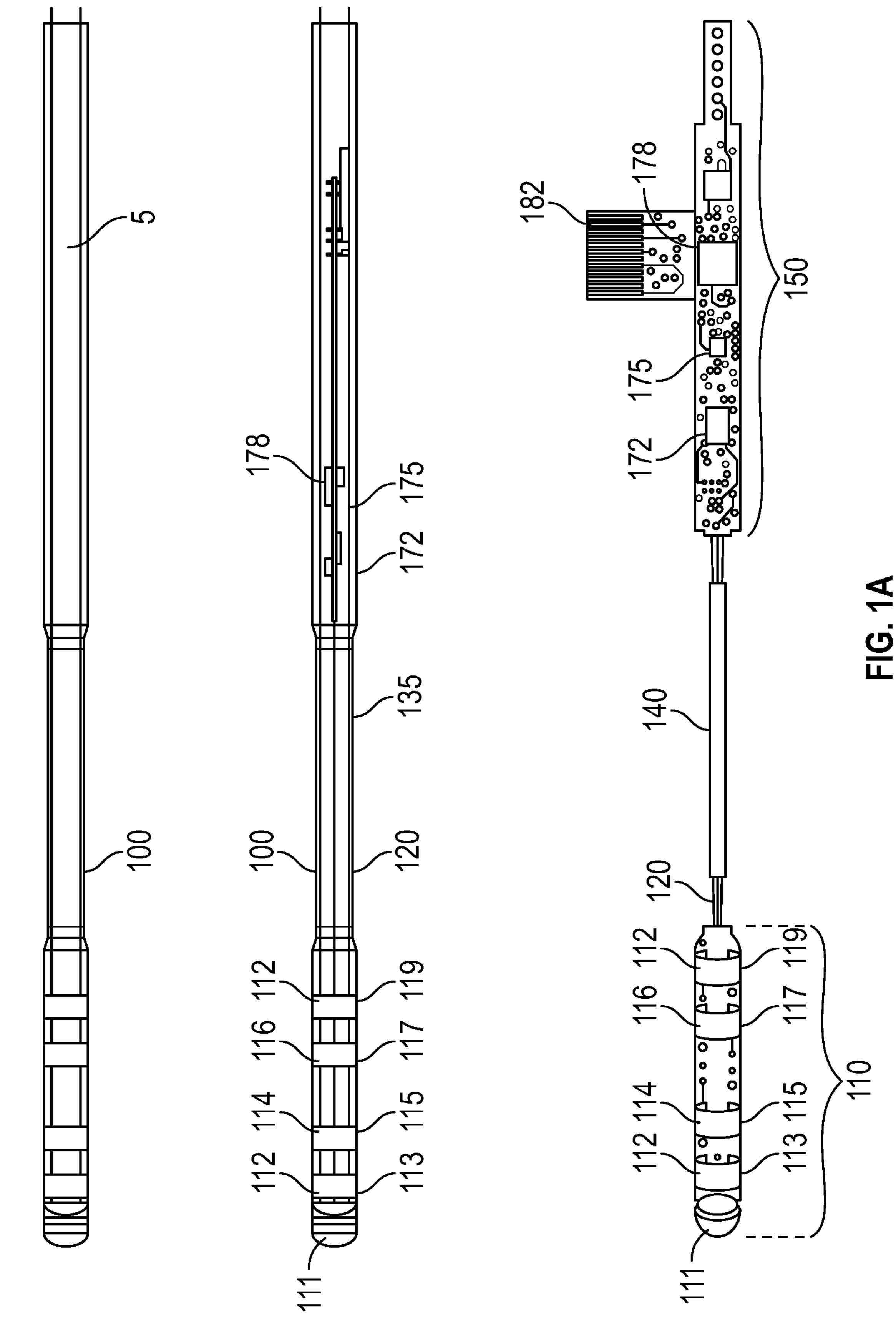

FIG. 1A includes three views of the smart catheter electronic components and its scaffold, starting with an external side view at the top, an internal side view in the middle and an internal top view of the circuit-carrying components at the bottom. These views of the catheter 100 depict the placement of the major electronic elements included in the Huygens catheter assembly. The catheter 100 provides the sensing elements, such as the set of electrodes 111-119 mounted on a distal tip 110 and attached to a flex printed circuit board (PCB) 120 to provide the necessary metrics customary in an electrophysiological study, for example the metrics provided by an electrode assembly having a spacing of 2 mm between a tip electrode 111 and a first pair of electrodes 112-113, another spacing of 2 mm between the first pair 112-113 and a second pair of electrodes 114-115, a spacing of 5 mm between the second and a third pair of electrodes 116-117 and a spacing of 2 mm between the third and a fourth and last electrode pair 118-119. These metrics are preserved to provide a standard for an electroanatomical waveform.

A safety wire 135 connects the distal tip electrode 111 to the sleeve 6. The proximal end flex circuit 150 carries the electronic assembly which enables the DC potential signal to be sensed by the electrodes 111-119, and thereafter digitized, amplified, filtered, multiplexed and transmitted via a communication protocol to the electronics in handle 200. The details of this signal flow are described in the subsequent figures. A programming flap 182 is provided for programming the digital circuits in proximal FPC 150 and is removed or cut off once the circuits have been programmed.

Figure 2A:
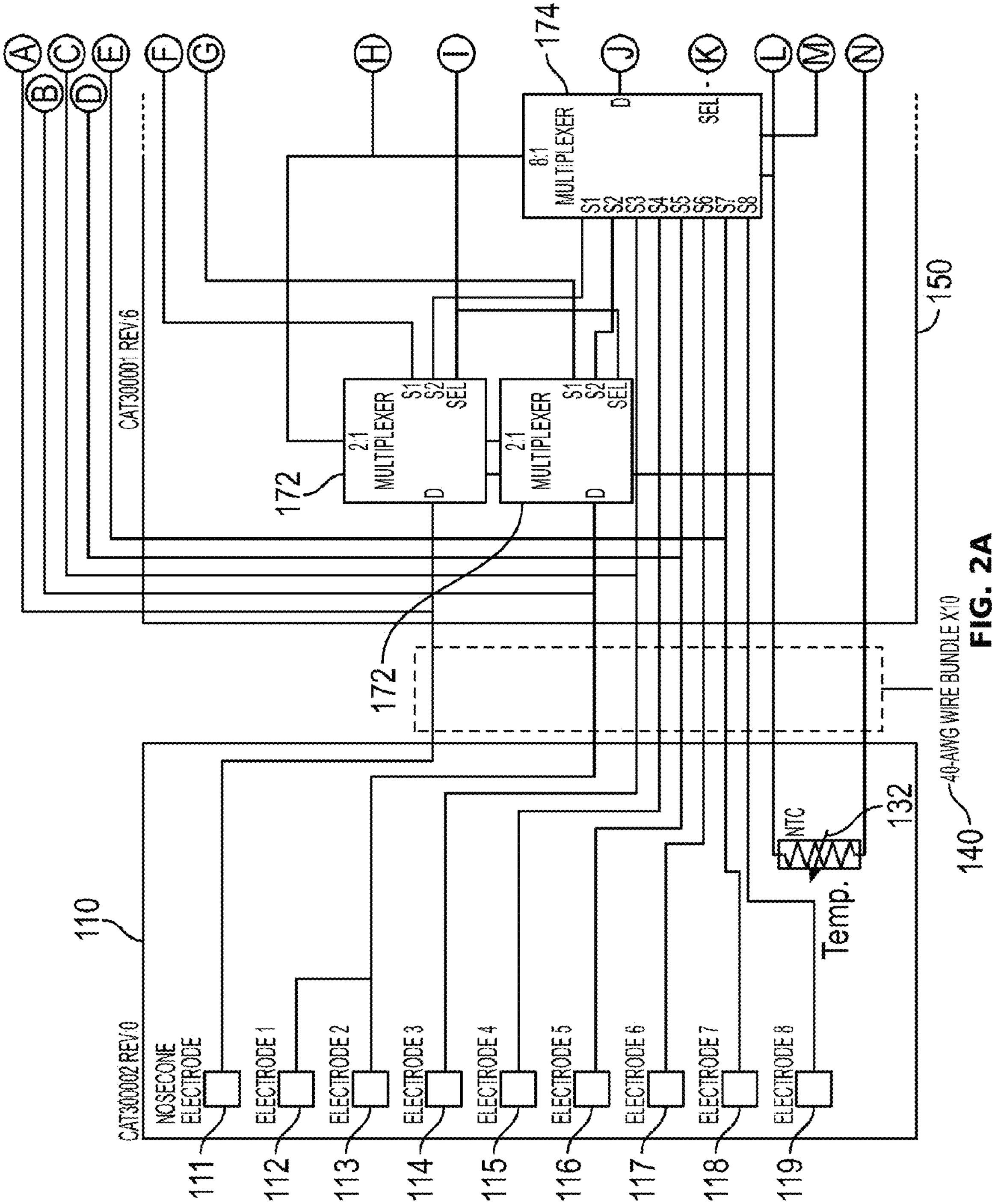
FIGS. 2A and 2B, collectively referred to herein as FIG. 2, form a circuit block diagram of the Huygens catheter assembly depicting the distal tip subassembly containing all functional elements for the detection, amplification, digitization, multiplexing, and communication of the native signal using multiple split electrodes.
Figure 2B:
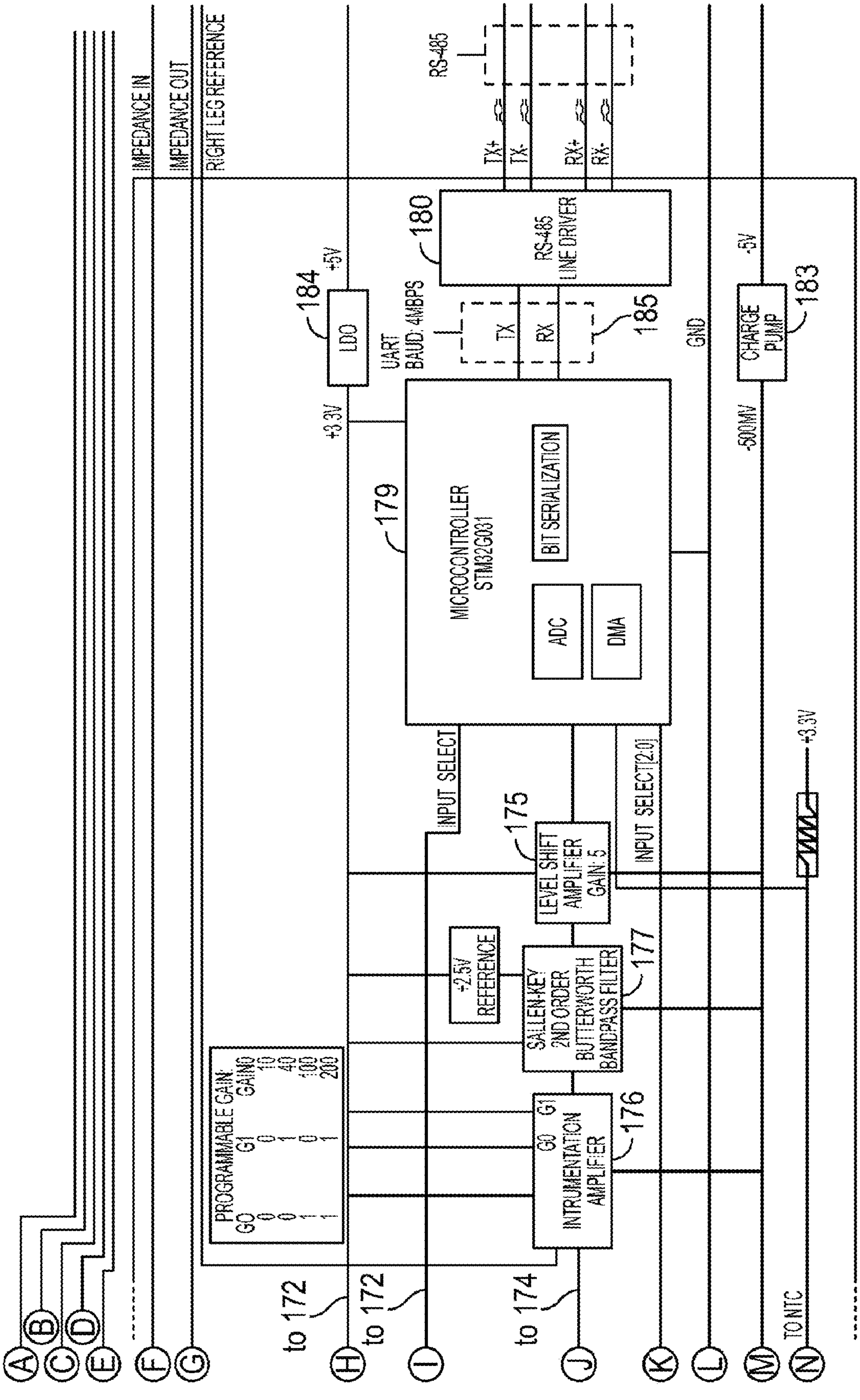

FIG. 2 is a circuit block diagram of the Huygens catheter assembly depicting the distal tip subassembly containing all functional elements for the detection, amplification, digitization, multiplexing, and communication of the native signal using multiple split electrodes. The block diagram of the catheter assembly depicts the distal tip 110 with its signal acquisition electrode inputs 111-119, connected via wire bundle 140 to the proximal end flex circuit 150 to capture the sensing potential from the endocardial surface of the heart, to multiplex (multiplexers 172, 174) and amplify the signals via a set of amplification stages, digitize the amplified signals and to transmit the multiplexed, digitized, amplified native heart signal from the endocardial surfaces via a communication protocol to an external conventional mapping station (not shown).

Figure 21:
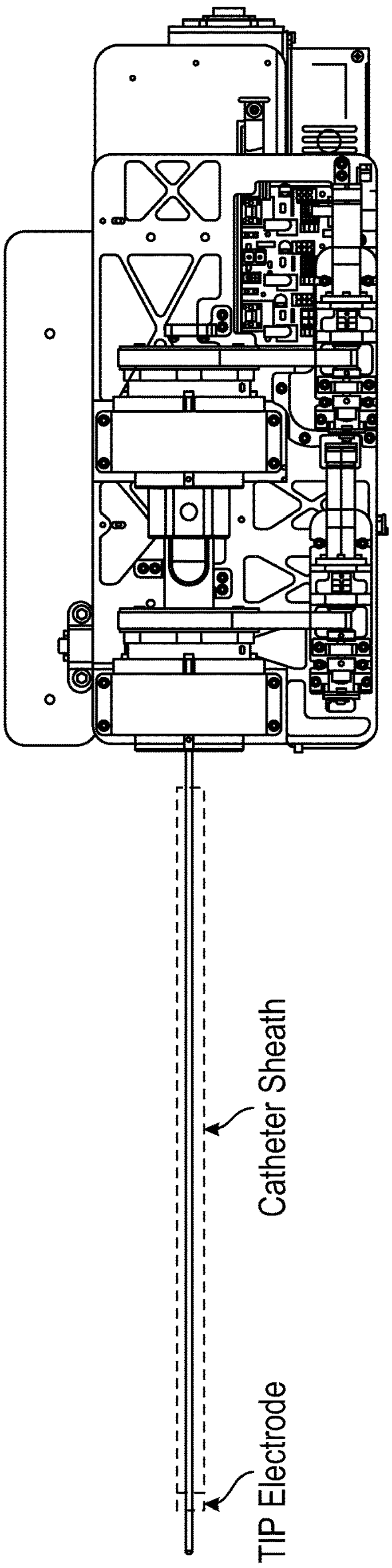
FIG. 21 is a top plan view of the robotic navigation device with the catheter loaded in it.

The circuit diagram of FIG. 2 depicts the major functional elements that form the Huygens catheter, items such as the signal processing circuits comprised of a 2-1 MUX 172, an 8-1 MUX 174, an instrumentation amplifier 176, a bandpass filter 177, a level shift amplifier gain 175, a microcontroller unit (MCU) 179, programmable gain circuit 182 controlling instrumentation amplifier 179, a charge pump 183, a 3.3V low dropout regulator (LDO) 184, an RS-485 input/output circuit (I/O) 180, and universal asynchronous receiver/transmitter (UART) 185. Electrodes 111-113 are selectively used to sense contact impedance using control signals Impedance IN and OUT, and cardiac signals as described below. The sensed signals are multiplexed into an amplifier chain 176, 177 175, digitized by MCU 179 and formatted into an UART 185 protocol and line driver 180. The multiplexed digital output/input of the circuitry of FIG. 21 is presented at line driver 180 as the transmission signals TX+. TX− and input signals RX+, RX−.

Figure 3:
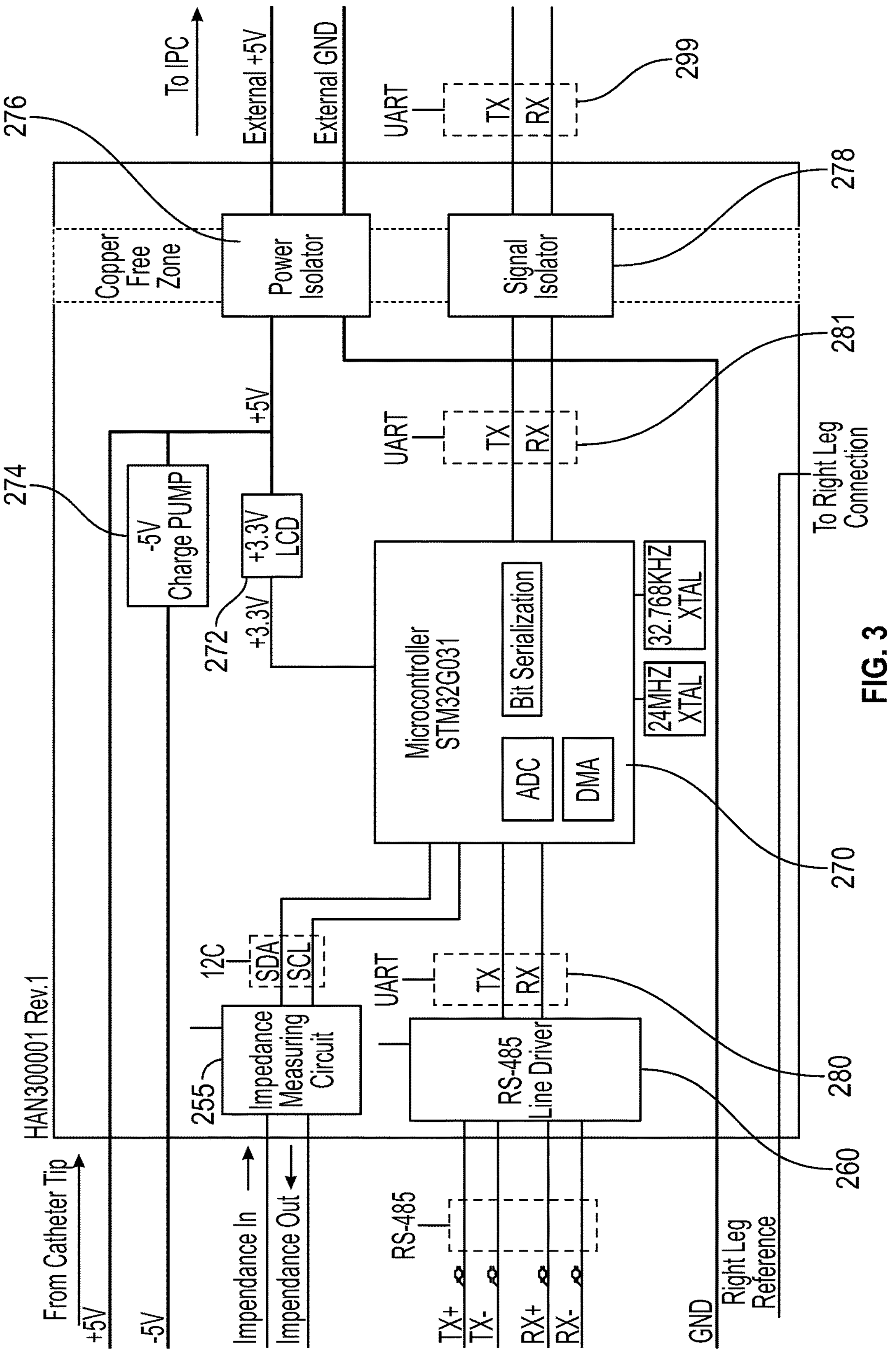
FIG. 3 is a circuit block diagram of the circuits in the catheter handle which includes the functional elements that detect contact pressure of the electrode with tissue, enabling the discerning genuine contact with the tissue from other kinds of contact conditions.

FIG. 3 is a circuit block diagram of the Huygens catheter assembly depicting the distal tip subassembly containing all functional elements for the detection, amplification, digitization, multiplexing, and communication of the native signal using multiple split electrodes. The circuit diagram depicts the handle electronic circuit containing a microcontroller 270 which maintains the communication with and control of the flex circuit 150 in FIG. 2 as well as the Impedance measuring circuit (IMC) 255 and communication protocol. The handle 200 serves multiple requirements, namely it includes an impedance circuit 255 which enables the catheter sensing element to determine whether the catheter electrodes 110 are in contact with the endocardial surfaces of the heart, or if the electrodes 110 are nested in the heart chamber and blood pool. The handle electronics of FIG. 3 includes a MCU 270 sets the priorities for communication of the signal from and to the distal and proximal electronics. The handle circuitry includes the RS-485 line driver 260, MCU 270, 3.3V LDO 272, charge pump 274, power isolator 276, signal isolator 278, UART decoder 280 and UART encoder 281. Bidirectional data and control signals, RX+, RX−, TX+, TX− are input and output from line driver 260 into and from the internal ADC and DMA of MCU 270. The impedance measuring circuit 255 is also coupling bidirectional impedance signals Impedance IN and Impedance OUT into and out of MCU 270. Data is serialized in MCU 270, formatted by UART 281 and communicated through an isolator 278 to a UART transceiver 279. Catheter power management is also provided by the circuitry in handle 200 though LDO 272, charge pump 274, and power isolator 276.

Figure 4:
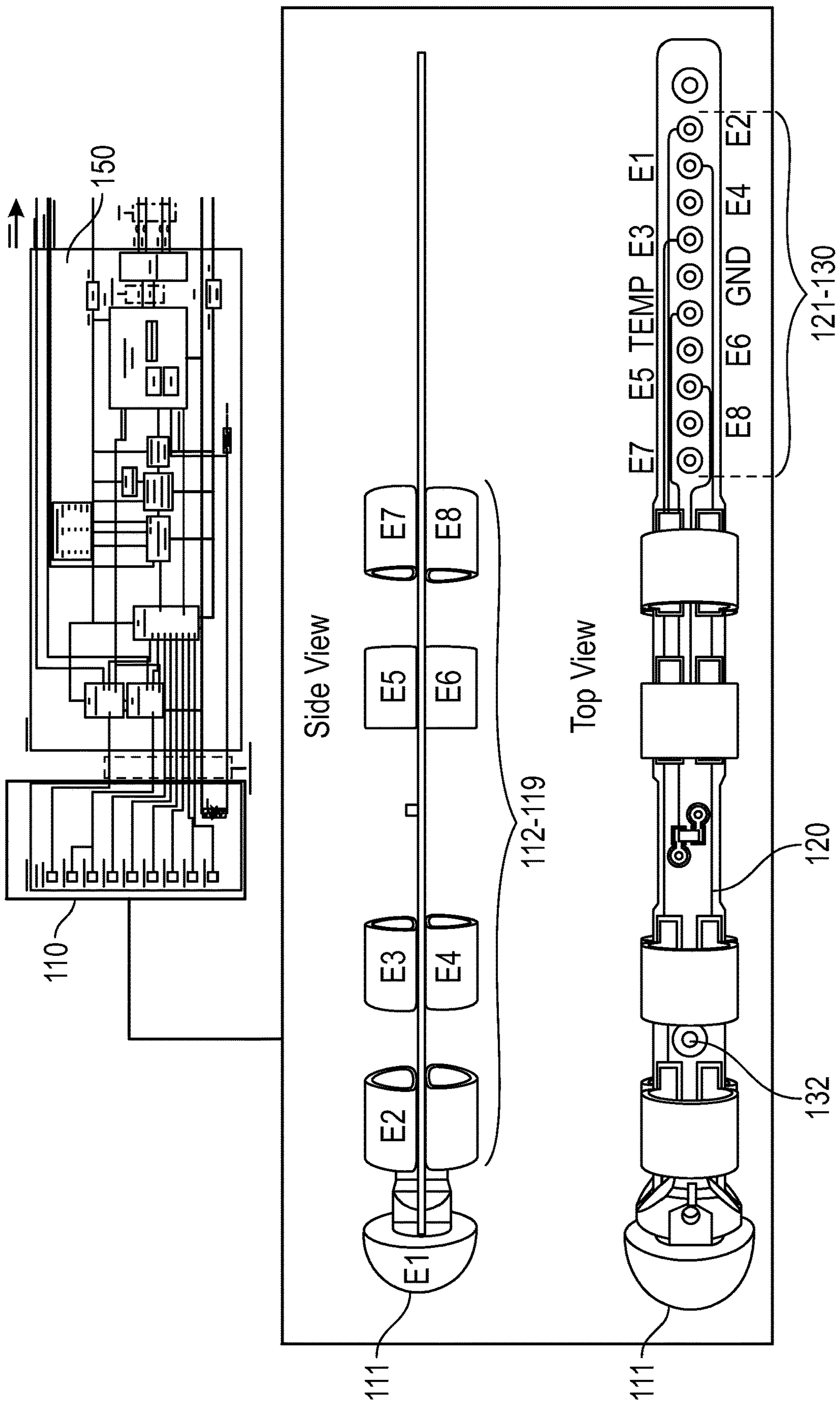
FIG. 4 is a schematic diagram of two views of geometry of the distal end of the catheter with the tip electrode, the split electrodes, and their configuration with a set of vias corresponding to the individual electrodes. A side internal view is provided above and an internal top view below. A circuit block diagram of corresponding circuitry of FIG. 2 is shown above the two internal views identifies in the figure the elements in the electrode array and in the associated circuitry as the circuitry carried by the printed circuit views shown in enlarged scale.

FIG. 4 is a schematic diagram of two views of geometry of the distal end of the catheter with the tip electrode, the split electrodes, and their configuration with a set of vias corresponding to the individual electrodes. A side internal view is provided above as an internal top view below. A circuit block diagram of corresponding circuitry shown in FIG. 2 above the two internal views identifies the elements 110 in the electrode array and in the associated circuitry. In addition a temperature sensor 132 (also shown in FIG. 2) compensates for variations of temperature to control a baseline of the signal is provided. Each electrode 110 has a dedicated connection to its corresponding via except for the first ring electrode (E2). Top and bottom half-ring electrodes 114, 115 (E3-E4) on the first ring are shorted together and identified as the E2 signal, since half-ring electrodes 114, 115 (E3-E4) need to function as a bipolar pair with the nosecone electrode (E1).

FIG. 4 further depicts the elements that form the distal end of the catheter distal tip 110 which includes the nose electrode 111, electrode split-rings 112-119 mounted on flex PCB 120, connected via distal FPC pads 121-130 to the proximal end circuit 150. One of the preferred embodiments of this geometric layout includes the use of split electrodes on each of the axial layouts of the quadrupolar catheter configuration, whereby the distal most electrode pair 112-113 is able to pick up the DC potential signal from the endocardial surface as either electrode 111 or its counterpart pair 112-113 are touching the endocardial surface thereby providing a signal via the impedance measuring circuit 255 located at the handle electronic board 250, which sends an AC test current through the tip electrode 111 in combination with electrode pair 112-113 to sense impedance to determine whether the catheter electrodes 110 are in contact with the endocardial surface or situated within the blood pool in the heart chamber. Such determination is further described in detail by FIG. 13, where the usefulness and clinical value of this circuit is further described.

Figure 5:
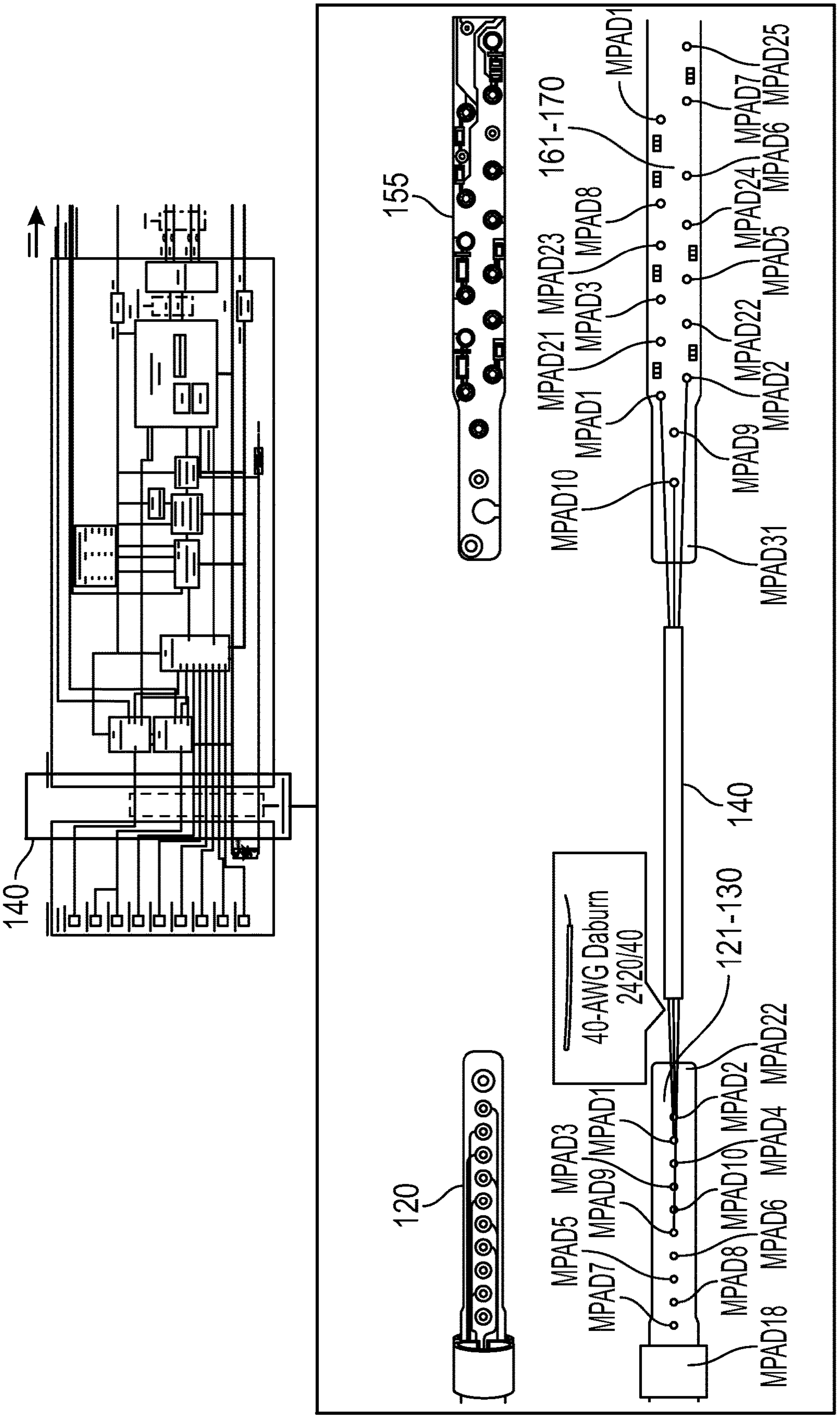
FIG. 5 shows two internal top plan layouts of the Huygens catheter distal electrode flex circuit, the interconnecting cable and the interface to the electronic circuit assembly, the upper plan layout is a pictorial illustration of the distal electrode flex circuit and interface and the lower plan layout is a diagrammatic depiction of the distal electrode flex circuit connected by the interconnecting cable to the interface. A block diagram of the corresponding circuitry in FIG. 2 is shown above the two internal top plan views and identifies the interconnecting cable.

FIG. 5 shows two internal top plan layouts of the Huygens catheter distal electrode flex circuit, the interconnecting cable 140 and the interface to the electronic circuit assembly. The upper plan layout in FIG. 5 is a pictorial illustration of the distal electrode flex circuit and interface and the lower plan layout in FIG. 5 is a diagrammatic depiction of the distal electrode flex circuit connected by the interconnecting cable 140 to the interface. A block diagram of the corresponding circuitry of FIG. 2 shown is shown above the two internal top plan views and identifies the interconnecting cable 140. FIG. 5 illustrates certain manufacturing and physical attributes of the Huygens catheter. The layout further shows the distal flex circuit 120 FPC tabs (MPAD1-MPAD10) which are connected to a set of vias located at the end of the distal FPC 120 by employing a 40 AWG Daburn wire bundle 140. The number system describes the sequence of the electrodes and their location. Proximal FPC (MPAD1-MPAD10) through 40 AWG Daburn wires are bundled in a strand. For assembly convenience, the corresponding vias have same numbering.

Distal FPC 120 containing the electrodes with distal FPC tabs 121-130, wire bundle 140, proximal end 150, proximal FPC tabs 161-170 are shown for clarity, and their separation with the bundle of interconnecting wire 140 enables free rotation of the distal catheter tip 120 along the Y- and Z-axis for rotation and along the X-axis for translation without any limitation associated with the stiffness of the catheter shaft because of electronic circuit FPC 155 or the distal FPC 120. Both FPC 155 and FPC 120 are linked mechanically by wire bundle 140 to enable a high degree of movement along any axis.

Figure 6:
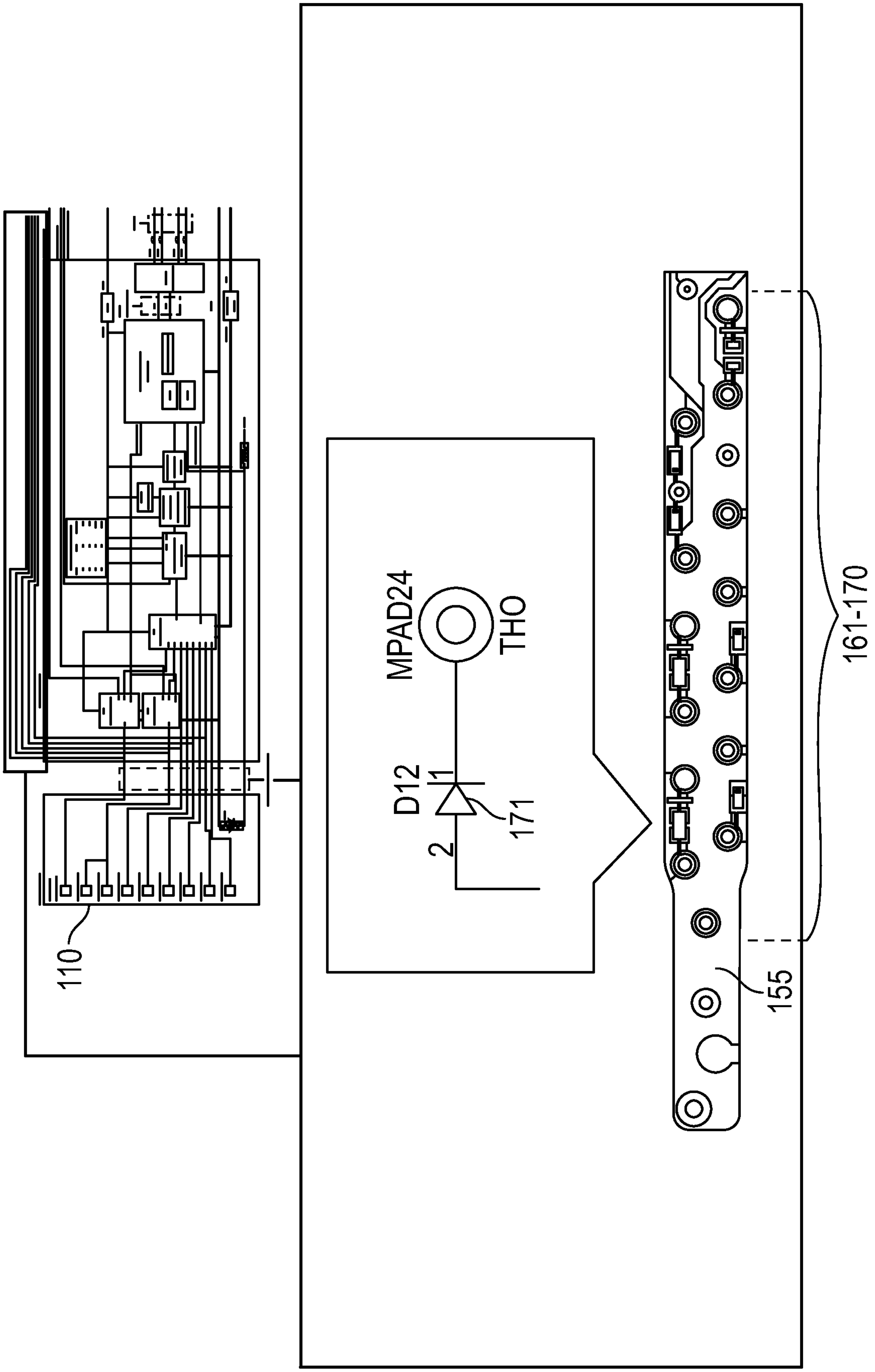
FIG. 6 is a diagram of the isolation and trilateralization circuit and is identified in the circuit block diagram of FIG. 2 above the diagram.

FIG. 6 is a diagram of the isolation and trilateralization circuit shown and is identified in the circuit block diagram above the diagram. The isolation and trilateralization circuit is where conventional RF trilateralization signals to map the position of the catheter 100 are picked up from electrodes 111-119 and independently carried with a set of wires through the shaft of the catheter 100 and are transmitted to an external system, such as a conventional CARTO/EnSite NavX, where trilateralization is computed and displayed using position and orientation vector data collected from external RF patches mounted on the body of the patient according to conventional electrophysiology practice, and augmented with additional information such as impedance, DC potential, timing and temperature, and varieties of other electrical parameters as disclosed below. FIG. 6 depicts the proximal FPC 155, which receives the signals from the electrodes 111-119 provided to proximal FPC tabs 161-170 each through a Schottky protection diode 171.

FIG. 7.1 is a block diagram of the multiplexing circuit located proximal to the flexible printed circuit board (FPC) and FIG. 7.2 shows its physical placement on the FPC is a perspective view. In FIG. 7.3 the multiplexing circuit is identified in the circuit block diagram of FIG. 2. The inputs from nosecone electrode 111 in FIG. 4 and first ring electrodes (E1 & E2) 112-113 are coupled to a pair of 2-to-1 MUXs 172. These sets of electrodes have a dual-function and their use is determined by the MCU 270 located in the handle 200 which switches the use of the electrodes 112-113 for either impedance measurement (contact or non-contact of the electrodes to endocardial surface), or for DC potential measurement of the endocardial surface. The IMP SEL pins of the 2-to-1 MUX 172 control which function these electrodes serve. The outputs of the two MUXs 172 along with the rest of 6 input signals (E3-E8) connected to 8-to-1 MUX 174 are multiplexed to a single analog signal. Each input via from proximal FPC 161-170 (MPAD1-MPAD8) has an ESD protection diode 173 (D3-D10). Electrodes E1, E2, E3, E5, and E7 have split traces that connect to the mapping station such as a conventional EnSite NavX/CARTO (not shown) for the purpose of tri-lateralization of locating signals as described in FIG. 6. FIG. 7 further depicts the distal tip 110, proximal end 150, proximal FPC tabs 161-170, Schottky diode 171, 2-1 MUX signal converter 172, protection diode 173, and 8-1 MUX 174.

FIG. 8.1 is a schematic circuit diagram depicting the amplification elements of the Huygens catheter with its physical location on the FPC shown in FIG. 8.2 in perspective view depiction. FIG. 8.3 identifies on the circuit diagram of FIG. 2 the corresponding portion of the circuitry. The amplification is provided where the multiplexed analog signals enter instrumentation amplifier 176 (MAX41400), and are referenced to the patient's right leg, where a standard bipolar recording is provided utilizing a right limb lead to enable the measurement of the potential difference between the catheter and its limb reference point. The amplifier 176 has a programmable gain set to 200x. After the initial amplification, the signal is input to a second order Butterworth lowpass filter 177 configured in a Sallen-Key topology. The filter 177 is designed to have-3 dB cutoff frequency at 1 KHz in order to filter out the trilateralization signals. The second stage of the operational signal amplifier 175 shifts the entire signal so that its voltage range is entirely in positive domain. FIG. 8.1 depicts the distal tip 110, proximal end 150, 8-to-1 MUX 174, Instrumentation amp 176, Butterworth bandpass filter 177, and signal amp 175.

FIG. 9.1 is a schematic circuit diagram of the A/D processing circuit for the DC voltage potential with its physical location on the FPC shown in FIG. 9.2 in perspective view. FIG. 9.3 identifies on the circuit diagram of FIG. 2 the corresponding portions of the circuitry. FIG. 9.1 illustrates the A/D processing of the DC voltage potential, where the amplified signal is input into (STM32G031Y8Y6TR) microcontroller MCU 179 where its internal ADC (not shown) converts the processed cardiac signal into digital format. The microcontroller (MCU) 179 also collects the temperature data from MPAD9. Thereafter, the MCU 179 compiles these converted digital signals and outputs in a UART format with a BAUD rate of 4 Mbps. The microcontroller MCU 179 is programmed through J1 tab 182, which is removed once the component has been programmed.

FIG. 10.1 is a schematic circuit diagram of the data transmission elements with their physical location on the FPC shown in FIG. 10.2. FIG. 10.3 identifies on the circuit diagram of FIG. 2 the corresponding circuitry. FIG. 10.1 depicts the data transmission scheme, where the UART signal is processed through an RS-485 transmitter 186 and receiver 187 before sent to the handle PCB (HAN300001) 251. RS-485 transmitter 186 allows the data transmission to be done in a differential paired mode, providing immunity over EMI in a long strand of wires.

FIG. 11.1 is a block circuit diagram of the cardiac signal flow elements with their physical layout on the FPC shown in FIG. 11.2 with the wiring labels. FIG. 11.3 identifies on the circuit diagram of FIG. 2 the corresponding circuitry. FIG. 11.1 depicts the cardiac signal flow, whereby the 40-AWG Daburn wires 205 from the tip are connected to the distal portion of handle PCB 251 (HAN300001). As shown in the assembly drawing, the via labeling for wiring connection corresponds to the tip FPCs for ease of wire assembly. From the handle 200 to the external devices, bigger diameter wires are used, resulting in bigger vias (1 mm hole diameter).

FIG. 12.1 is a circuit block diagram of communication elements used between the electrodes and the electronic circuit with their physical layout on the FPC shown in FIG. 12.2. FIG. 12.3 identifies on the circuit diagram of FIG. 2 the corresponding circuitry. FIG. 12.1 illustrates the communication format between the electrodes and the electronic circuit 261, which outputs the RS-485 differential pair signals connected to vias MPAD16 to MPAD18. These signals are input into full-duplex RS-485 driver 260, where the signals are converted back to a UART format. The converted UART signals are input to the microcontroller 270 and processed.

FIG. 13.1 is a schematic circuit diagram of the impedance measuring circuit with its physical layout on the FPC shown in FIG. 13.2. FIG. 13.3 identifies on the circuit diagram of FIG. 2 the corresponding circuitry. FIG. 13.1 illustrates the impedance measuring circuit, comprising an impedance converter AD5933 254 and two operational amplifiers 256, 257. Impedance converter AD5933 254 sends a small current to MPAD19 which is communicated to the 2-to-1 MUX 172 at the proximal FPC 155. When the read signal is asserted, the impedance-reading current travels through the nosecone electrode 111 and returns to the first ring electrodes 112-113. The current returns to the handle 200 via MPAD20, and back to impedance converter AD5933 254. The calculated impedance is sent to the microcontroller (MCU) 270 via an inter-integrated circuit (I2C) communication protocol.

FIGS. 14.1 and 14.2 are schematic circuit diagrams of the universal asynchronous receiver-transmitter (UART) for the communication protocol and the signal integration of the cardiac signal output with its physical layout on the FPC shown in FIG. 14.3. FIG. 14.4 identifies on the circuit diagram of FIG. 2 the corresponding circuitry. FIGS. 14.1 and 14.2 illustrate the UART communication protocol and the signal integration of the cardiac signal output, where the microcontroller MCU 270 combines the digital input from the tip FPC 120 and the impedance data. The MCU 270 combines all the data and outputs the combined data via a UART protocol. To comply with medical device regulations, all signals and power must be isolated. Therefore, the UART signals are optically isolated before connecting to an external programmable logic controller (PLC). The circuit of FIG. 14.2 depicts the serial communication channel 1 265, serial communication channel 2 266, handle MCU 270, power isolator 276, and signal isolator 278.

FIG. 15.1 is a schematic diagram of the power circuitry and isolation technique of the Huygens catheter with its physical layout on the FPC shown in FIG. 15.2. FIG. 15.3 identifies on the circuit diagram of FIG. 2 the corresponding circuitry. FIG. 15.1 shows that the power circuitry and isolation circuitry of the Huygens catheter receives +5V power from PLC's USB connector 285. The voltage and ground from external PLC (not shown) is isolated before it powers the catheter 100. The 3.3V low dropout voltage regulator (LDO) 272 supplies local electronic components while the isolated +5V and the −5V that is generated from the charge pump 274 is connected to the tip FPCs. FIG. 15.3 depicts the catheter handle electronics 250, serial communication channel 1 265, serial communication channel 2 266, handle MCU 270, handle LDO 272, handle charge pump 274, power isolator 276, and power input 285.

Proteus Robot

Figure 16:
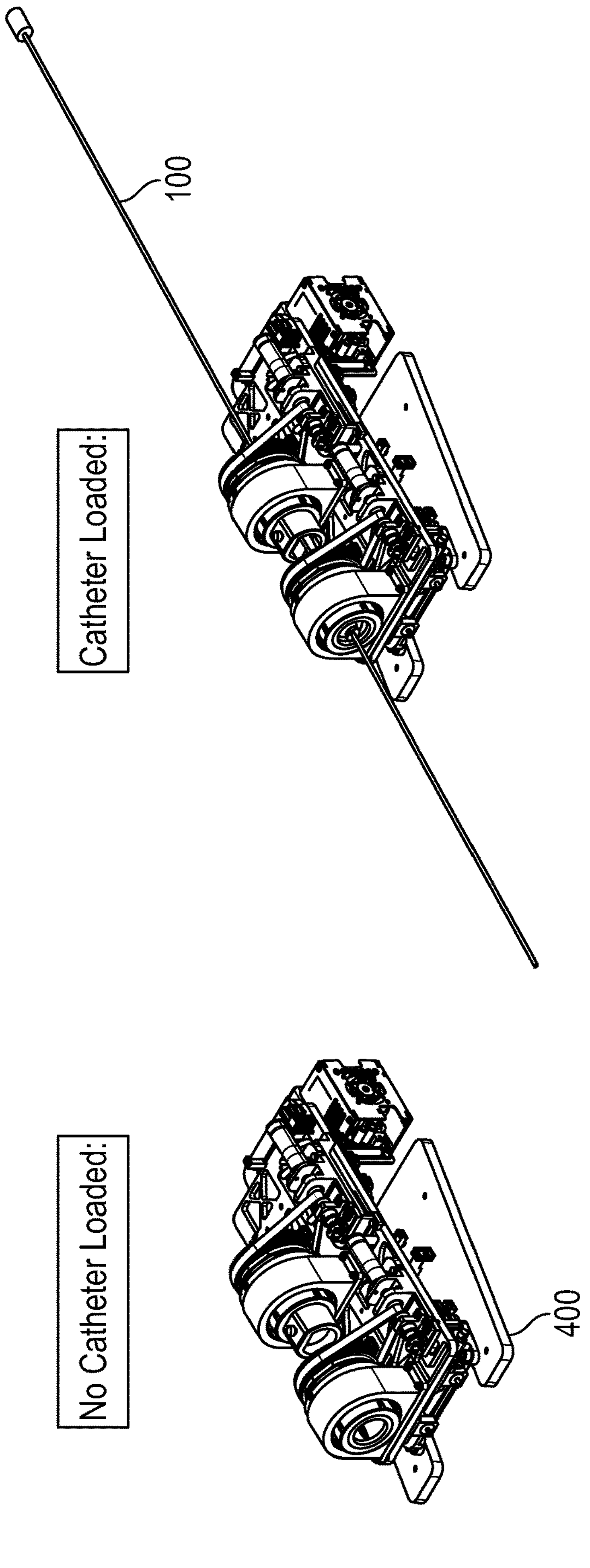
FIG. 16 is a perspective view of the robotic navigation device without catheter loaded as shown on the left side and with catheter inserted as shown on the right side of the figure.
Figure 17:
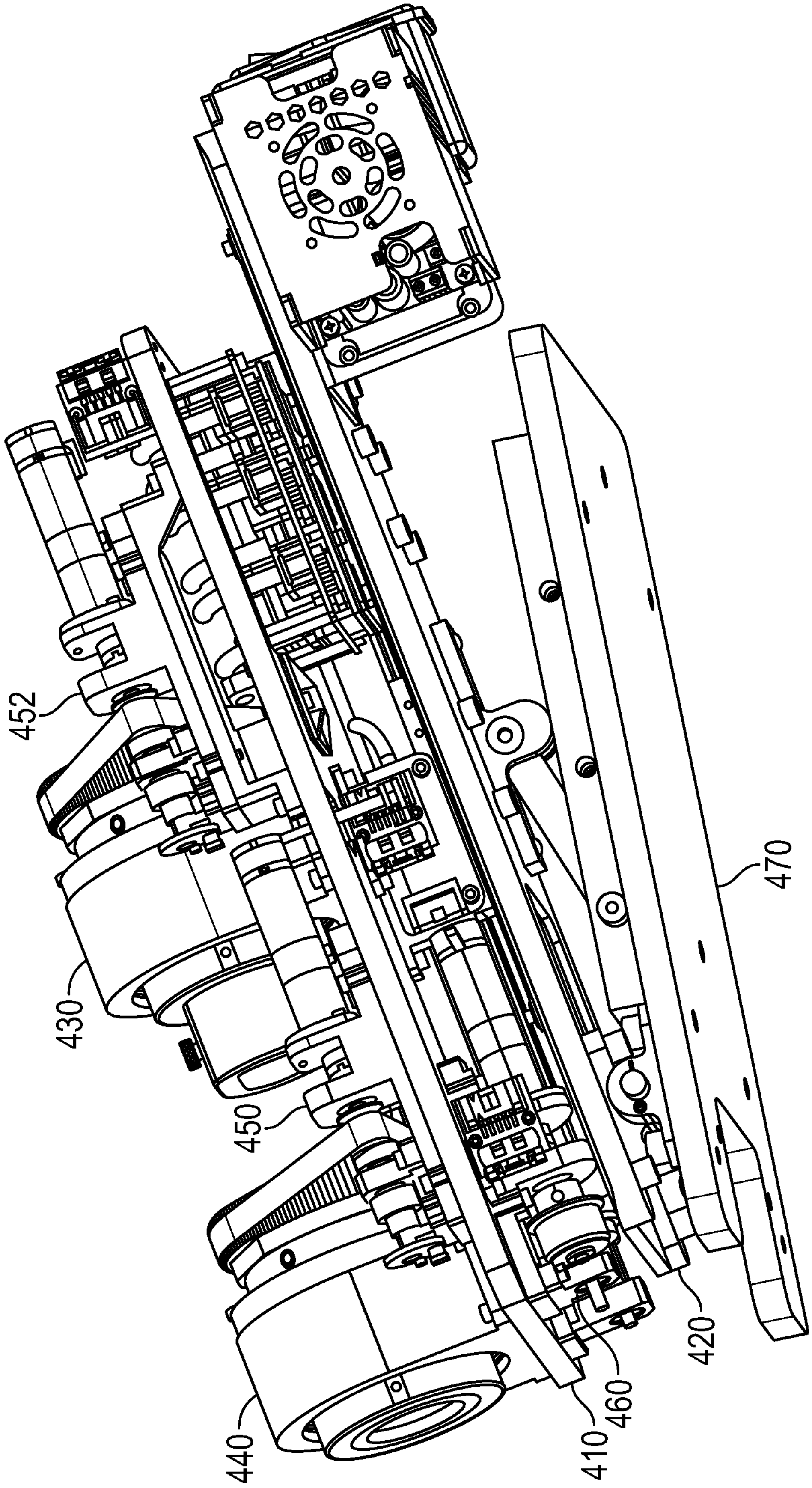
FIG. 17 is a perspective side view of the robotic navigation device shown some of its mechanical components.
Figure 18:
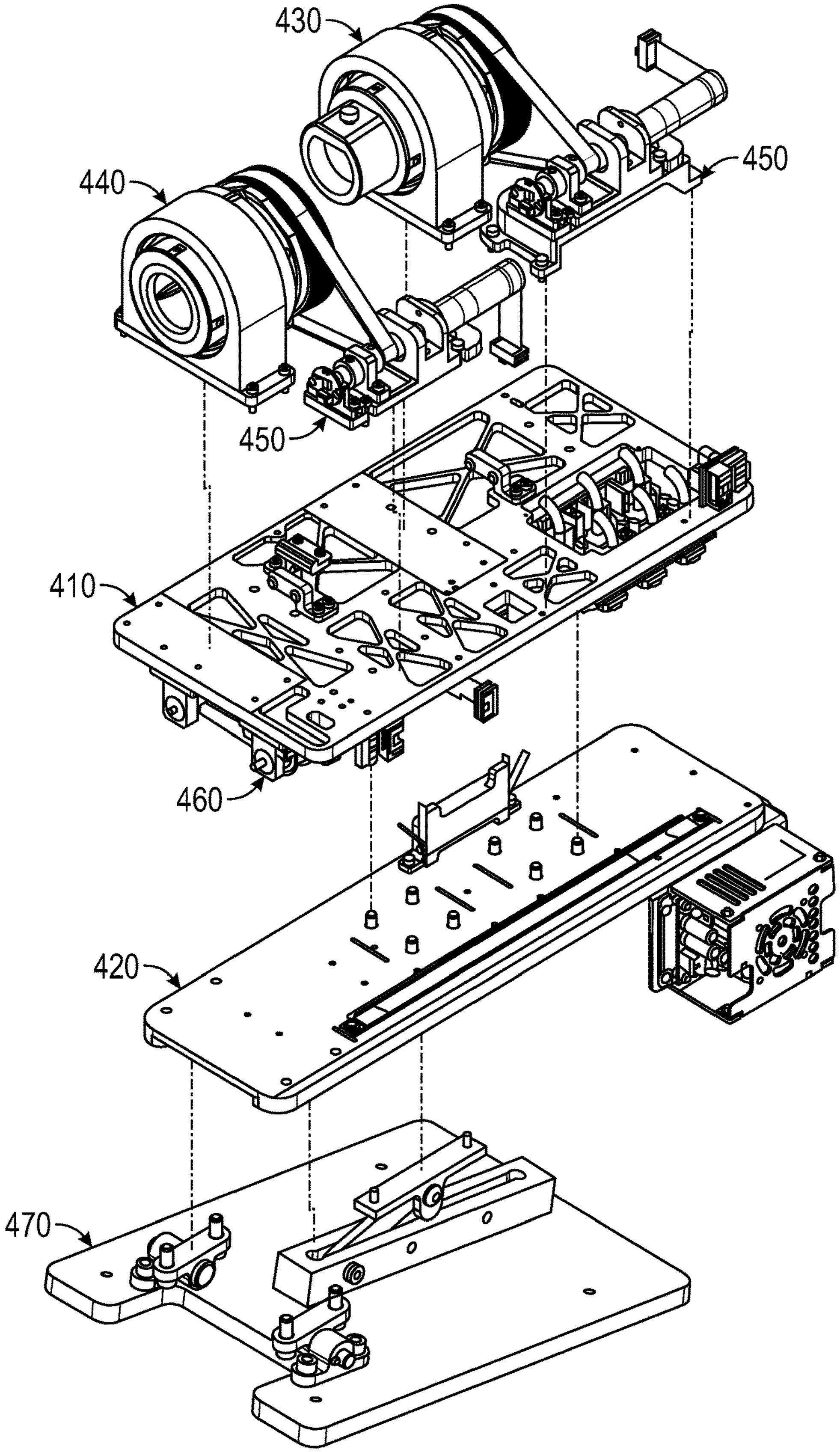
FIG. 18 is an exploded perspective view of the robotic navigation device better displaying some of its mechanical components.
Figure 19:
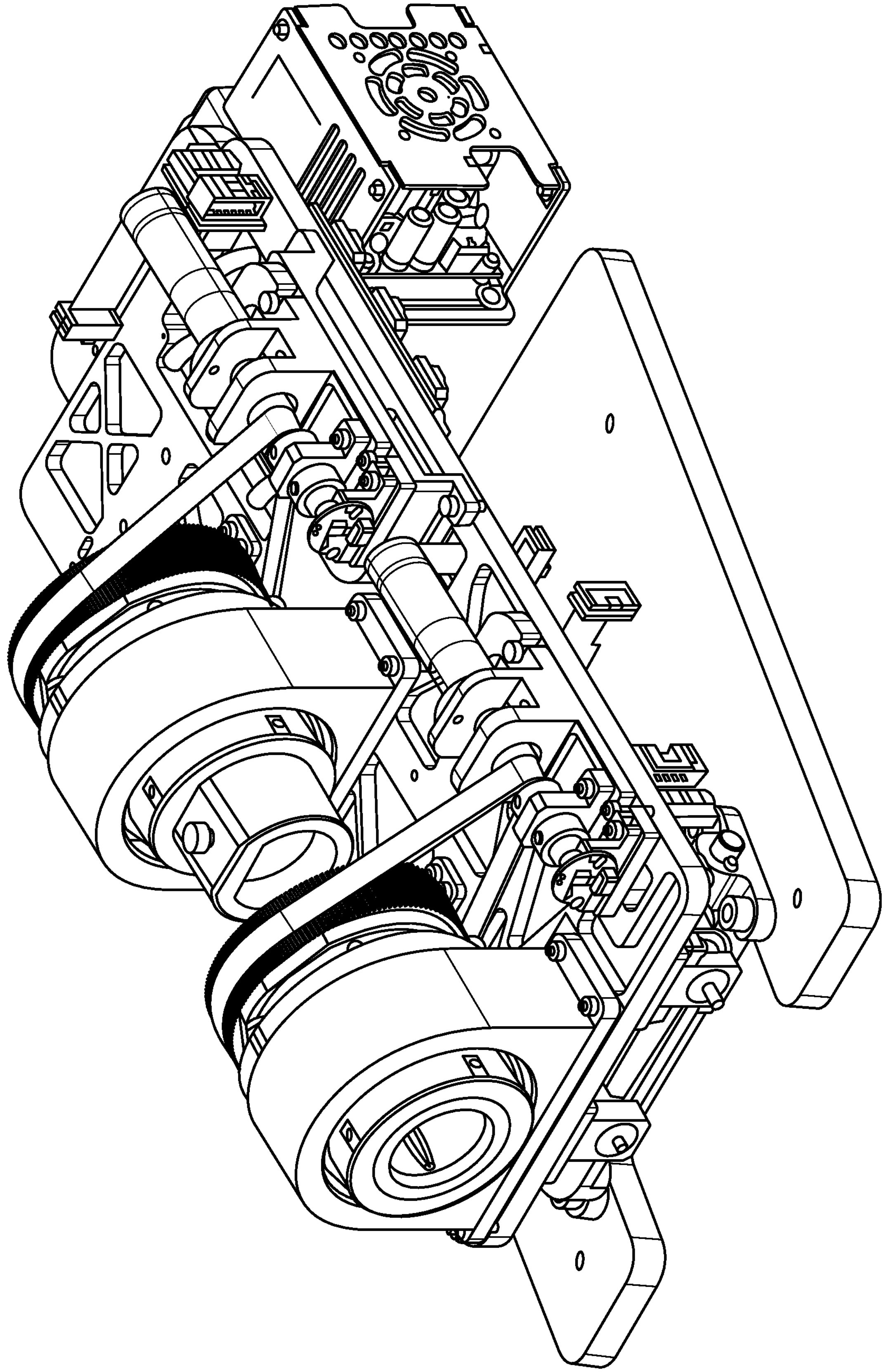
FIG. 19 is a top perspective view of the robotic navigation device.
Figure 20:
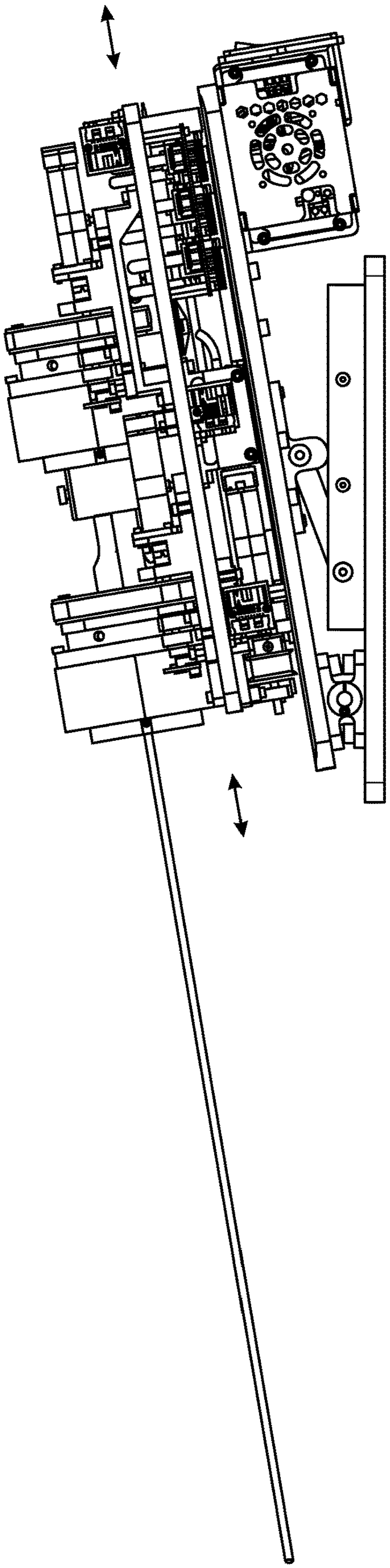
FIG. 20 is a side plan view of the robotic navigation device with the catheter loaded in it.

FIG. 16 is a perspective view of the robotic navigation device 400 without catheter 100 loaded as shown on the left side and with catheter 100 inserted as shown on the right side of the figure. FIG. 17 is a perspective side view of the robotic navigation device shown some of its mechanical components, showing the top carriage assembly 410, baseplate 420, proximal pillow block 430, distal pillow block 440, deflection-rotary drive (DRD) 450, rotary drive 452, linear translation drive (LTD) 460, angle mounting system (AMS) 470. Handle 200 is disposed in device 400. DRD 450 engages knob 202 to bidirectionally rotate it using a computer controlled electric motor and toothed belt combination to selectively deflect the catheter tip 120. DRD drive 452 uses a computer controlled electric motor and toothed belt combination to selectively rotate the body of handle 200 thereby rotating the catheter as a unit. Linear translation drive 460 uses a computer controlled linear electric motor to selectively translate the upper portion of device 400, namely pillow blocks 440 and 430 to translate handle 200 carried therein and catheter 100. The angular inclination of lower platforms 420 and 470 are varied using a scissor hinge connecting platforms 420 and 470. FIG. 18 is an exploded perspective view of the robotic navigation device better displaying some of its mechanical components, showing again the top carriage assembly 410, baseplate 420, proximal pillow block 430, distal pillow block 440, deflection-rotary drive (DRD) 450, linear translation drive (LTD) 460, angle mounting system (AMS) 470. FIG. 19 is a top perspective view of the robotic navigation device 400. FIG. 20 is a side plan view of the robotic navigation device with the catheter loaded in it. FIG. 21 is a top plan view of the robotic navigation device with the catheter loaded in it.

Many alterations and modifications may be made by those having ordinary skill in the art without departing from the spirit and scope of the invention. Therefore, it must be understood that the illustrated embodiments have been set forth only for the purposes of example and should not be taken as limiting the scope of the invention.

Therefore, it must be understood that the illustrated embodiment has been set forth only for the purposes of example and that it should not be taken as limiting the invention as defined by the following claims. For example, not withstanding the fact that the elements of a claim are set forth below in a certain combination, it must be expressly under stood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub-combination. Accordingly, the scope of the invention is limited only by the claims and equivalents thereto.

What is claimed is:

1. A catheter comprising:
- a handle;
- a distal Tip;
- a sheath that extends between the handle and the distal tip;
- a plurality of electrodes disposed on an external surface of the distal tip, the plurality of electrodes being configured to generate cardiac signal measurements;
- a distal tip circuitry contained within the distal tip;
- handle circuitry contained within the handle; and
- one or more communication elements formed within the sheath for interconnecting the distal tip circuitry and the handle circuitry;
- wherein a subset of the plurality of electrodes are configured to generate impedance measurements in addition to the cardiac signal measurements;
- wherein the distal tip circuitry is configured to cause the subset of the plurality of electrodes to switch between generating the impedance measurements and the cardiac signal measurements;
- wherein the distal tip circuitry is configured to repeatedly receive the cardiac signal measurements from the plurality of electrodes, multiplex the cardiac signal measurements to create a combined signal, and amplify and digitize the combined signal to thereby repeatedly generate a digital signal representing the cardiac signal measurements;
- wherein the distal tip circuitry is further configured to transmit the impedance measurements and the digital signals to the handle circuitry via the one or more communication elements; and
- wherein the handle circuitry is configured to combine the impedance measurements with the digital signals and to output combined data including the impedance measurements and the digital signals to an external system.

2. The catheter of claim 1, wherein the plurality of electrodes includes a nosecone electrode and an array of electrode pairs, each electrode pair of the array of electrode pairs comprising top and bottom half-ring electrodes.

3. The catheter of claim 2, wherein the subset of the plurality of electrodes includes the nosecone electrode and a first electrode pair in the array of electrode pairs.

4. The catheter of claim 2, wherein the distal tip circuitry includes at least one first multiplexer that is configured to cause the subset of the plurality of electrodes to switch between generating the impedance measurements and the cardiac signal measurements.

5. The catheter of claim 4, wherein the distal tip circuitry includes a second multiplexer that is configured to repeatedly receive the cardiac signal measurements from the plurality of electrodes and multiplex the cardiac signal measurements to create the combined signal.

6. The catheter of claim 5, wherein the second multiplexer receives the cardiac signal measurements generated by the subset of the plurality of electrodes via the at least one first multiplexer.

7. The catheter of claim 4, wherein the at least one first multiplexer is configured to cause an AC test current to flow through the subset of the plurality of electrodes to generate the impedance measurements.

8. The catheter of claim 7, wherein the handle circuitry includes an impedance measuring circuit that provides the AC test current.

9. The catheter of claim 8, wherein the handle circuitry is configured to output a read signal to control the at least one first multiplexer to thereby cause the AC test current to flow through the subset of the plurality of electrodes to generate the impedance measurements.

10. The catheter of claim 9, wherein the impedance measuring circuit is configured to receive the impedance measurements from the at least one first multiplexer.

11. The catheter of claim 4, wherein the at least one first multiplexer comprises two first multiplexers.

12. The catheter of claim 1, wherein the distal tip circuitry implements a first amplification stage, a filtering stage, and a second amplification stage.

13. The catheter of claim 1, wherein the plurality of electrodes includes a nosecone electrode, a first pair of top and bottom half-ring electrodes positioned adjacent the nosecone electrode, and multiple additional pairs of top and bottom half-ring electrodes that are spaced along a length of the distal tip.

14. The catheter of claim 13, wherein the top half-ring electrode in the first pair is shorted to the bottom half-ring electrode in the first pair.

15. The catheter of claim 14, wherein each of the nosecone electrode, the first pair of top and bottom half-ring electrodes, each top half-ring electrode of the additional pairs, and each bottom half-ring electrode of the additional pairs generates cardiac signal measurements.

16. The catheter of claim 15, wherein the subset of the plurality of electrodes includes the nosecone electrode and the first pair of top and bottom half-ring electrodes and the impedance measurements are generated when an AC test current flows through the nosecone electrode and the first pair of top and bottom half-ring electrodes.

17. The catheter of claim 1, wherein the external system is a mapping system.

18. The catheter of claim 1, wherein the external system is a robot for controlling the catheter.

19. The catheter of claim 1, wherein the combined data including the impedance measurements and the digital signals are output to the external system via universal asynchronous receiver-transmitter (UART) protocol.

20. A robotic guidance and control system, comprising a robot, a control system and a catheter, for robotically controlling the catheter to perform one or more electrophysiological procedures in combination with a remote mapping station comprising:
- the catheter, comprising:
  - a handle;
  - a distal tip;
  - a sheath that extends between the handle and the distal tip;
  - a plurality of electrodes disposed on an external surface of the distal tip, the plurality of electrodes being configured to generate cardiac signal measurements;
  - a distal tip circuitry contained within the distal tip;
  - handle circuitry contained within the handle; and
  - one or more communication elements formed within the sheath for interconnecting the distal tip circuitry and the handle circuitry;

wherein a subset of the plurality of electrodes are configured to generate impedance measurements in addition to the cardiac signal measurements;

wherein the distal tip circuitry is configured to cause the subset of the plurality of electrodes to switch between generating the impedance measurements and the cardiac signal measurements;

wherein the distal tip circuitry is configured to repeatedly receive the cardiac signal measurements from the plurality of electrodes, multiplex the cardiac signal measurements to create a combined signal, and amplify and digitize the combined signal to thereby repeatedly generate a digital signal representing the cardiac signal measurements; and wherein the distal tip circuitry is further configured to transmit the impedance measurements and the digital signals to the handle circuitry via the one or more communication elements;

the robot that is configured to engage the handle for selectively deflecting the distal tip of the catheter, rotating the catheter or translating the catheter in response to commands from the control system; and the control system, comprising the handle circuitry, operatively coupled to the robot and the remote mapping station, the control system configured to:

1) receive the impedance measurements, the digital signals and corresponding catheter position and orientation data;

2) determine, in real time, an actual catheter position from the catheter position and orientation data;

3) determine, in real time and based on the impedance measurements and the digital signals, a plurality of independent variables that correspond to physiological motion including at least a cardiac cycle and respiratory motion;

4) normalize the plurality of independent variables by transforming the catheter position and orientation data into a common coordinate system;

5) generate a spatially-referenced electro-anatomical map that associates the plurality of normalized independent variables with the catheter position and orientation data within the common coordinate system;

6) determine, based on the spatially-referenced electro-anatomical map, a desired catheter position;

7) generate control signals based on a comparison of the desired catheter position and the actual catheter position; and 8) automatically actuate the robot in a closed-loop manner based on the control signals to move the catheter from the actual catheter position to the desired catheter position to thereby perform the one or more electrophysiological procedures.

* * * * *